(12) United States Patent
Dolente et al.

(10) Patent No.: US 8,492,376 B2
(45) Date of Patent: Jul. 23, 2013

(54) HETEROARYL-CYCLOHEXYL-TETRAAZABENZO[E]AZULENES

(75) Inventors: Cosimo Dolente, Allschwil (CH); Patrick Schnider, Bottmingen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 208 days.

(21) Appl. No.: 13/086,422

(22) Filed: Apr. 14, 2011

(65) Prior Publication Data

US 2011/0263578 A1 Oct. 27, 2011

(30) Foreign Application Priority Data

Apr. 21, 2010 (EP) .................................... 10160643

(51) Int. Cl.
*A61P 9/00* (2006.01)
*A61P 15/00* (2006.01)
*A61P 25/00* (2006.01)
*A61K 31/5517* (2006.01)
*C07D 487/04* (2006.01)

(52) U.S. Cl.
USPC .......................................... 514/220; 540/563

(58) Field of Classification Search
USPC .......................................... 514/220; 540/563
See application file for complete search history.

(56) References Cited

U.S. PATENT DOCUMENTS

| 7,265,104 B2 | 9/2007 | Elliott et al. |
| 2002/0103373 A1 | 8/2002 | Hockstra et al. |
| 2007/0167430 A1 | 7/2007 | Ryckmans |
| 2007/0249585 A1 | 10/2007 | Johnson |
| 2011/0245237 A1 | 10/2011 | Dolente et al. |
| 2011/0251183 A1 | 10/2011 | Dolente et al. |
| 2011/0263578 A1 | 10/2011 | Dolente et al. |
| 2011/0275801 A1 | 11/2011 | Dolente et al. |

FOREIGN PATENT DOCUMENTS

| EP | 2292621 | 3/2011 |
| KR | 2007/0020462 | 2/2007 |
| WO | 96/22292 | 7/1996 |
| WO | 02/083681 | 10/2002 |
| WO | 2004/074291 | 9/2004 |
| WO | 2005/068466 | 7/2005 |
| WO | 2006/021882 | 3/2006 |
| WO | 2006/114706 | 11/2006 |
| WO | 2006/123242 | 11/2006 |
| WO | 2008/084005 | 7/2008 |
| WO | 2010/057795 | 5/2010 |

OTHER PUBLICATIONS

Landgraf et al., Regul. Pept. 59:229-239 ( 1995).
(Opposition in Costa Rican Appl 2011-0220 Sep. 20, 2011).
Van Kerckhoven et al., Eur. J. Pharmacol. 449:135-141 (2002).
Ebner et al., Eur. J. Neurosci. 15:384-388 (2002).
Altemus et al., Arch. Gen. Psychiatry 49:9-20 (1992).
Regier et al., Br. J. Psychiatry Suppl.:24-28 (1998).
Aughton et al., Br. J. Pharmacol.:253 (2008).
Robben et al., Am. J. Physiol. Renal. Physiol. 291:F257-270 (2006).
(International Search Report PCT/EP2011/056071 May 12, 2011).
Gupta et al., Br. J. Pharmacol. 155:118-126 (2008).
Raskind et al., Biol. Psychiatry 22:453-462 (1987).
Neumann, J. Neuroendocrinol. 20:858-865 (2008).
Bielsky et al., Neuropsychopharmacology 29:483-493 (2004).
Brouard et al., Bjog. 107:614-619 (2000).
Michelini et al., Ann. NY Academy Science 897:198-211 (1999).
Yirmiya et al., 11:488-494 (2006).
Kendler et al., Arch. Gen. Psychiatry 60:789-796 (2003).
Thompson et al., Psychoneuroendocrinology 29:35-48 (2004).
Gal et al., Progress in Brain Research, Elsevier 139:197-210 XP001205440 (2002).
(International Search Report for PCT/EP2011/057368 Jul. 14, 2011).
(International Search Report for PCT/EP2009/064804 Jan. 14, 2010).
(International Search Report PCT/EP2011/056391 Jun. 27, 2011).
(International Search Report for PCT/EP2011/054582 Mar. 25, 2011).
(International Search Report PCT/EP2009/065354 Feb. 8, 2010).
Ebner et al., Eur. J. Neuroscience 15:384-388 (2002).
Liebsch et al., Regulatory Peptides 59a(2):229-239 (1995).
(International Search Report PCT/EP2011/055516 May 23, 2011).
The Taiwanese Office Action, issued on Mar. 12, 2013, in the corresponding Taiwanese application No. 100113411.

Primary Examiner — Brenda Coleman

(57) ABSTRACT

The present invention is concerned with heteroaryl-cyclohexyl-tetraazabenzo[e]azulenes of formula I

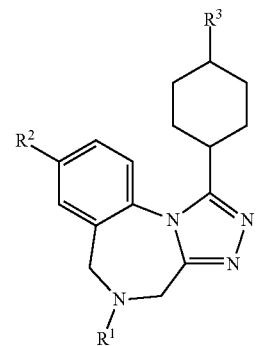

wherein $R^1$, $R^2$ and $R^3$ are as described herein.

The compounds according to the invention act as V1a receptor modulators, and in particular as V1a receptor antagonists, their manufacture, pharmaceutical compositions containing them and their use as medicaments. The active compounds of the present invention are useful as therapeutics acting peripherally and centrally in the conditions of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior.

23 Claims, No Drawings

HETEROARYL-CYCLOHEXYL-TETRAAZABENZO[E]AZULENES

PRIORITY TO RELATED APPLICATION(S)

This application claims the benefit of European Patent Application No. 10160643.2, filed Apr. 21, 2010, which is hereby incorporated by reference in its entirety.

BACKGROUND OF THE INVENTION

Vasopressin is a 9 amino acid peptide mainly produced by the paraventricular nucleus of the hypothalamus. In the periphery vasopressin acts as a neurohormone and stimulates vasoconstriction, glycogenolysis and antidiuresis.

Three vasopressin receptors, all belonging to the class I G-protein coupled receptors, are known. The V1a receptor is expressed in the brain, liver, vascular smooth muscle, lung, uterus and testis, the V1b or V3 receptor is expressed in the brain and pituitary gland, the V2 receptor is expressed in the kidney where it regulates water reabsorption and mediates the antidiuretic effects of vasopressin (Robben, et al. (2006). Am J Physiol Renal Physiol. 291, F257-70, "Cell biological aspects of the vasopressin type-2 receptor and aquaporin 2 water channel in nephrogenic diabetes insipidus"). Compounds with activity at the V2 receptor can therefore cause side-effects on blood homeostasis.

The oxytocin receptor is related to the Vasopressin receptor family and mediates the effects of the neurohormone oxytocin in the brain and the periphery. Oxytocin is believed to have central anxiolytic effects (Neumann (2008). J Neuroendocrinol. 20, 858-65, "Brain oxytocin: a key regulator of emotional and social behaviors in both females and males"). Central oxytocin receptor antagonism might therefore lead to anxiogenic effects, which are regarded as undesired side-effects.

In the brain vasopressin acts as a neuromodulator and is elevated in the amygdala during stress (Ebner, et al. (2002). Eur J Neurosci. 15, 384-8, "Forced swimming triggers vasopressin release within the amygdala to modulate stress-coping strategies in rats"). It is known that stressful life events can trigger major depression and anxiety (Kendler, et al. (2003). Arch Gen Psychiatry. 60, 789-96, "Life Event Dimensions of Loss, Humiliation, Entrapment, and Danger in the Prediction of Onsets of Major Depression and Generalized Anxiety") and that both have very high comorbidity, with anxiety often preceding major depression (Regier, et al. (1998). Br J Psychiatry Suppl. 24-8, "Prevalence of anxiety disorders and their comorbidity with mood and addictive disorders"). The V1a receptor is extensively expressed in the brain and particularly in limbic areas like the amygdala, lateral septum and hippocampus which are playing an important role in the regulation of anxiety. Indeed V1a knock-out mice show a reduction in anxious behavior in the plus-maze, open field and light-dark box (Bielsky, et al. (2004). Neuropsychopharmacology. 29, 483-93, "Profound impairment in social recognition and reduction in anxiety-like behavior in vasopressin V1a receptor knockout mice"). The downregulation of the V1a receptor using antisense oligonucleotide injection in the septum also causes a reduction in anxious behavior (Landgraf, et al. (1995). Regul Pept. 59, 229-39, "V1 vasopressin receptor antisense oligodeoxynucleotide into septum reduces vasopressin binding, social discrimination abilities, and anxiety-related behavior in rats"). Vasopressin or the V1a receptor are also implicated in other neuropsychological disorders: genetic studies recently linked sequence polymorphism in the promoter of the human V1a receptor to autistic spectrum disorders (Yirmiya, et al. (2006). 11, 488-94, "Association between the arginine vasopressin 1a receptor (AVPR1a) gene and autism in a family-based study: mediation by socialization skills"), intranasal administration of vasopressin was shown to influence aggression in human males (Thompson, et al. (2004). Psychoneuroendocrinology. 29, 35-48, "The effects of vasopressin on human facial responses related to social communication") and vasopressin levels were found to be elevated in schizophrenic patients (Raskind, et al. (1987). Biol Psychiatry. 22, 453-62, "Antipsychotic drugs and plasma vasopressin in normals and acute schizophrenic patients") and patients with obsessive-compulsive disorder (Altemus, et al. (1992). Arch Gen Psychiatry. 49, 9-20, "Abnormalities in the regulation of vasopressin and corticotropin releasing factor secretion in obsessive-compulsive disorder").

The V1a receptor is also mediating the cardiovascular effects of vasopressin in the brain by centrally regulating blood pressure and heart rate in the solitary tract nucleus (Michelini and Morris (1999). Ann N Y Acad. Sci. 897, 198-211, "Endogenous vasopressin modulates the cardiovascular responses to exercise"). In the periphery it induces the contraction of vascular smooth muscles and chronic inhibition of the V1a receptor improves hemodynamic parameters in myocardial infarcted rats (Van Kerckhoven, et al. (2002). Eur J Pharmacol. 449, 135-41, "Chronic vasopressin V(1A) but not V(2) receptor antagonism prevents heart failure in chronically infarcted rats"). Hence, V1a antagonists with improved penetration through the blood-brain barrier are expected to be of advantage.

A vasopressin V1a receptor antagonist was shown to be effective in reducing dysmenorrhea in the clinic (Brouard, et al. (2000). Bjog. 107, 614-9, "Effect of SR49059, an orally active V1a vasopressin receptor antagonist, in the prevention of dysmenorrhea"). V1a receptor antagonism has also been implicated in the treatment of female sexual dysfunction (Aughton, et al. (2008). Br J Pharmacol. doi:10.1038/bjp.2008.253, "Pharmacological profiling of neuropeptides on rabbit vaginal wall and vaginal artery smooth muscle in vitro"). In a recent study V1a receptor antagonists were suggested to have a therapeutic role in both erectile dysfunction and premature ejaculation (Gupta, et al. (2008). Br J Pharmacol. 155, 118-26, "Oxytocin-induced contractions within rat and rabbit ejaculatory tissues are mediated by vasopressin V(1A) receptors and not oxytocin receptors").

FIELD OF THE INVENTION

The present invention is concerned with heteroaryl-cyclohexyl-tetraazabenzo[e]azulenes, which act as V1a receptor modulators, and in particular as V1a receptor antagonists, their manufacture, pharmaceutical compositions containing them and their use as medicaments.

SUMMARY OF THE INVENTION

The present invention provides compounds of formula I useful for acting peripherally and centrally in the conditions of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior.

In particular, the present invention is concerned with compounds of formula I

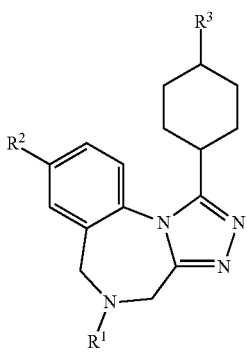

wherein R¹, R² and R³ are as described in herein.

DETAILED DESCRIPTION OF THE INVENTION

The present invention provides compounds which act as V1a receptor modulators, and in particular as V1a receptor antagonists. The invention further provides selective inhibitors of the V1a receptor since it is expected that selectivity affords a low potential to cause unwanted off-target related side effects such as discussed above.

Such V1a antagonists are useful as therapeutics acting peripherally and centrally in the conditions of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior. Particular indications with regard to the present invention are the treatment of anxiety, depressive disorders, obsessive compulsive disorder, autistic spectrum disorders, schizophrenia, and aggressive behavior.

The V1a activity can be detected as described in the experimental section.

The following definitions of the general terms used in the present description apply irrespective of whether the terms in question appear alone or in combination.

As used herein, the terms "$C_{1-6}$alkyl", alone or in combination with other groups, stands for a hydrocarbon radical that is linear or branched, with single or multiple branching, wherein the alkyl group contains 1 to 6 carbon atoms, for example, methyl (Me), ethyl (Et), propyl, isopropyl (i-propyl), n-butyl, i-butyl (iso-butyl), 2-butyl (sec-butyl), t-butyl (tert-butyl) and the like. Particular alkyl groups are groups with 1 to 4 carbon atoms. More particular are methyl, ethyl and isopropyl.

The term "$C_{1-6}$alkoxy", alone or in combination with other groups, denotes a group —O—R' wherein R' is $C_{1-6}$alkyl as defined above, for example methoxy, ethoxy, propoxy, tert-butoxy and the like. Particular alkoxy groups are groups with 1 to 4 carbon atoms. Most particular is methoxy.

The term "6-membered heteroaryl ring", alone or in combination with other groups, refers to a monocyclic aromatic group having a single 6 membered ring, and containing 1, 2 or 3 heteroatoms independently selected from O, S and N. Particular single 6 membered heteroaryl rings have 1 or 2 N. Examples include pyridinyl, pyrimidinyl, pyrazinyl, pyridazinyl, thiazinyl, oxazinyl and the like. Particular single 6-membered rings are pyridinyl, pyrimidinyl, pyrazinyl and pyridazinyl. Specific "6-membered heteroaryl ring" are attached via a carbon atom to the cyclohexyl-moiety. Examples are pyridine-2-yl, pyridine-3-yl, pyrimidin-2-yl, pyrimidin-4-yl, pyrazin-2-yl, pyridazin-2-yl and pyridazin-3-yl.

The term "cycloalkyl" refers to a 3 to 8 membered aliphatic carbon ring, for example cyclopropyl, cyclobutyl, cyclopentyl, cyclohexyl, cycloheptyl or cyclooctyl. Particular are cycloalkyl groups having a 3, 4, 5 or 6 membered carbon ring. Specific is cyclobutyl.

The term "heterocyclyl" refers to a 3 to 7-membered heterocyclic ring containing at least one heteroatom, such as N, O or S, the number of N atoms being 0, 1, 2 or 3 and the number of O and S atoms each being 0, 1 or 2. Examples of heterocyclyl groups include pyrrolidinyl, tetrahydrofuryl, tetrahydrothienyl, tetrahydropyridinyl, tetrahydropyryl, azetidinyl, thiazolidinyl, oxazolidinyl, piperidinyl, morpholinyl, thiomorpholinyl, piperazinyl, azepanyl, diazepanyl, oxazepanyl and the like.

The term "cyano" denotes the group —CN.
The term "hydroxy" denotes the group —OH.
The term "oxo" denotes the group =O.
The term "Boc" denotes the group —C(O)OC(CH₃)₃.
The term "S(O)₂—$C_{1-6}$-alkyl" refers to an "$C_{1-6}$-alkyl" as defined herein linked via an —S(O)₂—.
The term "C(O)—$C_{1-6}$-alkyl" refers to an "$C_{1-6}$-alkyl" as defined herein linked via an —C(=O)—.
The term "C(O)O—$C_{1-6}$-alkyl" refers to an "$C_{1-6}$-alkyl" as defined herein linked via an —C(=O)O—.

The term "halogen", alone or in combination with other groups, denotes chloro (Cl), iodo (I), fluoro (F) and bromo (Br). Particular halogens are F and Cl. Specific is Cl.

The term "halogen-$C_{1-6}$alkyl", alone or in combination with other groups, refers to a $C_{1-6}$alkyl group as defined above substituted by one or multiple halogen, in particular F (i.e. fluoro-$C_{1-6}$alkyl), for example the following groups: CF₃, CHF₂, CH₂F, CH₂CF₃, CH₂CH₂CF₃, CF₂CHF₂, and the like. Particular is CF₃.

The term "hydroxy-$C_{1-6}$alkyl", alone or in combination with other groups, refers to a $C_{1-6}$alkyl group as defined above substituted by one or multiple hydroxy, for example the following groups: —CH₂OH, —CH₂CH₂OH, and the like. Particular is —CH₂CH₂OH.

The term "halogen-$C_{1-6}$alkoxy", alone or in combination with other groups, refers to a $C_{1-6}$alkoxy group as defined above substituted by one or multiple halogen as defined herein, in particular F (i.e. fluoro-$C_{1-6}$alkoxy), for example the following group: CF₃—CH₂—O—.

The term "pharmaceutically acceptable salt" refers to salts that are suitable for use in contact with the tissues of humans and animals without undue toxicity, irritation, allergic response, and the like. Examples of suitable salts with inorganic and organic acids are, but are not limited to, hydrochloric acid, nitric acid, sulphuric acid, phosphoric acid, sulphuric acid, citric acid, formic acid, fumaric acid, maleic acid, lactic acid, malic acid, acetic acid, succinic acid, tartaric acid, methane-sulfonic acid, p-toluenesulphonic acid, trifluoroacetic acid and the like. Particular are hydrochloric acid and formic acid. Specific "pharmaceutically acceptable salts" are mono-hydrochloride, di-hydrochloride and formate.

The terms "pharmaceutically acceptable carrier" and "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. Particularly it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

The term "inhibitor" denotes a compound which competes with, reduces or prevents the binding of a particular ligand to particular receptor or which reduces or prevents the inhibition of the function of a particular protein.

The term "half maximal inhibitory concentration" ($IC_{50}$) denotes the concentration of a particular compound required for obtaining 50% inhibition of a biological process in vitro. $IC_{50}$ values can be converted logarithmically to $pIC_{50}$ values ($-\log IC_{50}$), in which higher values indicate exponentially greater potency. The $IC_{50}$ value is not an absolute value but depends on experimental conditions e.g. concentrations employed. The $IC_{50}$ value can be converted to an absolute inhibition constant (Ki) using the Cheng-Prusoff equation (Biochem. Pharmacol. (1973) 22:3099). The term "inhibition constant" (Ki) denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values ($-\log$ Ki), in which higher values indicate exponentially greater potency.

The term "as defined herein" and "as described herein" when referring to a variable incorporates by reference the broad definition of the variable as well as preferred, more preferred and most preferred definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

"Therapeutically effective amount" means an amount that is effective to prevent, alleviate or ameliorate symptoms of disease or prolong the survival of the subject being treated.

The following table lists abbreviations used within the present document.

TABLE 1

| abbreviations | |
|---|---|
| $(BOC)_2O$ | di-tert-butyl pyrocarbonate |
| $(COCl)_2$ | oxalyl (di)chloride |
| AcOH | acetic acid |

TABLE 1-continued

| abbreviations | |
|---|---|
| $CH_2Cl_2$ | dichloromethane |
| $((CH_3)_3CCO)_2O$ | trimethylacetic anhydride |
| CuCl | copper(I) chloride |
| DMF | dimethylformamide |
| DMAP | 4-(dimethylamino)-pyridine |
| DMSO | dimethylsulfoxide |
| $(dppf)/PdCl_2$ | [1,1'-Bis(diphenylphosphino)ferrocene]dichloropalladium(II). |
| EDTA | ethylendiamin tetraacetate |
| $EtN_3$ | triethylamine |
| EtOAc | ethyl acetate |
| EtOH | ethanol |
| HATU | 2-(7-aza-1H-benzotriazole-1-yl)-1,1,3,3-tetramethyluronium hexafluorophosphate |
| HEPES | 2-(4-(2-hydroxyethyl)-1-piperazinyl)-ethanesulfonic acid |
| HF-pyridine | pyridine hydrofluoride |
| $H_2O$ | water |
| $H_2SO_4$ | sulphuric acid |
| HPLC | high performance liquid crystallography |
| $KHF_2$ | potassium bifluoride |
| $K_3PO_4$ | potassium phosphate |
| Lawesson's reagent | 2,4-bis-(4-methoxyphenyl)-1,3,2,4-dithiadiphosphetane-2,4-disulfide |
| MeOH | methanol |
| MS | mass spectroscopy |
| $Na_2CO_3$ | sodium carbonate |
| $NaNO_2$ | sodium nitrite |
| NaOEt | sodium ethoxide |
| NaOH | sodium hydroxide |
| n-BuOH | n-butanol |
| NMR | nuclear magnetic resonance |
| $PdCl_2$ | palladium dichloride |
| $Pd(OAc)_2$ | palladium acetate |
| $Pd(PPh)_3$ | tetrakis(triphenylphosphine)palladium(0) |
| $POCl_3$ | phosphorus oxychloride |
| $PtO_2$ | platinum oxide |
| $(PPh)_3$ | triphenylphosphine |
| RNA | ribonucleic acid |
| RT | room temperature |
| RT-PCR | reverse transcription-polymerase chain reaction |
| $SOCl_2$ | thionyl chloride |
| t-BuOK | potassium-tert-butoxide |
| THF | tetrahydrofunran |
| Tris | Tris(hydroxymethyl)-aminomethane |
| $ZnBr_2$ | zinc bromide |

The invention also provides pharmaceutical compositions containing, methods of using, and methods of preparing the aforementioned compounds.

While the present invention has been described with reference to the specific embodiments thereof, it should be understood by those skilled in the art that various changes can be made and equivalents can be substituted without departing from the true spirit and scope of the invention. In addition, many modifications can be made to adapt a particular situation, material, composition of matter, process, process step or steps, to the objective spirit and scope of the present invention. All such modifications are intended to be within the scope of the claims appended hereto. All separate embodiments can be combined.

The compounds of formula I can contain asymmetric carbon atoms. Accordingly, the present invention includes all stereoisomeric forms of the compounds of formula I, including each of the individual stereoisomers and mixtures thereof, i.e. their individual optical isomers and mixtures thereof. Additional asymmetric centers can be present depending upon the nature of the various substituents on the molecule. Each such asymmetric centre will independently produce two optical isomers and it is intended that all of the possible optical isomers and diastereomers in mixtures and as pure or partially purified compounds are included within this invention. The present invention is meant to comprehend all such isomeric forms of these compounds. The independent syntheses of these diastereomers or their chromatographic separations can be achieved as known in the art by appropriate modification of the methodology disclosed herein. Their absolute stereochemistry can be determined by the x-ray crystallography of crystalline products or crystalline intermediates which are derivatized, if necessary, with a reagent containing an asymmetric centre of known absolute configuration. If desired, racemic mixtures of the compounds can be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

This applies in particular to the heteroaryl-head group (HG) of the compounds of formula I, namely

HG wherein at least the carbon atoms 1 and 4 are asymmetric carbon atoms and $R^3$ could further comprise asymmetric carbon atoms. It is to be understood that present invention includes all individual stereoisomers of head groups and mixtures thereof.

In particular, these head groups HG are

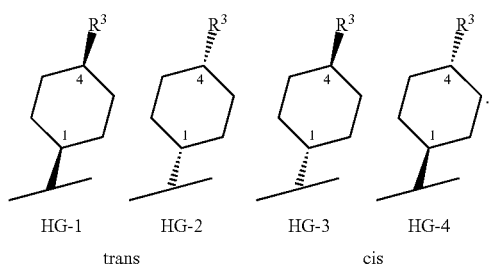

HG-1    HG-2    HG-3    HG-4
  trans              cis

It is further understood that all embodiments of the invention as described herein can be combined with each other.

In detail, the present invention is concerned with compounds of formula I

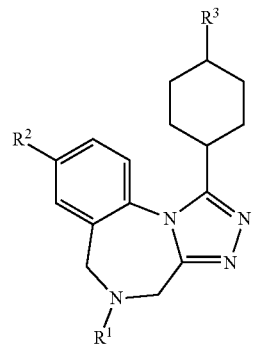

I wherein
$R^1$ is selected from the group consisting of
i) H,
ii) —$C_{1-6}$-alkyl, unsubstituted or substituted by 1 to 5 substituents individually selected from the group consisting of OH, halogen, cyano and $C_{1-6}$-alkoxy,
iii) —$S(O)_2$—$C_{1-6}$-alkyl, wherein the $C_{1-6}$-alkyl is unsubstituted or substituted by 1 to 5 substituents individually selected from the group consisting of OH, halogen, cyano and $C_{1-6}$-alkoxy,
iv) —C(O)—$C_{1-6}$-alkyl, wherein the $C_{1-6}$-alkyl is unsubstituted or substituted by 1 to 5 substituents individually selected from the group consisting of OH, halogen, cyano and $C_{1-6}$-alkoxy,
v) —C(O)O—$C_{1-6}$-alkyl, wherein the $C_{1-6}$-alkyl is unsubstituted or substituted by 1 to 5 substituents individually selected from the group consisting of OH, halogen, cyano and $C_{1-6}$-alkoxy;
vi) cycloalkyl, unsubstituted or substituted by 1 to 5 substituents individually selected from the group consisting of OH, halogen, cyano, $C_{1-6}$-alkyl and $C_{1-6}$-alkoxy;
vii) $S(O)_2$—$(CH_2)_q$—$NR^iR^{ii}$, wherein
q is 0 or 1,
$R^i$ and $R^{ii}$ is each individually selected from the group consisting of H and $C_{1-6}$-alkyl, or $R^i$ and $R^{ii}$ form together with the nitrogen to which they are attached a 3- to 7-membered heterocyclyl containing one or two heteroatoms individually selected from N, O and S, and which heterocyclyl is unsubstituted or substituted by 1 to 5 substituents individually selected from the group consisting of oxo, halogen, $C_{1-6}$-alkyl and $C_{1-6}$-alkoxy,
viii) —$(CH_2)_r$—$NR^{iii}R^{iv}$, wherein
r is 1, 2 or 3,
$R^{iii}$ and $R^{iv}$ is each individually selected from the group consisting of H and $C_{1-6}$-alkyl, or $R^{iii}$ and $R^{iv}$ form together with the nitrogen to which they are attached a 3- to 7-membered heterocyclyl containing one or two heteroatoms individually selected from N, O and S, and which heterocyclyl is unsubstituted or substituted by 1 to 5 substituents individually selected from the group consisting of oxo, halogen, $C_{1-6}$-alkyl and $C_{1-6}$-alkoxy, and
ix) —$C(O)(CH_2)_s$—$NR^vR^{vi}$, wherein
s is 1, 2 or 3,
$R^v$ and $R^{vi}$ is each individually selected from the group consisting of H and $C_{1-6}$-alkyl, or $R^v$ and $R^{vi}$ form together with the nitrogen to which they are attached a 3- to 7-membered heterocyclyl containing one or two heteroatoms individually selected from N, O and S, and which heterocyclyl is unsubstituted or substituted by 1 to 5 substituents individually selected from the group consisting of oxo, halogen, $C_{1-6}$-alkyl and $C_{1-6}$-alkoxy;

$R^2$ is halogen; and
$R^3$ is a 6-membered heteroaryl ring, unsubstituted or substituted by 1 to 5 substituents individually selected from the group consisting of OH, halogen, cyano, $C_{1-6}$-alkyl, $C_{1-6}$-alkoxy, halogen-$C_{1-6}$-alkyl, halogen-$C_{1-6}$-alkoxy and hydroxy-$C_{1-6}$-alkyl;
or a pharmaceutically acceptable salt thereof.

A certain embodiment of the invention provides compounds of formula Ia,

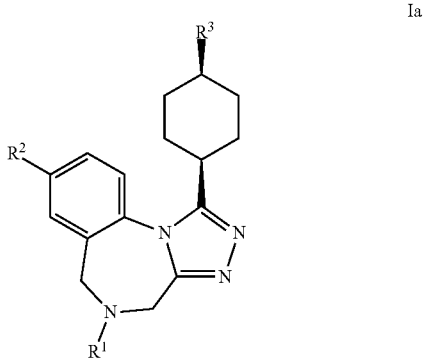

where $R^1$, $R^2$ and $R^3$ are the same as described herein.

A certain embodiment of the invention provides compounds of formula I, where $R^1$ is selected from the group consisting of
i) H,
ii) —$C_{1-6}$-alkyl, unsubstituted or substituted by 1 to 2 substituents individually selected from the group consisting of halogen and $C_{1-6}$-alkoxy,
iii) —$S(O)_2$—$C_{1-6}$-alkyl, wherein the $C_{1-6}$-alkyl is unsubstituted,
iv) —$C(O)$—$C_{1-6}$-alkyl, wherein the $C_{1-6}$-alkyl is unsubstituted or substituted by 1 to 2 OH,
v) —$C(O)O$—$C_{1-6}$-alkyl, wherein the $C_{1-6}$-alkyl is unsubstituted;
vi) unsubstituted cycloalkyl,
vii) $S(O)_2$—$(CH_2)_q$—$NR^iR^{ii}$, wherein q is 0, $R^i$ and $R^{ii}$ is each individually selected from the group consisting of H and $C_{1-6}$-alkyl,
viii) —$(CH_2)_r$—$NR^{iii}R^{iv}$, wherein r is 2, $R^{iii}$ and $R^{iv}$ is each individually selected from the group consisting of H and $C_{1-6}$-alkyl, and
ix) —$C(O)(CH_2)_s$—$NR^vR^{vi}$, wherein s is 1, $R^v$ and $R^{vi}$ is each individually selected from the group consisting of H and $C_{1-6}$-alkyl.

A certain embodiment of the invention provides compounds of formula I, where $R^1$ is selected from the group consisting of
i) H,
ii) —$C_{1-6}$-alkyl, unsubstituted or substituted by 1 to 2 substituents individually selected from the group consisting of halogen and $C_{1-6}$-alkoxy, and
iii) unsubstituted cycloalkyl.

A certain embodiment of the invention provides compounds of formula I, where $R^1$ is selected from the group consisting of H, methyl, ethyl, isopropyl, 2,2-difluoroethyl, 2-methoxy-ethyl and cyclobutyl.

A certain embodiment of the invention provides compounds of formula I, where $R^1$ is selected from the group consisting of Boc, H, methyl, ethyl, isopropyl, cyclobutyl, 2,2-difluoroethyl, 2-methoxyethyl, 2-methylaminoethyl, 1-oxo-ethyl, 1-oxo-2-hydroxy-ethyl, 1-oxo-2-dimethylamino-ethyl, methylsulfonyl and N,N-dimethysulfonamidyl.

A certain embodiment of the invention provides compounds of formula I, where $R^1$ is Boc.

A certain embodiment of the invention provides compounds of formula I, where $R^1$ is H.

A certain embodiment of the invention provides compounds of formula I, where $R^1$ is —$C_{1-6}$-alkyl.

A certain embodiment of the invention provides compounds of formula I, where $R^1$ is methyl.

A certain embodiment of the invention provides compounds of formula I, where $R^1$ is ethyl.

A certain embodiment of the invention provides compounds of formula I, where $R^1$ is isopropyl.

A certain embodiment of the invention provides compounds of formula I, where $R^1$ is cycloalkyl.

A certain embodiment of the invention provides compounds of formula I, where $R^1$ is cyclobutyl.

A certain embodiment of the invention provides compounds of formula I, where $R^1$ is —$C_{1-6}$-alkyl, substituted by 2 halogens.

A certain embodiment of the invention provides compounds of formula I, where $R^1$ is 2,2-difluoroethyl.

A certain embodiment of the invention provides compounds of formula I, where $R^1$ is —$C_{1-6}$-alkyl, substituted by $C_{1-6}$-alkoxy.

A certain embodiment of the invention provides compounds of formula I, where $R^1$ is 2-methoxyethyl.

A certain embodiment of the invention provides compounds of formula I, where $R^1$ is —$(CH_2)_r$—$NR^{iii}R^{iv}$, wherein r is 2, and $R^{iii}$ and $R^{iv}$ is each individually selected from the group consisting of H and $C_{1-6}$-alkyl.

A certain embodiment of the invention provides compounds of formula I, where $R^1$ is 2-methylaminoethyl.

A certain embodiment of the invention provides compounds of formula I, where $R^1$ is —$C(O)$—$C_{1-6}$-alkyl, wherein the $C_{1-6}$-alkyl is unsubstituted or substituted by 1 to 2 OH A certain embodiment of the invention provides compounds of formula I, where $R^1$ is t-oxo-ethyl.

A certain embodiment of the invention provides compounds of formula I, where $R^1$ is 1-oxo-2-hydroxy-ethyl.

A certain embodiment of the invention provides compounds of formula I, where $R^1$ is —$C(O)(CH_2)_n$—$NR^vR^{vi}$, wherein s is 1, and $R^v$ and $R^{vi}$ is each individually selected from the group consisting of H and $C_{1-6}$-alkyl.

A certain embodiment of the invention provides compounds of formula I, where $R^1$ is 1-oxo-2-dimethylaminoethyl.

A certain embodiment of the invention provides compounds of formula I, where $R^1$ is $S(O)_2$—$C_{1-6}$-alkyl.

A certain embodiment of the invention provides compounds of formula I, where $R^1$ is methylsulfonyl.

A certain embodiment of the invention provides compounds of formula I, where $R^1$ is $S(O)_2$—$CH_2)_q$—$NR^iR^{ii}$, wherein q is 0, and $R^i$ and $R^{ii}$ is each individually selected from the group consisting of H and $C_{1-6}$-alkyl.

A certain embodiment of the invention provides compounds of formula I, where $R^1$ is N,N-dimethysulfonamidyl.

A certain embodiment of the invention provides compounds of formula I, where $R^2$ is chloro.

A certain embodiment of the invention provides compounds of formula I, where $R^2$ is fluoro.

A certain embodiment of the invention provides compounds of formula I, where $R^3$ is selected from the group consisting of i) pyridinyl, unsubstituted or substituted by 1 to 2 substituents individually selected from the group consisting of halogen, $C_{1-6}$-alkyl and $C_{1-6}$-alkoxy,
ii) pyrazinyl, unsubstituted or substituted by 1 to $C_{1-6}$-alkyl,
iii) unsubstituted pyridazinyl, and
iv) pyrimidinyl, unsubstituted or substituted by 1 to 2 $C_{1-6}$-alkyl.

A certain embodiment of the invention provides compounds of formula I, where $R^3$ is
i) pyridinyl, unsubstituted or substituted by 1 to 2 substituents individually selected from the group consisting of halogen and $C_{1-6}$-alkyl, or
ii) unsubstituted pyrazinyl.

A certain embodiment of the invention provides compounds of formula I, where $R^3$ is selected from the group consisting of pyridin-2-yl, 6-methyl-pyridin-2-yl, 3-chloro-pyridin-2-yl, 3,5-difluoro-pyridin-2-yl, 6-chloro-pyridin-2-yl, 5-fluoro-pyridin-2-yl, 3-fluoro-pyridin-2-yl and pyrazin-2-yl.

A certain embodiment of the invention provides compounds of formula I, where $R^3$ is selected from the group consisting of pyridin-2-yl, 6-methyl-pyridin-2-yl, 6-chloro-pyridin-2-yl, 5-fluoro-pyridin-2-yl, 3-fluoro-pyridin-2-yl and pyrazin-2-yl.

A certain embodiment of the invention provides compounds of formula I, where $R^3$ is pyridinyl, unsubstituted or substituted by 1 to 2 substituents individually selected from the group consisting of halogen, $C_{1-6}$-alkyl and $C_{1-6}$-alkoxy.

A certain embodiment of the invention provides compounds of formula I, where $R^3$ is pyridin-2-yl.
A certain embodiment of the invention provides compounds of formula I, where $R^3$ is 6-methyl-pyridin-2-yl.

A certain embodiment of the invention provides compounds of formula I, where $R^3$ is 6-ethyl-pyridin-2-yl.

A certain embodiment of the invention provides compounds of formula I, where $R^3$ is 6-isopropyl-pyridin-2-yl.

A certain embodiment of the invention provides compounds of formula I, where $R^3$ is 6-methoxy-pyridin-2-yl.

A certain embodiment of the invention provides compounds of formula I, where $R^3$ is 3-chloro-pyridin-2-yl.

A certain embodiment of the invention provides compounds of formula I, where $R^3$ is 6-chloro-pyridin-2-yl.

A certain embodiment of the invention provides compounds of formula I, where $R^3$ is 6-fluoro-pyridin-2-yl.

A certain embodiment of the invention provides compounds of formula I, where $R^3$ is 5-fluoro-pyridin-2-yl.

A certain embodiment of the invention provides compounds of formula I, where $R^3$ is 4-chloro-pyridin-2-yl.

A certain embodiment of the invention provides compounds of formula I, where $R^3$ is 3-fluoro-pyridin-2-yl.

A certain embodiment of the invention provides compounds of formula I, where $R^3$ is 3,5-difluoro-pyridin-2-yl.

A certain embodiment of the invention provides compounds of formula I, where $R^3$ is pyridin-3-yl.

A certain embodiment of the invention provides compounds of formula I, where $R^3$ is 2-chloro-pyridin-3-yl.

A certain embodiment of the invention provides compounds of formula I, where $R^3$ is pyrazinyl, unsubstituted or substituted by 1 to 2 $C_{1-6}$-alkyl.

A certain embodiment of the invention provides compounds of formula I, where $R^3$ is pyrazin-2-yl.

A certain embodiment of the invention provides compounds of formula I, where $R^3$ is 6-methyl-pyrazin-2-yl.

A certain embodiment of the invention provides compounds of formula I, where $R^3$ is -methyl-pyrazin-2-yl.

A certain embodiment of the invention provides compounds of formula I, where $R^3$ is 3,6-dimethyl-pyrazin-2-yl.

A certain embodiment of the invention provides compounds of formula I, where $R^3$ is pyridazinyl.

A certain embodiment of the invention provides compounds of formula I, where $R^3$ is pyridazin-3-yl.

A certain embodiment of the invention provides compounds of formula I, where $R^3$ is pyrimidinyl, unsubstituted or substituted by 1 to 2 $C_{1-6}$-alkyl.

A certain embodiment of the invention provides compounds of formula I, where $R^3$ is pyrimidin-2-yl.

A certain embodiment of the invention provides compounds of formula I, where $R^3$ is 4,6-dimethyl-pyrimidin-2-yl.

A certain embodiment of the invention provides compounds of formula I, where $R^3$ is 2-methyl-pyrimidin-4-yl.

A certain embodiment of the invention provides compounds of formula I, where $R^3$ is selected from the group consisting of pyridin-2-yl, 6-methyl-pyridin-2-yl, 6-ethyl-pyridin-2-yl, 6-isopropyl-pyridin-2-yl, 6-methoxy-pyridin-2-yl, 6-chloro-pyridin-2-yl, 6-fluoro-pyridin-2-yl, 5-fluoro-pyridin-2-yl, 4-chloro-pyridin-2-yl, 3-fluoro-pyridin-2-yl, pyridin-3-yl, 2-chloro-pyridin-3-yl, 2-fluoro-pyridin-3-yl, pyrimidin-2-yl, 4,6-dimethyl-pyrimidin-2-yl, 2-methyl-pyrimidin-4-yl, pyrazin-2-yl, 6-methyl-pyrazin-2-yl, 3-methyl-pyrazin-2-yl, 3,6-dimethyl-pyrazin-2-yl and pyridazin-3-yl.

Examples for the compound according to the invention are shown in the experimental section and the table below.

TABLE 2

| structures of selected examples | |
|---|---|
| Ex | Structure |
| 1 | 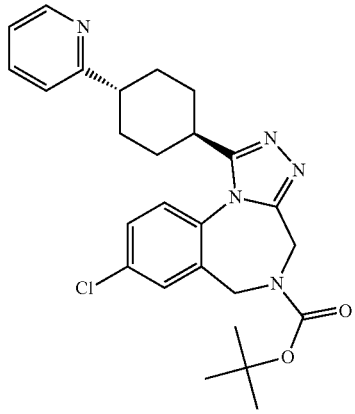 |
| 2 | ClH 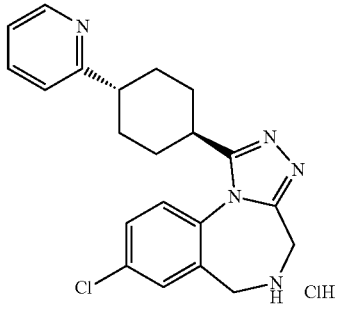 ClH |

TABLE 2-continued
structures of selected examples
| Ex | Structure |
|---|---|
| 3 | 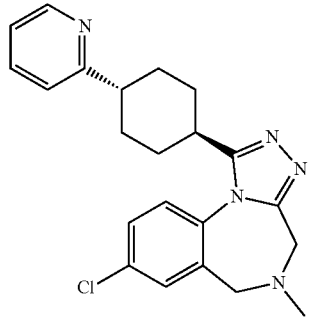 [SMILES: CN1Cc2cc(Cl)ccc2-n2c(nnc2[C@H]2CC[C@H](c3ccccn3)CC2)C1] |
| 4 | 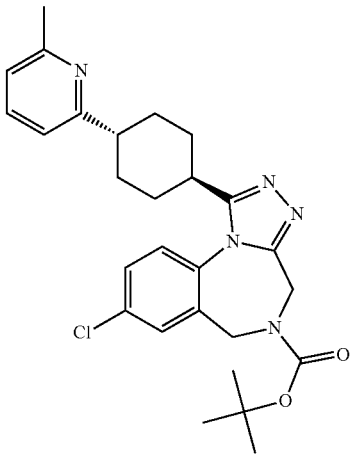 [SMILES: Cc1cccc([C@H]2CC[C@H](c3nnc4n3-c3ccc(Cl)cc3CN(C(=O)OC(C)(C)C)C4)CC2)n1] |
| 5 | 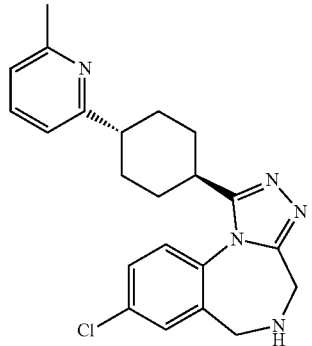 [SMILES: Cc1cccc([C@H]2CC[C@H](c3nnc4n3-c3ccc(Cl)cc3CNC4)CC2)n1] |
| 6 | 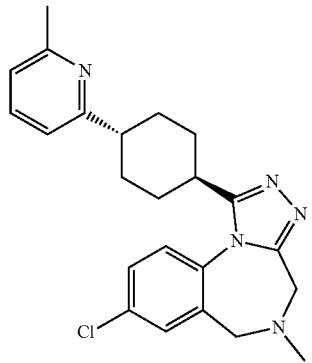 [SMILES: Cc1cccc([C@H]2CC[C@H](c3nnc4n3-c3ccc(Cl)cc3CN(C)C4)CC2)n1] |
TABLE 2-continued
structures of selected examples
| Ex | Structure |
|---|---|
| 7 | 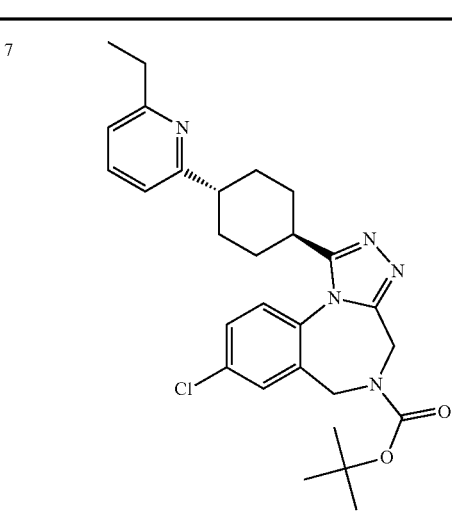 |
| 8 | 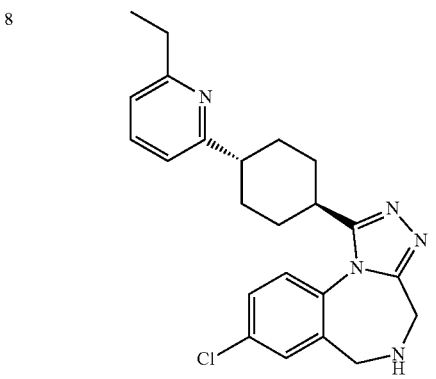 |
| 9 | 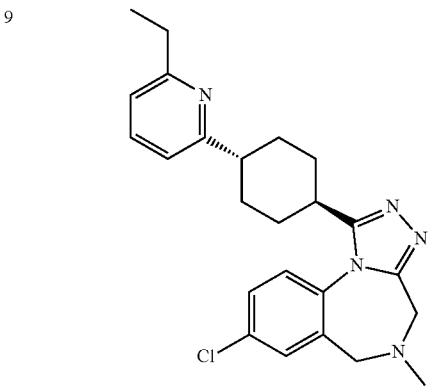 |

TABLE 2-continued
structures of selected examples
| Ex | Structure |
|---|---|
| 10 | 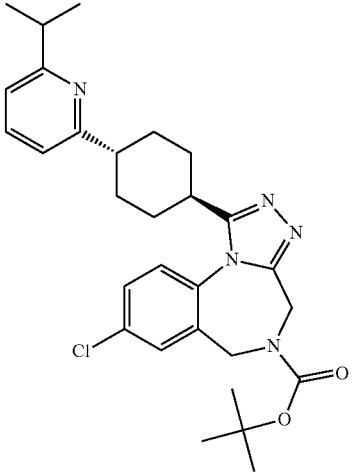 [SMILES: CC(C)c1cccc([C@H]2CC[C@H](c3nnc4n3-c3ccc(Cl)cc3CN(C(=O)OC(C)(C)C)C4)CC2)n1] |
| 11 | 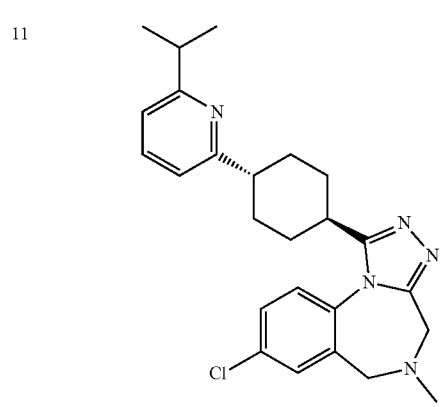 |
| 12 | 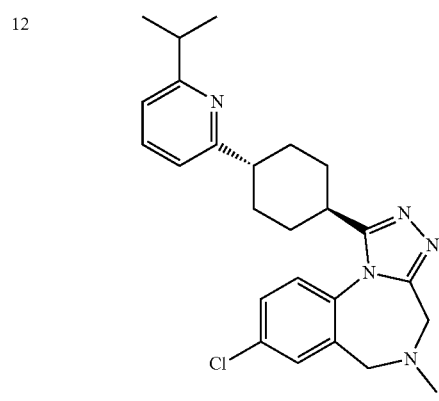 |
| 13 | 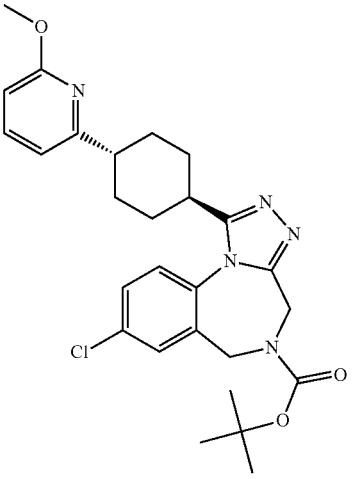 [SMILES: COc1cccc([C@H]2CC[C@H](c3nnc4n3-c3ccc(Cl)cc3CN(C(=O)OC(C)(C)C)C4)CC2)n1] |
| 14 | 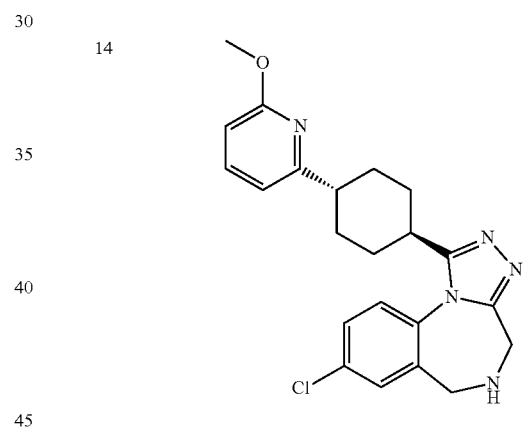 |
| 15 | 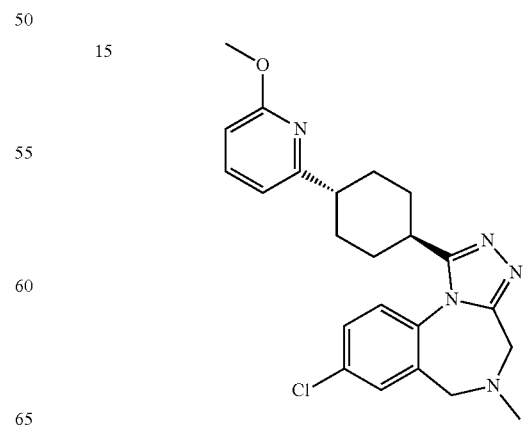 |

TABLE 2-continued
structures of selected examples
| Ex | Structure |
|----|-----------|
| 16 | 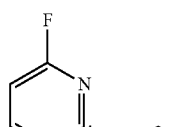 |
| 17 | 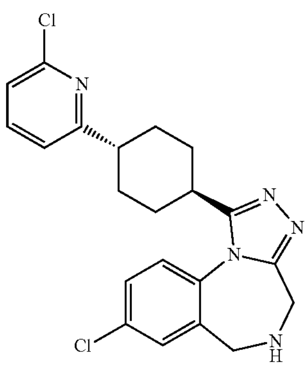 [SMILES: Clc1ccc2c(c1)CNCc1nnc([C@H]3CC[C@H](c4cccc(Cl)n4)CC3)n1-2] |
| 18 | 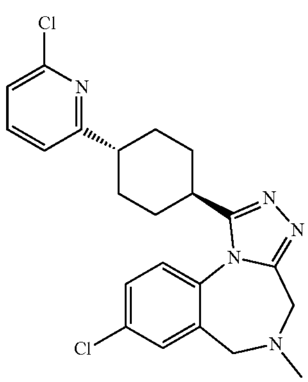 [SMILES: CN1Cc2cc(Cl)ccc2-n2c(nnc2[C@H]2CC[C@H](c3cccc(Cl)n3)CC2)C1] |
TABLE 2-continued
structures of selected examples
| Ex | Structure |
|----|-----------|
| 19 | 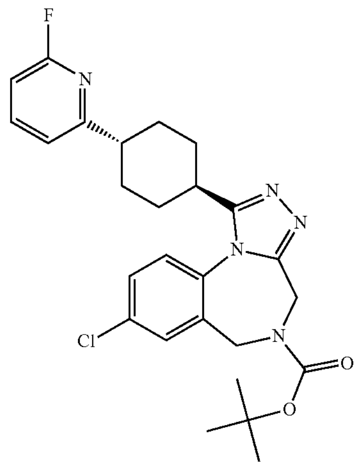 [SMILES: CC(C)(C)OC(=O)N1Cc2cc(Cl)ccc2-n2c(nnc2[C@H]2CC[C@H](c3cccc(F)n3)CC2)C1] |
| 20 | 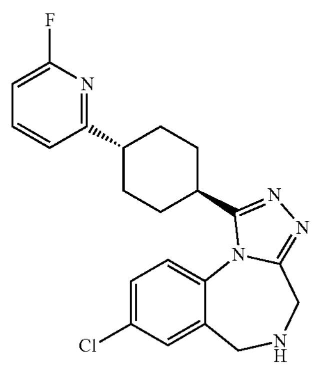 [SMILES: Fc1cccc([C@H]2CC[C@H](c3nnc4n3-c3ccc(Cl)cc3CNC4)CC2)n1] |
| 21 | 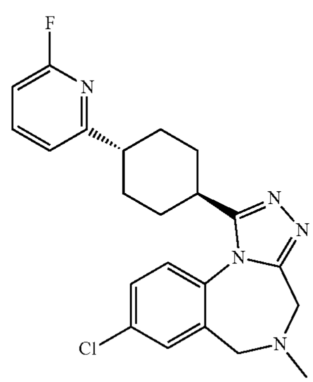 [SMILES: CN1Cc2cc(Cl)ccc2-n2c(nnc2[C@H]2CC[C@H](c3cccc(F)n3)CC2)C1] |

TABLE 2-continued structures of selected examples

| Ex | Structure |
|---|---|
| 22 | (5-fluoropyridin-2-yl cyclohexyl triazolo-chloro-benzodiazepine with N-Boc) |
| 23 | (5-fluoropyridin-2-yl cyclohexyl triazolo-chloro-benzodiazepine, NH·HCl) |
| 24 | (5-fluoropyridin-2-yl cyclohexyl triazolo-chloro-benzodiazepine, N-methyl) |
| 25 | (4-chloropyridin-2-yl cyclohexyl triazolo-chloro-benzodiazepine with N-Boc) |
| 26 | (4-chloropyridin-2-yl cyclohexyl triazolo-chloro-benzodiazepine, NH) |
| 27 | (4-chloropyridin-2-yl cyclohexyl triazolo-chloro-benzodiazepine, N-methyl) |
| 28 | (3-fluoropyridin-2-yl cyclohexyl triazolo-chloro-benzodiazepine with N-Boc) |

TABLE 2-continued structures of selected examples

| Ex | Structure |
|---|---|
| 29 | 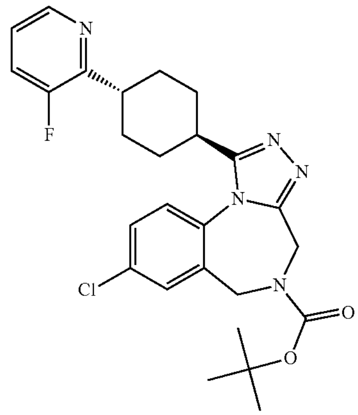 [SMILES: CC(C)(C)OC(=O)N1Cc2cc(Cl)ccc2-n2c(nnc2[C@H]2CC[C@H](c3ncccc3F)CC2)C1] |
| 30 | 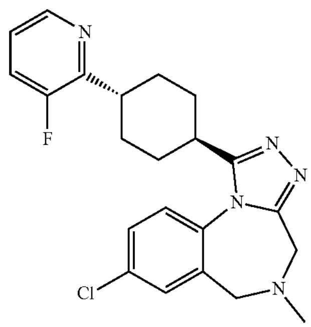 [SMILES: CN1Cc2cc(Cl)ccc2-n2c(nnc2[C@H]2CC[C@H](c3ncccc3F)CC2)C1] |
| 31 | 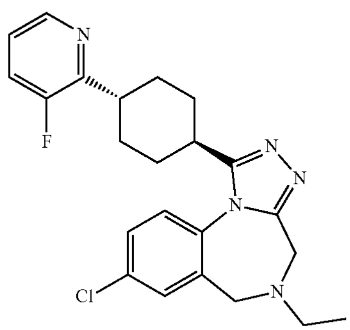 [SMILES: CCN1Cc2cc(Cl)ccc2-n2c(nnc2[C@H]2CC[C@H](c3ncccc3F)CC2)C1] |
| 32 | 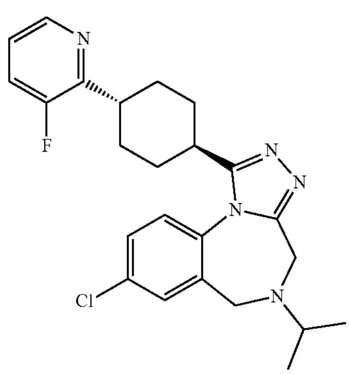 [SMILES: CC(C)N1Cc2cc(Cl)ccc2-n2c(nnc2[C@H]2CC[C@H](c3ncccc3F)CC2)C1] |
| 33 | 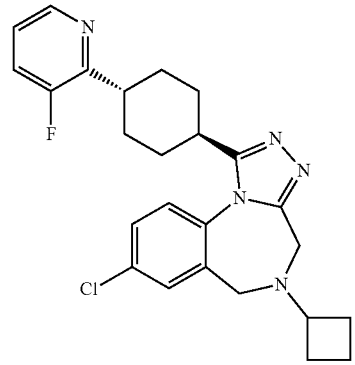 [SMILES: Fc1cccnc1[C@H]1CC[C@H](c2nnc3n2-c2ccc(Cl)cc2CN(C2CCC2)C3)CC1] |
| 34 | 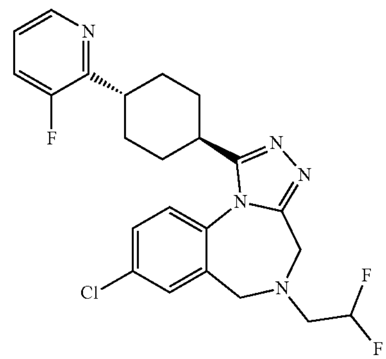 [SMILES: Fc1cccnc1[C@H]1CC[C@H](c2nnc3n2-c2ccc(Cl)cc2CN(CC(F)F)C3)CC1] |
| 35 | 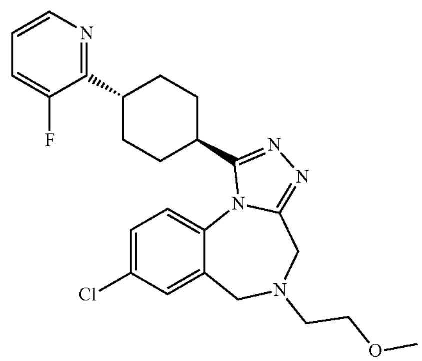 [SMILES: COCCN1Cc2cc(Cl)ccc2-n2c(nnc2[C@H]2CC[C@H](c3ncccc3F)CC2)C1] |
| 36 | 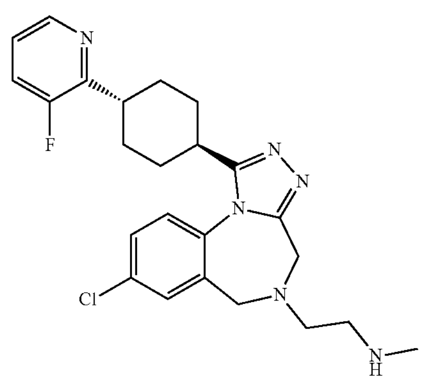 [SMILES: CNCCN1Cc2cc(Cl)ccc2-n2c(nnc2[C@H]2CC[C@H](c3ncccc3F)CC2)C1] |

TABLE 2-continued
structures of selected examples
| Ex | Structure |
|----|-----------|
| 37 | 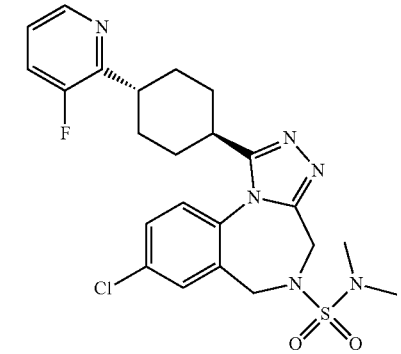 |
| 38 | 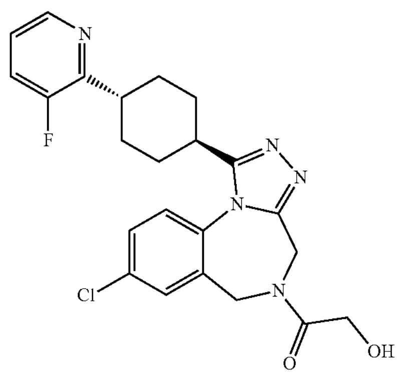 [SMILES: O=C(CO)N1Cc2cc(Cl)ccc2-n2c(nnc2[C@H]2CC[C@H](c3ncccc3F)CC2)C1] |
| 39 | 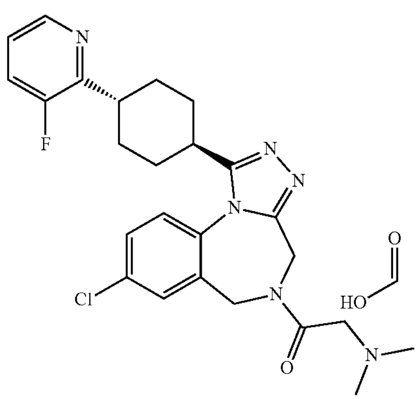 |
| 40 | 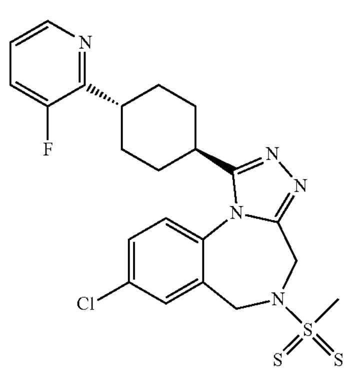 [SMILES: CS(=S)(=S)N1Cc2cc(Cl)ccc2-n2c(nnc2[C@H]2CC[C@H](c3ncccc3F)CC2)C1] |
| 41 | 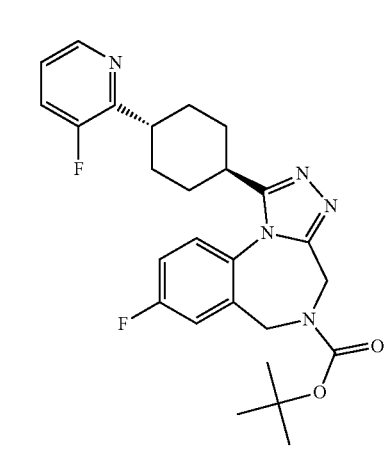 [SMILES: CC(C)(C)OC(=O)N1Cc2cc(F)ccc2-n2c(nnc2[C@H]2CC[C@H](c3ncccc3F)CC2)C1] |
| 42 | |
| 43 | |
| 44 | |

TABLE 2-continued
structures of selected examples
| Ex | Structure |
|----|-----------|
| 45 | 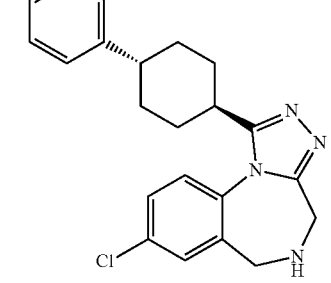 |
| 46 | 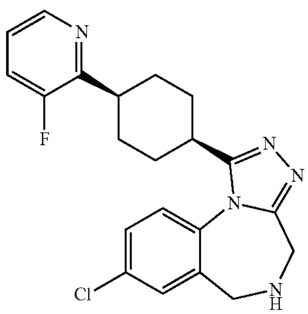 [SMILES: Fc1cccnc1[C@H]1CC[C@@H](c2nnc3n2-c2ccc(Cl)cc2CNC3)CC1] |
| 47 | 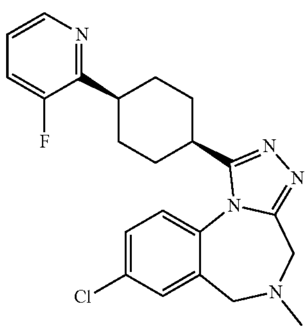 [SMILES: CN1Cc2cc(Cl)ccc2-n2c(nnc2[C@H]2CC[C@@H](c3ncccc3F)CC2)C1] |
| 48 | 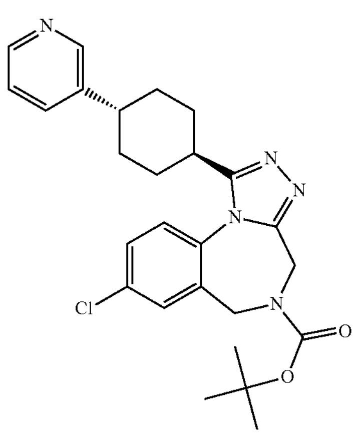 [SMILES: CC(C)(C)OC(=O)N1Cc2cc(Cl)ccc2-n2c(nnc2[C@H]2CC[C@H](c3cccnc3)CC2)C1] |
TABLE 2-continued
structures of selected examples
| Ex | Structure |
|----|-----------|
| 49 | 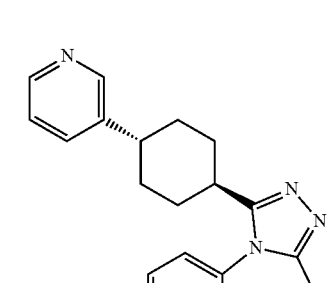 |
| 50 | 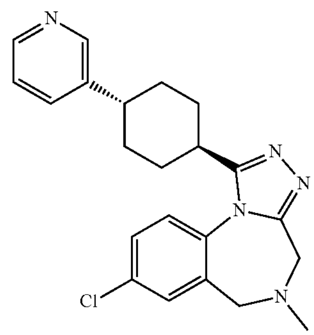 [SMILES: CN1Cc2cc(Cl)ccc2-n2c(nnc2[C@H]2CC[C@H](c3cccnc3)CC2)C1] |
| 51 | 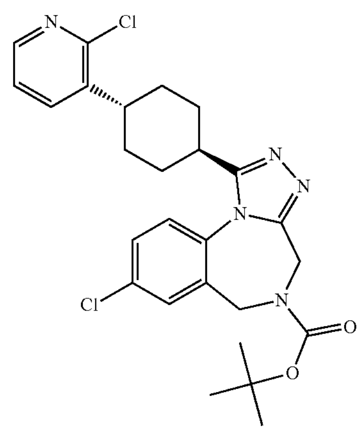 |
| 52 | 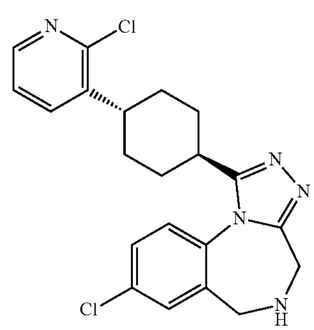 [SMILES: Clc1ccc2c(c1)CNCc1nnc([C@H]3CC[C@H](c4cccnc4Cl)CC3)n1-2] |

TABLE 2-continued structures of selected examples

| Ex | Structure |
|---|---|
| 53 | (2-chloropyridin-3-yl cyclohexyl triazolo-benzodiazepine with Cl and N-methyl) |
| 54 | (2-fluoropyridin-3-yl cyclohexyl triazolo-benzodiazepine with Cl and N-Boc) |
| 55 | (2-fluoropyridin-3-yl cyclohexyl triazolo-benzodiazepine with Cl and NH) |
| 56 | (2-fluoropyridin-3-yl cyclohexyl triazolo-benzodiazepine with Cl and N-methyl) |
| 57 | (pyrimidin-2-yl cyclohexyl triazolo-benzodiazepine with Cl and N-Boc) |
| 58 | (pyrimidin-2-yl cyclohexyl triazolo-benzodiazepine with Cl and N-Boc) |
| 59 | (pyrimidin-2-yl cyclohexyl triazolo-benzodiazepine with Cl and NH) |
| 60 | (pyrimidin-2-yl cyclohexyl triazolo-benzodiazepine with Cl and N-methyl) |

TABLE 2-continued structures of selected examples

| Ex | Structure |
|---|---|
| 61 | (structure) |
| 62 | (structure) |
| 63 | (structure) |
| 64 | (structure) |
| 65 | (structure) |
| 66 | (structure) |
| 67 | (structure) |
| 68 | (structure) |

TABLE 2-continued structures of selected examples

| Ex | Structure |
|---|---|
| 69 | 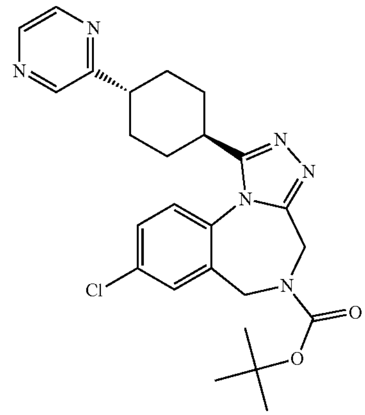 [SMILES: CC(C)(C)OC(=O)N1Cc2cc(Cl)ccc2-n2c(nnc2[C@H]2CC[C@H](c3cnccn3)CC2)C1] |
| 70 | 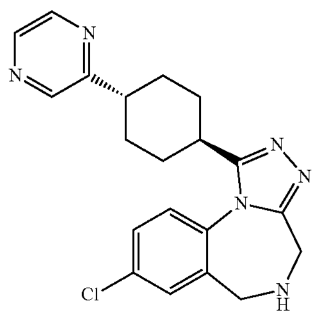 [SMILES: Clc1ccc2c(c1)CNCc1nnc([C@H]3CC[C@H](c4cnccn4)CC3)n1-2] |
| 71 | 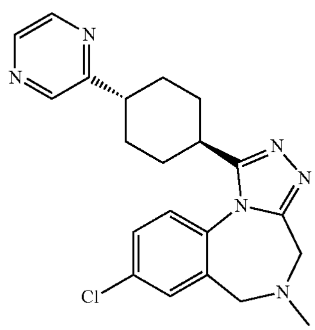 [SMILES: CN1Cc2cc(Cl)ccc2-n2c(nnc2[C@H]2CC[C@H](c3cnccn3)CC2)C1] |
| 72 | 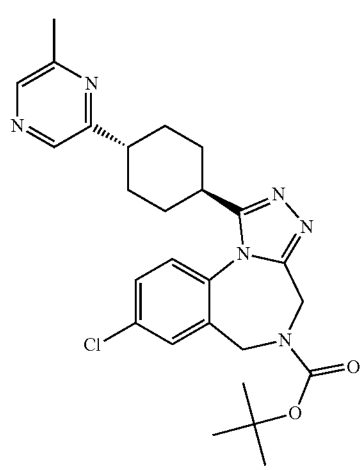 [SMILES: Cc1cncc([C@H]2CC[C@H](c3nnc4n3-c3ccc(Cl)cc3CN(C(=O)OC(C)(C)C)C4)CC2)n1] |
| 73 | |
| 74 | |
| 75 | |
| 76 | |

TABLE 2-continued structures of selected examples

| Ex | Structure |
|---|---|
| 77 | 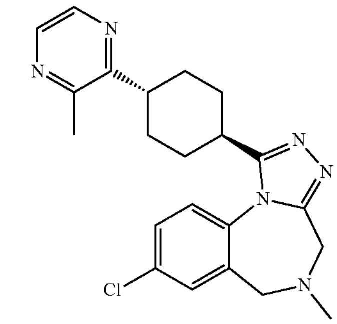 [SMILES: Cc1nccnc1[C@H]1CC[C@H](c2nnc3n2-c2ccc(Cl)cc2CN(C)C3)CC1] |
| 78 | 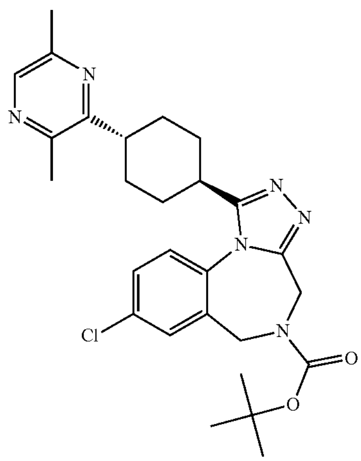 [SMILES: Cc1cnc(C)c([C@H]2CC[C@H](c3nnc4n3-c3ccc(Cl)cc3CN(C(=O)OC(C)(C)C)C4)CC2)n1] |
| 79 | 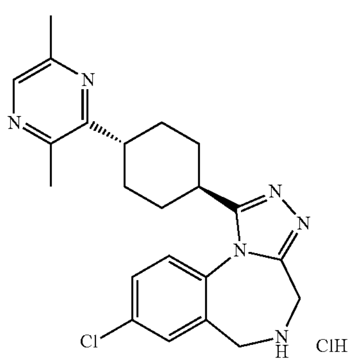 [SMILES: Cc1cnc(C)c([C@H]2CC[C@H](c3nnc4n3-c3ccc(Cl)cc3CNC4)CC2)n1 ; Cl] |
| 80 | 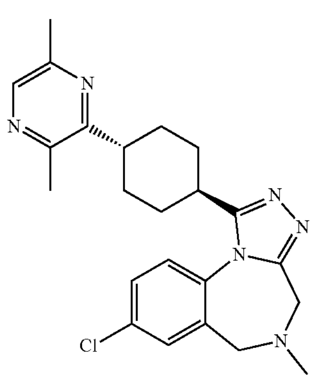 [SMILES: Cc1cnc(C)c([C@H]2CC[C@H](c3nnc4n3-c3ccc(Cl)cc3CN(C)C4)CC2)n1] |
| 81 | |
| 82 | |
| 83 | |
| 84 | |

TABLE 2-continued structures of selected examples

| Ex | Structure |
|---|---|
| 85 | 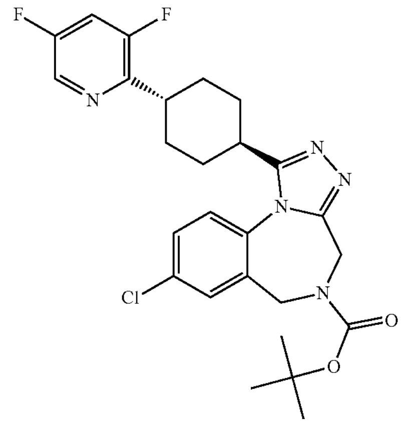 [SMILES: CC(C)(C)OC(=O)N1Cc2cc(Cl)ccc2-n2c(nnc2[C@H]2CC[C@H](c3ncc(F)cc3F)CC2)C1] |
| 86 | 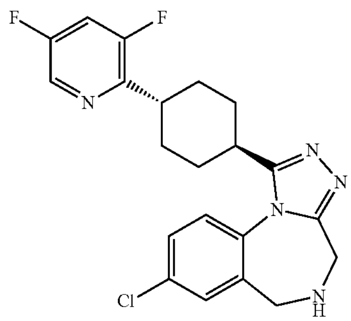 [SMILES: Fc1cnc([C@H]2CC[C@H](c3nnc4n3-c3ccc(Cl)cc3CNC4)CC2)c(F)c1] |
| 87 | 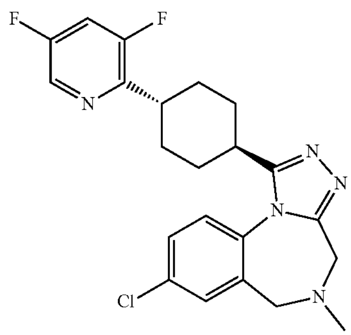 [SMILES: CN1Cc2cc(Cl)ccc2-n2c(nnc2[C@H]2CC[C@H](c3ncc(F)cc3F)CC2)C1] |

Specific compounds of the invention are shown in the examples. A certain embodiment of the invention relates to compounds selected from the group consisting of
trans-8-Chloro-1-(4-pyridin-2-yl-cyclohexyl)-4H,6H-2,3,5,10b-tetraaza-benzo[e]azulene-5-carboxylic acid tert-butyl ester,
cis-8-Chloro-1-(4-pyrimidin-2-yl-cyclohexyl)-4H,6H-2,3,5,10b-tetraaza-benzo[e]azulene-5-carboxylic acid tert-butyl ester,
trans-8-Chloro-1-(4-pyrimidin-2-yl-cyclohexyl)-4H,6H-2,3,5,10b-tetraaza-benzo[e]azulene-5-carboxylic acid tert-butyl ester,
trans-8-Chloro-1-(4-pyrimidin-2-yl-cyclohexyl)-5,6-dihydro-4H-2,3,5,10b-tetraaza-benzo[e]azulene,
trans-8-Chloro-5-methyl-1-(4-pyrimidin-2-yl-cyclohexyl)-5,6-dihydro-4H-2,3,5,10b-tetraaza-benzo[e]azulene,
1-(trans-8-chloro-1-((1R,4S)-4-(3-fluoropyridin-2-yl)cyclohexyl)-4H-benzo[e][1,2,4]triazolo[4,3-a][1,4]diazepin-5(6H)-yl)ethanone,
1-(trans-8-chloro-1-((1R,4S)-4-(3-fluoropyridin-2-yl)cyclohexyl)-4H-benzo[e][1,2,4]triazolo[4,3-a][1,4]diazepin-5(6H)-yl)-2-hydroxyethanone,
1-(trans-8-chloro-1-((1R,4S)-4-(3-fluoropyridin-2-yl)cyclohexyl)-4H-benzo[e][1,2,4]triazolo[4,3-a][1,4]diazepin-5(6H)-yl)-2-(dimethylamino)ethanone formate,
2-(trans-8-chloro-1-((1R,4S)-4-(3-fluoropyridin-2-yl)cyclohexyl)-4H-benzo[e][1,2,4]triazolo[4,3-a][1,4]diazepin-5(6H)-yl)-N-methylethanamine,
trans-8-Chloro-1-[4-(3,5-difluoro-pyridin-2-yl)-cyclohexyl]-4H,6H-2,3,5,10b-tetraaza-benzo[e]azulene-5-carboxylic acid tert-butyl ester,
trans-8-Chloro-1-[4-(3,5-difluoro-pyridin-2-yl)-cyclohexyl]-5,6-dihydro-4H-2,3,5,10b-tetraaza-benzo[e]azulene,
trans-8-Chloro-1-[4-(3,5-difluoro-pyridin-2-yl)-cyclohexyl]-5-methyl-5,6-dihydro-4H-2,3,5,10b-tetraaza-benzo[e]azulene,
trans-8-Chloro-1-[4-(3-chloro-pyridin-2-yl)-cyclohexyl]-5-methyl-5,6-dihydro-4H-2,3,5,10b-tetraaza-benzo[e]azulene,
trans-8-Chloro-1-[4-(3-chloro-pyridin-2-yl)-cyclohexyl]-4H,6H-2,3,5,10b-tetraaza-benzo[e]azulene-5-carboxylic acid tert-butyl ester,
trans-8-Chloro-1-[4-(3-chloro-pyridin-2-yl)-cyclohexyl]-5,6-dihydro-4H-2,3,5,10b-tetraaza-benzo[e]azulene,
cis-8-chloro-1-((1S,4R)-4-(3-fluoropyridin-2-yl)cyclohexyl)-5,6-dihydro-4H-benzo[e][1,2,4]triazolo[4,3-a][1,4]diazepine,
cis-8-chloro-1-((1S,4R)-4-(3-fluoropyridin-2-yl)cyclohexyl)-5-methyl-5,6-dihydro-4H-benzo[e][1,2,4]triazolo[4,3-a][1,4]diazepine,
cis-8-Chloro-1-(4-pyrimidin-2-yl-cyclohexyl)-5,6-dihydro-4H-2,3,5,10b-tetraaza-benzo[e]azulene,
cis-8-Chloro-5-methyl-1-(4-pyrimidin-2-yl-cyclohexyl)-5,6-dihydro-4H-2,3,5,10b-tetraaza-benzo[e]azulene,
cis-tert-butyl 8-chloro-1-((1R,4R)-4-(3-fluoropyridin-2-yl)cyclohexyl)-4H-benzo[e][1,2,4]triazolo[4,3-a][1,4]diazepine-5(6H)-carboxylate,
trans-8-chloro-1-((1R,4R)-4-(2-fluoropyridin-3-yl)cyclohexyl)-5,6-dihydro-4H-benzo[e][1,2,4]triazolo[4,3-a][1,4]diazepine,
trans-8-chloro-1-((1R,4R)-4-(2-fluoropyridin-3-yl)cyclohexyl)-5-methyl-5,6-dihydro-4H-benzo[e][1,2,4]triazolo[4,3-a][1,4]diazepine,
trans-8-chloro-1-((1R,4S)-4-(2-chloropyridin-3-yl)cyclohexyl)-5-methyl-5,6-dihydro-4H-benzo[e][1,2,4]triazolo[4,3-a][1,4]diazepine,
trans-8-chloro-1-((1R,4S)-4-(2-chloropyridin-3-yl)cyclohexyl)-5,6-dihydro-4H-benzo[e][1,2,4]triazolo[4,3-a][1,4]diazepine,
trans-8-chloro-1-((1R,4S)-4-(2-methylpyrimidin-4-yl)cyclohexyl)-5,6-dihydro-4H-benzo[e][1,2,4]triazolo[4,3-a][1,4]diazepine,
trans-8-chloro-1-((1R,4S)-4-(3-fluoropyridin-2-yl)cyclohexyl)-5-(2-methoxyethyl)-5,6-dihydro-4H-benzo[e][1,2,4]triazolo[4,3-a][1,4]diazepine,
trans-8-chloro-1-((1R,4S)-4-(3-fluoropyridin-2-yl)cyclohexyl)-5-(methylsulfonyl)-5,6-dihydro-4H-benzo[e][1,2,4]triazolo[4,3-a][1,4]diazepine,
trans-8-chloro-1-((1R,4S)-4-(3-fluoropyridin-2-yl)cyclohexyl)-5-isopropyl-5,6-dihydro-4H-benzo[e][1,2,4]triazolo[4,3-a][1,4]diazepine,
trans-8-chloro-1-((1R,4S)-4-(3-fluoropyridin-2-yl)cyclohexyl)-N,N-dimethyl-4H-benzo[e][1,2,4]triazolo[4,3-a][1,4]diazepine-5(6H)-sulfonamide, trans-8-chloro-1-((1R,4S)-4-(3-methylpyrazin-2-yl)cyclohexyl)-5,6-dihydro-4H-benzo[e][1,2,4]triazolo[4,3-a][1,4]diazepine,
trans-8-chloro-1-((1R,4S)-4-(4-chloropyridin-2-yl)cyclohexyl)-5,6-dihydro-4H-benzo[e][1,2,4]triazolo[4,3-a][1,4]diazepine,
trans-8-chloro-1-((1R,4S)-4-(4-chloropyridin-2-yl)cyclohexyl)-5-methyl-5,6-dihydro-4H-benzo[e][1,2,4]triazolo[4,3-a][1,4]diazepine,
trans-8-chloro-1-((1R,4S)-4-(6-fluoropyridin-2-yl)cyclohexyl)-5,6-dihydro-4H-benzo[e][1,2,4]triazolo[4,3-a][1,4]diazepine,
trans-8-chloro-1-((1R,4S)-4-(6-fluoropyridin-2-yl)cyclohexyl)-5-methyl-5,6-dihydro-4H-benzo[e][1,2,4]triazolo[4,3-a][1,4]diazepine,
trans-8-Chloro-1-(4-pyrazin-2-yl-cyclohexyl)-4H,6H-2,3,5,10b-tetraaza-benzo[e]azulene-5-carboxylic acid tert-butyl ester,
trans-8-Chloro-1-(4-pyrazin-2-yl-cyclohexyl)-5,6-dihydro-4H-2,3,5,10b-tetraaza-benzo[e]azulene,
trans-8-Chloro-1-(4-pyridin-2-yl-cyclohexyl)-5,6-dihydro-4H-2,3,5,10b-tetraaza-benzo[e]azulene dihydrochloride,
trans-8-Chloro-1-(4-pyridin-3-yl-cyclohexyl)-4H,6H-2,3,5,10b-tetraaza-benzo[e]azulene-5-carboxylic acid tert-butyl ester,
trans-8-Chloro-1-(4-pyridin-3-yl-cyclohexyl)-5,6-dihydro-4H-2,3,5,10b-tetraaza-benzo[e]azulene,
trans-8-Chloro-1-[4-(3,6-dimethyl-pyrazin-2-yl)-cyclohexyl]-4H,6H-2,3,5,10b-tetraaza-benzo[e]azulene-5-carboxylic acid tert-butyl ester,
trans-8-Chloro-1-[4-(3,6-dimethyl-pyrazin-2-yl)-cyclohexyl]-5,6-dihydro-4H-2,3,5,10b-tetraaza-benzo[e]azulene hydrochloride,
trans-8-Chloro-1-[4-(3,6-dimethyl-pyrazin-2-yl)-cyclohexyl]-5-methyl-5,6-dihydro-4H-2,3,5,10b-tetraaza-benzo[e]azulene,
trans-8-Chloro-1-[4-(3-fluoro-pyridin-2-yl)-cyclohexyl]-4H,6H-2,3,5,10b-tetraaza-benzo[e]azulene-5-carboxylic acid tert-butyl ester,
trans-8-Chloro-1-[4-(3-fluoro-pyridin-2-yl)-cyclohexyl]-5,6-dihydro-4H-2,3,5,10b-tetraaza-benzo[e]azulene,
trans-8-Chloro-1-[4-(3-fluoro-pyridin-2-yl)-cyclohexyl]-5-methyl-5,6-dihydro-4H-2,3,5,10b-tetraaza-benzo[e]azulene,
trans-8-Chloro-1-[4-(4,6-dimethyl-pyrimidin-2-yl)-cyclohexyl]-4H,6H-2,3,5,10b-tetraaza-benzo[e]azulene-5-carboxylic acid tert-butyl ester,
trans-8-Chloro-1-[4-(4,6-dimethyl-pyrimidin-2-yl)-cyclohexyl]-5,6-dihydro-4H-2,3,5,10b-tetraaza-benzo[e]azulene hydrochloride,
trans-8-Chloro-1-[4-(4,6-dimethyl-pyrimidin-2-yl)-cyclohexyl]-5-methyl-5,6-dihydro-4H-2,3,5,10b-tetraaza-benzo[e]azulene,
trans-8-Chloro-1-[4-(5-fluoro-pyridin-2-yl)-cyclohexyl]-4H,6H-2,3,5,10b-tetraaza-benzoazulene-5-carboxylic acid tert-butyl ester,
trans-8-Chloro-1-[4-(5-fluoro-pyridin-2-yl)-cyclohexyl]-5,6-dihydro-4H-2,3,5,10b-tetraaza-benzoazulene dihydrochloride,
trans-8-Chloro-1-[4-(5-fluoro-pyridin-2-yl)-cyclohexyl]-5-methyl-5,6-dihydro-4H-2,3,5,10b-tetraaza-benzoazulene,
trans-8-Chloro-1-[4-(6-chloro-pyridin-2-yl)-cyclohexyl]-4H,6H-2,3,5,10b-tetraaza-benzo[e]azulene-5-carboxylic acid tert-butyl ester,
trans-8-Chloro-1-[4-(6-chloro-pyridin-2-yl)-cyclohexyl]-5,6-dihydro-4H-2,3,5,10b-tetraaza-benzo[e]azulene,
trans-8-Chloro-1-[4-(6-chloro-pyridin-2-yl)-cyclohexyl]-5-methyl-5,6-dihydro-4H-2,3,5,10b-tetraaza-benzo[e]azulene,
trans-8-Chloro-1-[4-(6-ethyl-pyridin-2-yl)-cyclohexyl]-4H,6H-2,3,5,10b-tetraaza-benzo[e]azulene-5-carboxylic acid tert-butyl ester,
trans-8-Chloro-1-[4-(6-ethyl-pyridin-2-yl)-cyclohexyl]-5,6-dihydro-4H-2,3,5,10b-tetraaza-benzo[e]azulene,
trans-8-Chloro-1-[4-(6-ethyl-pyridin-2-yl)-cyclohexyl]-5-methyl-5,6-dihydro-4H-2,3,5,10b-tetraaza-benzo[e]azulene,
trans-8-Chloro-1-[4-(6-isopropyl-pyridin-2-yl)-cyclohexyl]-4H,6H-2,3,5,10b-tetraaza-benzo[e]azulene-5-carboxylic acid tert-butyl ester,
trans-8-Chloro-1-[4-(6-isopropyl-pyridin-2-yl)-cyclohexyl]-5,6-dihydro-4H-2,3,5,10b-tetraaza-benzo[e]azulene hydrochloride,
trans-8-Chloro-1-[4-(6-isopropyl-pyridin-2-yl)-cyclohexyl]-5-methyl-5,6-dihydro-4H-2,3,5,10b-tetraaza-benzo[e]azulene,
trans-8-Chloro-1-[4-(6-methoxy-pyridin-2-yl)-cyclohexyl]-4H,6H-2,3,5,10b-tetraaza-benzoazulene-5-carboxylic acid tert-butyl ester,
trans-8-Chloro-1-[4-(6-methoxy-pyridin-2-yl)-cyclohexyl]-5,6-dihydro-4H-2,3,5,10b-tetraaza-benzoazulene,
trans-8-Chloro-1-[4-(6-methoxy-pyridin-2-yl)-cyclohexyl]-5-methyl-5,6-dihydro-4H-2,3,5,10b-tetraaza-benzoazulene,
trans-8-Chloro-1-[4-(6-methyl-pyrazin-2-yl)-cyclohexyl]-4H,6H-2,3,5,10b-tetraaza-benzo[e]azulene-5-carboxylic acid tert-butyl ester,
trans-8-Chloro-1-[4-(6-methyl-pyrazin-2-yl)-cyclohexyl]-5,6-dihydro-4H-2,3,5,10b-tetraaza-benzo[e]azulene,
trans-8-Chloro-1-[4-(6-methyl-pyridin-2-yl)-cyclohexyl]-4H,6H-2,3,5,10b-tetraaza-benzo[e]azulene-5-carboxylic acid tert-butyl ester,
trans-8-Chloro-1-[4-(6-methyl-pyridin-2-yl)-cyclohexyl]-5,6-dihydro-4H-2,3,5,10b-tetraaza-benzo[e]azulene,
trans-8-chloro-5-(2,2-difluoroethyl)-1-((1R,4S)-4-(3-fluoropyridin-2-yl)cyclohexyl)-5,6-dihydro-4H-benzo[e][1,2,4]triazolo[4,3-a][1,4]diazepine,
trans-8-chloro-5-cyclobutyl-1-((1R,4S)-4-(3-fluoropyridin-2-yl)cyclohexyl)-5,6-dihydro-4H-benzo[e][1,2,4]triazolo[4,3-a][1,4]diazepine,
trans-8-chloro-5-ethyl-1-((1R,4S)-4-(3-fluoropyridin-2-yl)cyclohexyl)-5,6-dihydro-4H-benzo[e][1,2,4]triazolo[4,3-a][1,4]diazepine,
trans-8-chloro-5-methyl-1-((1R,4S)-4-(2-methylpyrimidin-4-yl)cyclohexyl)-5,6-dihydro-4H-benzo[e][1,2,4]triazolo[4,3-a][1,4]diazepine,
trans-8-chloro-5-methyl-1-((1R,4S)-4-(3-methylpyrazin-2-yl)cyclohexyl)-5,6-dihydro-4H-benzo[e][1,2,4]triazolo[4,3-a][1,4]diazepine,
trans-8-Chloro-5-methyl-1-(4-pyrazin-2-yl-cyclohexyl)-5,6-dihydro-4H-2,3,5,10b-tetraaza-benzo[e]azulene,
trans-8-Chloro-5-methyl-1-(4-pyridazin-3-yl-cyclohexyl)-5,6-dihydro-4H-2,3,5,10b-tetraaza-benzo[e]azulene,
trans-8-Chloro-5-methyl-1-(4-pyridin-2-yl-cyclohexyl)-5,6-dihydro-4H-2,3,5,10b-tetraaza-benzo[e]azulene,
trans-8-Chloro-5-methyl-1-(4-pyridin-3-yl-cyclohexyl)-5,6-dihydro-4H-2,3,5,10b-tetraaza-benzo[e]azulene,
trans-8-Chloro-5-methyl-1-[4-(6-methyl-pyrazin-2-yl)-cyclohexyl]-5,6-dihydro-4H-2,3,5,10b-tetraaza-benzo[e]azulene,
trans-8-Chloro-5-methyl-1-[4-(6-methyl-pyridin-2-yl)-cyclohexyl]-5,6-dihydro-4H-2,3,5,10b-tetraaza-benzo[e]azulene, trans-8-fluoro-1-((1R,4S)-4-(3-fluoropyridin-2-yl)cyclohexyl)-5,6-dihydro-4H-benzo[e][1,2,4]triazolo[4,3-a][1,4]diazepine, trans-8-fluoro-1-((1R,4S)-4-(3-fluoropyridin-2-yl)cyclohexyl)-5-methyl-5,6-dihydro-4H-benzo[e][1,2,4]triazolo[4,3-a][1,4]diazepine, trans-tert-butyl 8-chloro-1-((1R,4R)-4-(2-fluoropyridin-3-yl)cyclohexyl)-4H-benzo[e][1,2,4]triazolo[4,3-a][1,4]diazepine-5(6H)-carboxylate, trans-tert-butyl 8-chloro-1-((1R,4S)-4-(2-chloropyridin-3-yl)cyclohexyl)-4H-benzo[e][1,2,4]triazolo[4,3-a][1,4]diazepine-5(6H)-carboxylate, trans-tert-butyl 8-chloro-1-((1R,4S)-4-(2-methylpyrimidin-4-yl)cyclohexyl)-4H-benzo[e][1,2,4]triazolo[4,3-a][1,4]diazepine-5(6H)-carboxylate, trans-tert-butyl 8-chloro-1-((1R,4S)-4-(3-methylpyrazin-2-yl)cyclohexyl)-4H-benzo[e][1,2,4]triazolo[4,3-a][1,4]diazepine-5(6H)-carboxylate, trans-tert-butyl 8-chloro-1-((1R,4S)-4-(4-chloropyridin-2-yl)cyclohexyl)-4H-benzo[e][1,2,4]triazolo[4,3-a][1,4]diazepine-5(6H)-carboxylate, trans-tert-butyl 8-chloro-1-((1R,4S)-4-(6-fluoropyridin-2-yl)cyclohexyl)-4H-benzo[e][1,2,4]triazolo[4,3-a][1,4]diazepine-5(6H)-carboxylate, and trans-tert-butyl 8-fluoro-1-((1R,4S)-4-(3-fluoropyridin-2-yl)cyclohexyl)-4H-benzo[e][1,2,4]triazolo[4,3-a][1,4]diazepine-5(6H)-carboxylate, or a pharmaceutically acceptable salt thereof.

A certain embodiment of the invention relates to compounds selected from the group consisting of trans-8-Chloro-1-(4-pyridin-2-yl-cyclohexyl)-4H,6H-2,3,5,10b-tetraaza-benzo[e]azulene-5-carboxylic acid tert-butyl ester, trans-8-Chloro-1-(4-pyridin-2-yl-cyclohexyl)-5,6-dihydro-4H-2,3,5,10b-tetraaza-benzo[e]azulene, trans-8-Chloro-5-methyl-1-(4-pyridin-2-yl-cyclohexyl)-5,6-dihydro-4H-2,3,5,10b-tetraaza-benzo[e]azulene, trans-8-Chloro-1-[4-(6-methyl-pyridin-2-yl)-cyclohexyl]-4H,6H-2,3,5,10b-tetraaza-benzo[e]azulene-5-carboxylic acid tert-butyl ester, trans-8-Chloro-1-[4-(6-methyl-pyridin-2-yl)-cyclohexyl]-5,6-dihydro-4H-2,3,5,10b-tetraaza-benzo[e]azulene, trans-8-Chloro-5-methyl-1-[4-(6-methyl-pyridin-2-yl)-cyclohexyl]-5,6-dihydro-4H-2,3,5,10b-tetraaza-benzo[e]azulene, trans-8-Chloro-1-[4-(6-ethyl-pyridin-2-yl)-cyclohexyl]-4H,6H-2,3,5,10b-tetraaza-benzo[e]azulene-5-carboxylic acid tert-butyl ester, trans-8-Chloro-1-[4-(6-ethyl-pyridin-2-yl)-cyclohexyl]-5,6-dihydro-4H-2,3,5,10b-tetraaza-benzo[e]azulene, trans-8-Chloro-1-[4-(6-ethyl-pyridin-2-yl)-cyclohexyl]-5-methyl-5,6-dihydro-4H-2,3,5,10b-tetraaza-benzo[e]azulene, trans-8-Chloro-1-[4-(6-isopropyl-pyridin-2-yl)-cyclohexyl]-4H,6H-2,3,5,10b-tetraaza-benzo[e]azulene-5-carboxylic acid tert-butyl ester, trans-8-Chloro-1-[4-(6-isopropyl-pyridin-2-yl)-cyclohexyl]-5,6-dihydro-4H-2,3,5,10b-tetraaza-benzo[e]azulene hydrochloride, trans-8-Chloro-1-[4-(6-isopropyl-pyridin-2-yl)-cyclohexyl]-5-methyl-5,6-dihydro-4H-2,3,5,10b-tetraaza-benzo[e]azulene, trans-8-Chloro-1-[4-(6-methoxy-pyridin-2-yl)-cyclohexyl]-4H,6H-2,3,5,10b-tetraaza-benzoazulene-5-carboxylic acid tert-butyl ester, trans-8-Chloro-1-[4-(6-methoxy-pyridin-2-yl)-cyclohexyl]-5,6-dihydro-4H-2,3,5,10b-tetraaza-benzoazulene, trans-8-Chloro-1-[4-(6-methoxy-pyridin-2-yl)-cyclohexyl]-5-methyl-5,6-dihydro-4H-2,3,5,10b-tetraaza-benzoazulene, trans-8-Chloro-1-[4-(6-chloro-pyridin-2-yl)-cyclohexyl]-4H,6H-2,3,5,10b-tetraaza-benzo[e]azulene-5-carboxylic acid tert-butyl ester, trans-8-Chloro-1-[4-(6-chloro-pyridin-2-yl)-cyclohexyl]-5,6-dihydro-4H-2,3,5,10b-tetraaza-benzo[e]azulene, trans-8-Chloro-1-[4-(6-chloro-pyridin-2-yl)-cyclohexyl]-5-methyl-5,6-dihydro-4H-2,3,5,10b-tetraaza-benzo[e]azulene, trans-tert-Butyl 8-chloro-1-(-4-(6-fluoropyridin-2-yl)cyclohexyl)-4H-benzo[e][1,2,4]triazolo[4,3-a][1,4]diazepine-5(6H)-carboxylate, trans-8-Chloro-1-(-4-(6-fluoropyridin-2-yl)cyclohexyl)-5,6-dihydro-4H-benzo[e][1,2,4]triazolo[4,3-a][1,4]diazepine, trans-8-Chloro-1-(-4-(6-fluoropyridin-2-yl)cyclohexyl)-5-methyl-5,6-dihydro-4H-benzo[e][1,2,4]triazolo[4,3-a][1,4]diazepine, trans-8-Chloro-1-[4-(5-fluoro-pyridin-2-yl)-cyclohexyl]-4H,6H-2,3,5,10b-tetraaza-benzoazulene-5-carboxylic acid tert-butyl ester, trans-8-Chloro-1-[4-(5-fluoro-pyridin-2-yl)-cyclohexyl]-5,6-dihydro-4H-2,3,5,10b-tetraaza-benzoazulene, trans-8-Chloro-1-[4-(5-fluoro-pyridin-2-yl)-cyclohexyl]-5-methyl-5,6-dihydro-4H-2,3,5,10b-tetraaza-benzoazulene, trans-tert-Butyl 8-chloro-1-(-4-(4-chloropyridin-2-yl)cyclohexyl)-4H-benzo[e][1,2,4]triazolo[4,3-a][1,4]diazepine-5(6H)-carboxylate, trans-8-chloro-1-(-4-(4-chloropyridin-2-yl)cyclohexyl)-5,6-dihydro-4H-benzo[e][1,2,4]triazolo[4,3-a][1,4]diazepine, trans-8-Chloro-1-(-4-(4-chloropyridin-2-yl)cyclohexyl)-5-methyl-5,6-dihydro-4H-benzo[e][1,2,4]triazolo[4,3-a][1,4]diazepine, trans-8-Chloro-1-[4-(3-fluoro-pyridin-2-yl)-cyclohexyl]-4H,6H-2,3,5,10b-tetraaza-benzo[e]azulene-5-carboxylic acid tert-butyl ester, trans-8-Chloro-1-[4-(3-fluoro-pyridin-2-yl)-cyclohexyl]-5,6-dihydro-4H-2,3,5,10b-tetraaza-benzo[e]azulene, trans-8-Chloro-1-[4-(3-fluoro-pyridin-2-yl)-cyclohexyl]-5-methyl-5,6-dihydro-4H-2,3,5,10b-tetraaza-benzo[e]azulene, trans-8-Chloro-5-ethyl-1-(-4-(3-fluoropyridin-2-yl)cyclohexyl)-5,6-dihydro-4H-benzo[e][1,2,4]triazolo[4,3-a][1,4]diazepine, trans-8-Chloro-1-(-4-(3-fluoropyridin-2-yl)cyclohexyl)-5-isopropyl-5,6-dihydro-4H-benzo[e][1,2,4]triazolo[4,3-a][1,4]diazepine, trans-8-Chloro-5-cyclobutyl-1-(-4-(3-fluoropyridin-2-yl)cyclohexyl)-5,6-dihydro-4H-benzo[e][1,2,4]triazolo[4,3-a][1,4]diazepine, trans-8-Chloro-5-(2,2-difluoroethyl)-1-(-4-(3-fluoropyridin-2-yl)cyclohexyl)-5,6-dihydro-4H-benzo[e][1,2,4]triazolo[4,3-a][1,4]diazepine, trans-8-Chloro-1-(-4-(3-fluoropyridin-2-yl)cyclohexyl)-5-(2-methoxyethyl)-5,6-dihydro-4H-benzo[e][1,2,4]triazolo[4,3-a][1,4]diazepine, 2-(trans-8-Chloro-1-(-4-(3-fluoropyridin-2-yl)cyclohexyl)-4H-benzo[e][1,2,4]triazolo[4,3-a][1,4]diazepin-5(6H)-yl)-N-methylethanamine, 1-(trans-8-chloro-1-(-4-(3-fluoropyridin-2-yl)cyclohexyl)-4H-benzo[e][1,2,4]triazolo[4,3-a][1,4]diazepin-5(6H)-yl)ethanone, 1-(trans-8-chloro-1-(–4-(3-fluoropyridin-2-yl)cyclohexyl)-4H-benzo[e][1,2,4]triazolo[4,3-a][1,4]diazepin-5(6H)-yl)-2-hydroxyethanone,
1-(trans-8-Chloro-1-(–4-(3-fluoropyridin-2-yl)cyclohexyl)-4H-benzo[e][1,2,4]triazolo[4,3-a][1,4]diazepin-5(6H)-yl)-2-(dimethylamino)ethanone,
trans-8-Chloro-1-(–4-(3-fluoropyridin-2-yl)cyclohexyl)-5-(methylsulfonyl)-5,6-dihydro-4H-benzo[e][1,2,4]triazolo[4,3-a][1,4]diazepine,
trans-8-Chloro-1-(–4-(3-fluoropyridin-2-yl)cyclohexyl)-N,N-dimethyl-4H-benzo[e][1,2,4]triazolo[4,3-a][1,4]diazepine-5(6H)-sulfonamide,
trans-tert-Butyl 8-fluoro-1-(–4-(3-fluoropyridin-2-yl)cyclohexyl)-4H-benzo[e][1,2,4]triazolo[4,3-a][1,4]diazepine-5(6H)-carboxylate,
trans-8-Fluoro-1-(–4-(3-fluoropyridin-2-yl)cyclohexyl)-5,6-dihydro-4H-benzo[e][1,2,4]triazolo[4,3-a][1,4]diazepine,
trans-8-Fluoro-1-(–4-(3-fluoropyridin-2-yl)cyclohexyl)-5-methyl-5,6-dihydro-4H-benzo[e][1,2,4]triazolo[4,3-a][1,4]diazepine,
cis-tert-Butyl 8-chloro-1-(4-(3-fluoropyridin-2-yl)cyclohexyl)-4H-benzo[e][1,2,4]triazolo[4,3-a][1,4]diazepine-5(6H)-carboxylate,
cis-8-Chloro-1-(4-(3-fluoropyridin-2-yl)cyclohexyl)-5,6-dihydro-4H-benzo[e][1,2,4]triazolo[4,3-a][1,4]diazepine,
cis-8-Chloro-1-(4-(3-fluoropyridin-2-yl)cyclohexyl)-5-methyl-5,6-dihydro-4H-benzo[e][1,2,4]triazolo[4,3-a][1,4]diazepine,
trans-8-Chloro-1-(4-pyridin-3-yl-cyclohexyl)-4H,6H-2,3,5,10b-tetraaza-benzo[e]azulene-5-carboxylic acid tert-butyl ester,
trans-8-Chloro-1-(4-pyridin-3-yl-cyclohexyl)-5,6-dihydro-4H-2,3,5,10b-tetraaza-benzo[e]azulene,
trans-8-Chloro-5-methyl-1-(4-pyridin-3-yl-cyclohexyl)-5,6-dihydro-4H-2,3,5,10b-tetraaza-benzo[e]azulene,
trans-tert-Butyl 8-chloro-1-(–4-(2-chloropyridin-3-yl)cyclohexyl)-4H-benzo[e][1,2,4]triazolo[4,3-a][1,4]diazepine-5(6H)-carboxylate,
trans-8-Chloro-1-(–4-(2-chloropyridin-3-yl)cyclohexyl)-5,6-dihydro-4H-benzo[e][1,2,4]triazolo[4,3-a][1,4]diazepine,
trans-8-Chloro-1-(–4-(2-chloropyridin-3-yl)cyclohexyl)-5-methyl-5,6-dihydro-4H-benzo[e][1,2,4]triazolo[4,3-a][1,4]diazepine,
trans-tert-Butyl 8-chloro-1-(4-(2-fluoropyridin-3-yl)cyclohexyl)-4H-benzo[e][1,2,4]triazolo[4,3-a][1,4]diazepine-5(6H)-carboxylate,
trans-8-Chloro-1-(4-(2-fluoropyridin-3-yl)cyclohexyl)-5,6-dihydro-4H-benzo[e][1,2,4]triazolo[4,3-a][1,4]diazepine,
trans-8-Chloro-1-(4-(2-fluoropyridin-3-yl)cyclohexyl)-5-methyl-5,6-dihydro-4H-benzo[e][1,2,4]triazolo[4,3-a][1,4]diazepine,
trans-8-Chloro-1-(4-pyrimidin-2-yl-cyclohexyl)-4H,6H-2,3,5,10b-tetraaza-benzo[e]azulene-5-carboxylic acid tert-butyl ester,
cis-8-Chloro-1-(4-pyrimidin-2-yl-cyclohexyl)-4H,6H-2,3,5,10b-tetraaza-benzo[e]azulene-5-carboxylic acid tert-butyl ester,
trans-8-Chloro-1-(4-pyrimidin-2-yl-cyclohexyl)-5,6-dihydro-4H-2,3,5,10b-tetraaza-benzo[e]azulene,
trans-8-Chloro-5-methyl-1-(4-pyrimidin-2-yl-cyclohexyl)-5,6-dihydro-4H-2,3,5,10b-tetraaza-benzo[e]azulene,
cis-8-Chloro-1-(4-pyrimidin-2-yl-cyclohexyl)-5,6-dihydro-4H-2,3,5,10b-tetraaza-benzo[e]azulene,
cis-8-Chloro-5-methyl-1-(4-pyrimidin-2-yl-cyclohexyl)-5,6-dihydro-4H-2,3,5,10b-tetraaza-benzo[e]azulene,
trans-8-Chloro-1-[4-(4,6-dimethyl-pyrimidin-2-yl)-cyclohexyl]-4H,6H-2,3,5,10b-tetraaza-benzo[e]azulene-5-carboxylic acid tert-butyl ester,
trans-8-Chloro-1-[4-(4,6-dimethyl-pyrimidin-2-yl)-cyclohexyl]-5,6-dihydro-4H-2,3,5,10b-tetraaza-benzo[e]azulene,
trans-8-Chloro-1-[4-(4,6-dimethyl-pyrimidin-2-yl)-cyclohexyl]-5-methyl-5,6-dihydro-4H-2,3,5,10b-tetraaza-benzo[e]azulene,
trans-tert-Butyl 8-chloro-1-(–4-(2-methylpyrimidin-4-yl)cyclohexyl)-4H-benzo[e][1,2,4]triazolo[4,3-a][1,4]diazepine-5(6H)-carboxylate,
trans-8-Chloro-1-(–4-(2-methylpyrimidin-4-yl)cyclohexyl)-5,6-dihydro-4H-benzo[e][1,2,4]triazolo[4,3-a][1,4]diazepine,
trans-8-Chloro-5-methyl-1-(–4-(2-methylpyrimidin-4-yl)cyclohexyl)-5,6-dihydro-4H-benzo[e][1,2,4]triazolo[4,3-a][1,4]diazepine,
trans-8-Chloro-1-(4-pyrazin-2-yl-cyclohexyl)-4H,6H-2,3,5,10b-tetraaza-benzo[e]azulene-5-carboxylic acid tert-butyl ester,
trans-8-Chloro-1-(4-pyrazin-2-yl-cyclohexyl)-5,6-dihydro-4H-2,3,5,10b-tetraaza-benzo[e]azulene,
trans-8-Chloro-5-methyl-1-(4-pyrazin-2-yl-cyclohexyl)-5,6-dihydro-4H-2,3,5,10b-tetraaza-benzo[e]azulene,
trans-8-Chloro-1-[4-(6-methyl-pyrazin-2-yl)-cyclohexyl]-4H,6H-2,3,5,10b-tetraaza-benzo[e]azulene-5-carboxylic acid tert-butyl ester,
trans-8-Chloro-1-[4-(6-methyl-pyrazin-2-yl)-cyclohexyl]-5,6-dihydro-4H-2,3,5,10b-tetraaza-benzo[e]azulene,
trans-8-Chloro-5-methyl-1-[4-(6-methyl-pyrazin-2-yl)-cyclohexyl]-5,6-dihydro-4H-2,3,5,10b-tetraaza-benzo[e]azulene,
trans-tert-Butyl 8-chloro-1-(–4-(3-methylpyrazin-2-yl)cyclohexyl)-4H-benzo[e][1,2,4]triazolo[4,3-a][1,4]diazepine-5(6H)-carboxylate,
trans-8-Chloro-1-(–4-(3-methylpyrazin-2-yl)cyclohexyl)-5,6-dihydro-4H-benzo[e][1,2,4]triazolo[4,3-a][1,4]diazepine,
trans-8-Chloro-5-methyl-1-(–4-(3-methylpyrazin-2-yl)cyclohexyl)-5,6-dihydro-4H-benzo[e][1,2,4]triazolo[4,3-a][1,4]diazepine,
trans-8-Chloro-1-[4-(3,6-dimethyl-pyrazin-2-yl)-cyclohexyl]-4H,6H-2,3,5,10b-tetraaza-benzo[e]azulene-5-carboxylic acid tert-butyl ester,
trans-8-Chloro-1-[4-(3,6-dimethyl-pyrazin-2-yl)-cyclohexyl]-5,6-dihydro-4H-2,3,5,10b-tetraaza-benzo[e]azulene,
trans-8-Chloro-1-[4-(3,6-dimethyl-pyrazin-2-yl)-cyclohexyl]-5-methyl-5,6-dihydro-4H-2,3,5,10b-tetraaza-benzo[e]azulene, and
trans-8-Chloro-5-methyl-1-(4-pyridazin-3-yl-cyclohexyl)-5,6-dihydro-4H-2,3,5,10b-tetraaza-benzo[e]azulene,
or a pharmaceutically acceptable salt thereof.

A certain embodiment of the invention relates to compounds selected from the group consisting of
trans-8-Chloro-1-(4-pyridin-2-yl-cyclohexyl)-5,6-dihydro-4H-2,3,5,10b-tetraaza-benzo[e]azulene.2HCl,
trans-8-Chloro-5-methyl-1-(4-pyridin-2-yl-cyclohexyl)-5,6-dihydro-4H-2,3,5,10b-tetraaza-benzo[e]azulene,
trans-8-Chloro-5-methyl-1-[4-(6-methyl-pyridin-2-yl)-cyclohexyl]-5,6-dihydro-4H-2,3,5,10b-tetraaza-benzo[e]azulene,
trans-8-Chloro-1-[4-(6-chloro-pyridin-2-yl)-cyclohexyl]-5,6-dihydro-4H-2,3,5,10b-tetraaza-benzo[e]azulene, trans-8-Chloro-1-[4-(6-chloro-pyridin-2-yl)-cyclohexyl]-5-methyl-5,6-dihydro-4H-2,3,5,10b-tetraaza-benzo[e]azulene, trans-8-Chloro-1-[4-(5-fluoro-pyridin-2-yl)-cyclohexyl]-5,6-dihydro-4H-2,3,5,10b-tetraaza-benzoazulene dihydrochloride, trans-8-Chloro-1-[4-(5-fluoro-pyridin-2-yl)-cyclohexyl]-5-methyl-5,6-dihydro-4H-2,3,5,10b-tetraaza-benzoazulene, trans-8-Chloro-1-[4-(3-fluoro-pyridin-2-yl)-cyclohexyl]-5,6-dihydro-4H-2,3,5,10b-tetraaza-benzo[e]azulene, trans-8-Chloro-1-[4-(3-fluoro-pyridin-2-yl)-cyclohexyl]-5-methyl-5,6-dihydro-4H-2,3,5,10b-tetraaza-benzo[e]azulene, trans-8-Chloro-5-ethyl-1-(4-(3-fluoropyridin-2-yl)cyclohexyl)-5,6-dihydro-4H-benzo[e][1,2,4]triazolo[4,3-a][1,4]diazepine, trans-8-Chloro-1-(4-(3-fluoropyridin-2-yl)cyclohexyl)-5-isopropyl-5,6-dihydro-4H-benzo[e][1,2,4]triazolo[4,3-a][1,4]diazepine, trans-8-Chloro-5-cyclobutyl-1-(4-(3-fluoropyridin-2-yl)cyclohexyl)-5,6-dihydro-4H-benzo[e][1,2,4]triazolo[4,3-a][1,4]diazepine, trans-8-Chloro-5-(2,2-difluoroethyl)-1-(4-(3-fluoropyridin-2-yl)cyclohexyl)-5,6-dihydro-4H-benzo[e][1,2,4]triazolo[4,3-a][1,4]diazepine, trans-8-Chloro-1-(4-(3-fluoropyridin-2-yl)cyclohexyl)-5-(2-methoxyethyl)-5,6-dihydro-4H-benzo[e][1,2,4]triazolo[4,3-a][1,4]diazepine, trans-8-Chloro-5-methyl-1-(4-pyrazin-2-yl-cyclohexyl)-5,6-dihydro-4H-2,3,5,10b-tetraaza-benzo[e]azulene, trans-8-Chloro-1-[4-(3-chloro-pyridin-2-yl)-cyclohexyl]-5-methyl-5,6-dihydro-4H-2,3,5,10b-tetraaza-benzo[e]azulene, and trans-8-Chloro-1-[4-(3,5-difluoro-pyridin-2-yl)-cyclohexyl]-5-methyl-5,6-dihydro-4H-2,3,5,10b-tetraaza-benzo[e]azulene.

A certain embodiment of the invention relates to compounds selected from the group consisting of trans-8-Chloro-1-(4-pyridin-2-yl-cyclohexyl)-5,6-dihydro-4H-2,3,5,10b-tetraaza-benzo[e]azulene.2HCl, trans-8-Chloro-5-methyl-1-(4-pyridin-2-yl-cyclohexyl)-5,6-dihydro-4H-2,3,5,10b-tetraaza-benzo[e]azulene, trans-8-Chloro-5-methyl-1-[4-(6-methyl-pyridin-2-yl)-cyclohexyl]-5,6-dihydro-4H-2,3,5,10b-tetraaza-benzo[e]azulene, trans-8-Chloro-1-[4-(6-chloro-pyridin-2-yl)-cyclohexyl]-5,6-dihydro-4H-2,3,5,10b-tetraaza-benzo[e]azulene, trans-8-Chloro-1-[4-(6-chloro-pyridin-2-yl)-cyclohexyl]-5-methyl-5,6-dihydro-4H-2,3,5,10b-tetraaza-benzo[e]azulene, trans-8-Chloro-1-[4-(5-fluoro-pyridin-2-yl)-cyclohexyl]-5,6-dihydro-4H-2,3,5,10b-tetraaza-benzoazulene dihydrochloride, trans-8-Chloro-1-[4-(5-fluoro-pyridin-2-yl)-cyclohexyl]-5-methyl-5,6-dihydro-4H-2,3,5,10b-tetraaza-benzoazulene, trans-8-Chloro-1-[4-(3-fluoro-pyridin-2-yl)-cyclohexyl]-5,6-dihydro-4H-2,3,5,10b-tetraaza-benzo[e]azulene, trans-8-Chloro-1-[4-(3-fluoro-pyridin-2-yl)-cyclohexyl]-5-methyl-5,6-dihydro-4H-2,3,5,10b-tetraaza-benzo[e]azulene, trans-8-Chloro-5-ethyl-1-(4-(3-fluoropyridin-2-yl)cyclohexyl)-5,6-dihydro-4H-benzo[e][1,2,4]triazolo[4,3-a][1,4]diazepine, trans-8-Chloro-1-(4-(3-fluoropyridin-2-yl)cyclohexyl)-5-isopropyl-5,6-dihydro-4H-benzo[e][1,2,4]triazolo[4,3-a][1,4]diazepine, trans-8-Chloro-5-cyclobutyl-1-(4-(3-fluoropyridin-2-yl)cyclohexyl)-5,6-dihydro-4H-benzo[e][1,2,4]triazolo[4,3-a][1,4]diazepine, trans-8-Chloro-5-(2,2-difluoroethyl)-1-(4-(3-fluoropyridin-2-yl)cyclohexyl)-5,6-dihydro-4H-benzo[e][1,2,4]triazolo[4,3-a][1,4]diazepine, trans-8-Chloro-1-(4-(3-fluoropyridin-2-yl)cyclohexyl)-5-(2-methoxyethyl)-5,6-dihydro-4H-benzo[e][1,2,4]triazolo[4,3-a][1,4]diazepine, and trans-8-Chloro-5-methyl-1-(4-pyrazin-2-yl-cyclohexyl)-5,6-dihydro-4H-2,3,5,10b-tetraaza-benzo[e]azulene.

A certain embodiment of the invention is a compound as described in any of the embodiments obtainable by a process according as described herein.

A certain embodiment of the invention is a compound as described in any of the embodiments, whenever obtained by a process according as described herein.

A certain embodiment of the invention is a compound as described in any of the embodiments for the use as therapeutically active substance.

A certain embodiment of the invention is a compound as described in any of the embodiments for a use in the prevention or treatment of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior.

A certain embodiment of the invention is a pharmaceutical composition comprising a compound as described in any of the embodiments.

A certain embodiment of the invention is a pharmaceutical composition comprising a compound as described in any of the embodiments, wherein it is useful for the prevention or treatment of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior.

A certain embodiment of the invention is the use of a compound as described in any of the embodiments for the preparation of a medicament.

A certain embodiment of the invention is the use of a compound as described in any of the embodiments for the preparation of a medicament, wherein the medicament is useful for the prevention or treatment of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior.

A certain embodiment of the invention is the use of a compound as described in any of the embodiments for the prevention or treatment of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior.

A certain embodiment of the invention is a method for the therapeutic and/or prophylactic treatment of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior, which method comprises administering a compound as defined in any if the embodiments to a human being or animal.

In a certain embodiment, the compounds of formula I of the invention can be manufactured according to a process comprising the step of reacting a compound of formula II

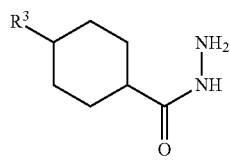

with a compound of formula III,

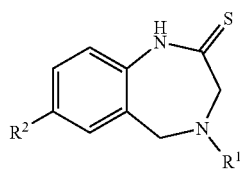

to obtain a compound of formula I wherein $R^1$, $R^2$ and $R^3$ are as defined hereinabove for formula I.

The processes are described in more detail with the following general schemes and procedures A to G.

Scheme 1: General Scheme A

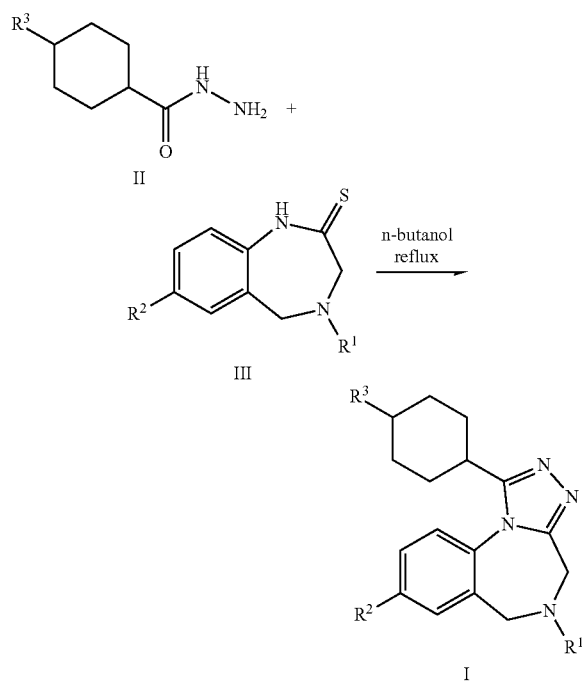

Compounds of formula I can be prepared by thermal condensation of a hydrazide of formula II and a thiolactam of formula III. The synthesis of compounds of formula II is outlined in general schemes D-G hereinafter. Compounds of formula III can be prepared following the procedures described in general scheme C as described hereinafter. General scheme A is hereinafter further illustrated with general procedure X.

Scheme 2: General Scheme B

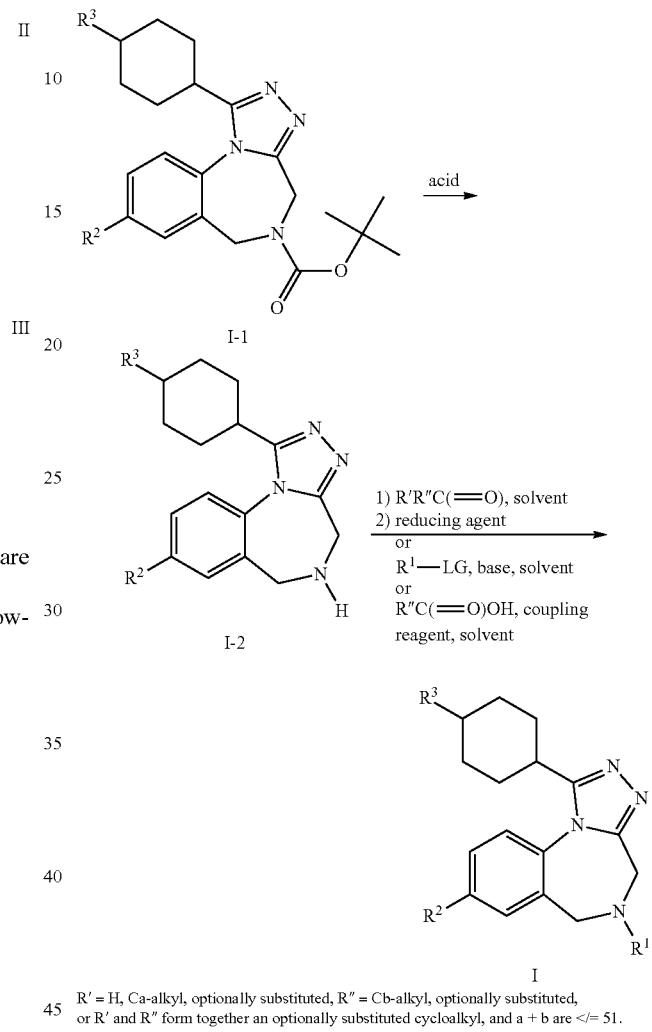

$R'$ = H, Ca-alkyl, optionally substituted, $R''$ = Cb-alkyl, optionally substituted, or $R'$ and $R''$ form together an optionally substituted cycloalkyl, and a + b are $</= 51$.

Compounds of formula I with $R^1$ different from H can be prepared from compounds of formula I-2 (compounds of formula I wherein $R^1$ is H) according to methods known in the art, e.g. by treating a compound of formula I-2 with an inorganic base such as a carbonate salt or an organic base such as a tertiary amine and an electrophilic reactant $R^1$-LG (wherein LG is a leaving group like halogen or sulfonyl) which is either commercially available or easily prepared according to methods and starting materials well known in the art. Alternatively, compounds of formula I can be obtained via reductive alkylation by consecutively treating a compound of formula I-2 with a ketone or aldehyde and a suitable reducing agent like a borohydride derivative such as sodium borohydride, sodium cyanoborohydride or sodium triacetoxyborohydride. Alternatively, compounds of formula I, in which $R^1$ is an acyl group, can be manufactured by coupling an amine of formula I-2 with a carboxylic acid. The usual reagents and protocols known in the art can be used to effect the amide coupling. Compounds of formula I-2 can be obtained by cleavage of the substituent $R^1$ of a compound of formula I using methods known in the art. Compounds of formula I-2 are conveniently obtained as the salt or the free base after basic aqueous work-up by treatment of compounds of formula I-1 (compounds of formula I in which $R^1$ is tert-butoxycarbonyl) with an acid in a suitable solvent like methanesulphonic acid in dichloromethane or tetrahydrofuran or hydrochloric acid in methanol. General scheme B is hereinafter further illustrated with general procedures XI and XII.

Scheme 3: General Scheme C

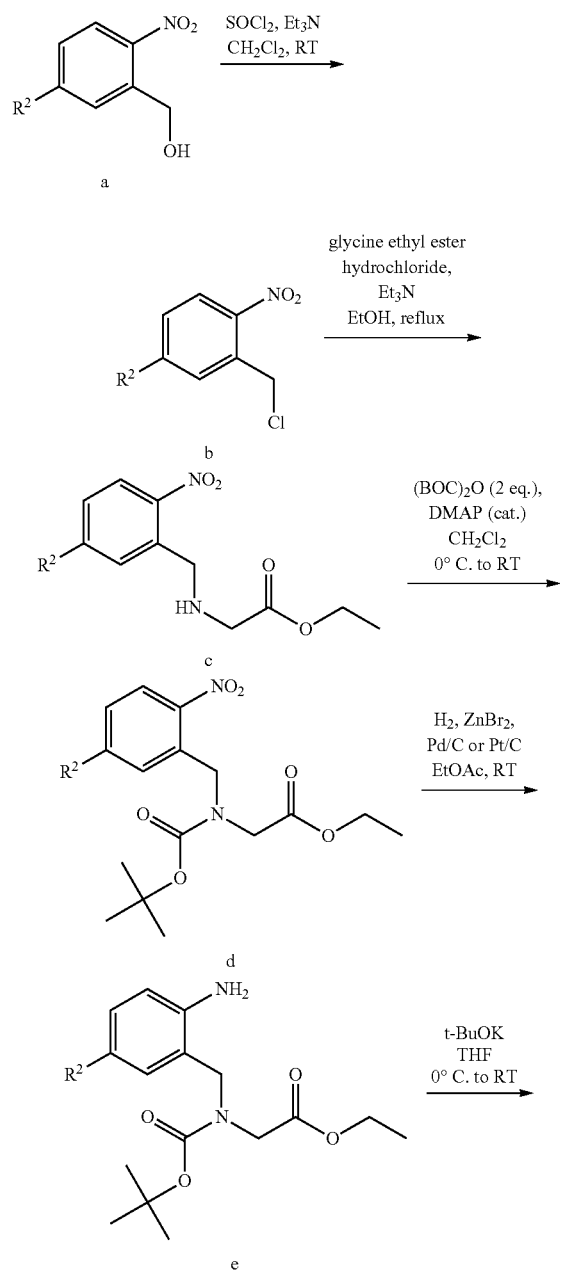

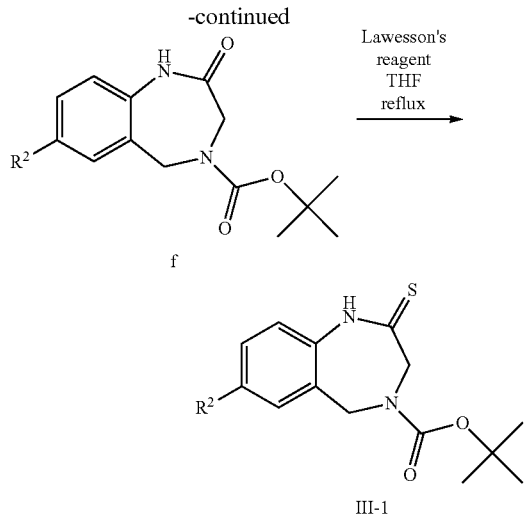

A thiolactam of formula III-1 (compounds of formula III in which $R^1$ is tert-butoxycarbonyl) can be obtained as follows: Transformation of a 2-nitrobenzyl alcohol of formula a to a benzylic chloride of formula b can be affected by a chlorinating reagent such as thionyl chloride in the presence of an organic tertiary amine base. Alkylation of a compound of formula b with glycine ethyl ester hydrochloride in the presence of an organic tertiary amine base and N-protection of the resulting compound of formula c using di-tert-butyl dicarbonate and a catalytic amount of 4-N,N-dimethylaminopyridine gives compounds of formula d. The nitro group can be reduced selectively by hydrogenation over palladium or platinum on charcoal, which has been pretreated with a zinc halide such as zinc bromide, to give aniline intermediates of formula e. Cyclization to lactams of formula f is achieved by treatment of compounds of formula e with a suitable base, e.g. potassium tert-butoxide, in tetrahydrofuran. A thiolactam of formula III-1 is obtained by treatment of a compound of formula f with Lawesson's reagent or phosphorous pentasulphide at elevated temperature.

Scheme 4: General Scheme D

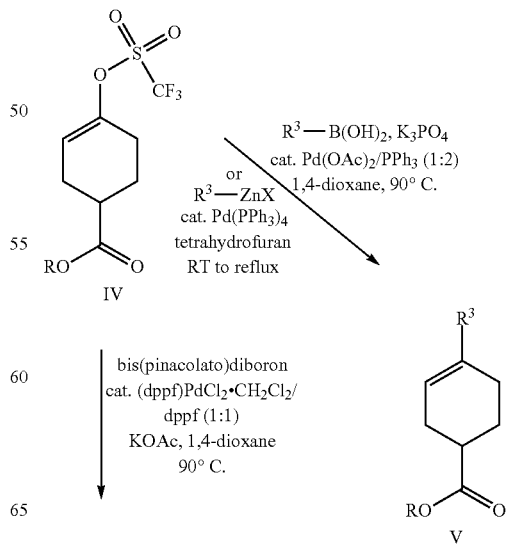

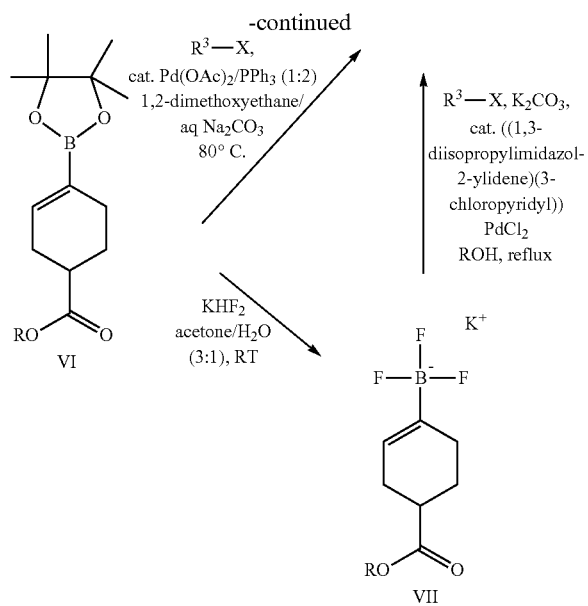

R = Me, Et
X = halogen
dppf = 1,1'-bis(diphenylphosphino)ferrocene

4-Heteroaryl-cyclohex-3-enecarboxylic acid ester intermediates of formula V can be prepared under the conditions of the Suzuki reaction from a 4-trifluoromethanesulfonyloxy-cyclohex-3-enecarboxylic acid ester of formula IV and a heteroaryl boronic acid, a heteroaryl boronic acid ester or a heteroaryl trifluoroborate salt in a suitable organic solvent such as 1,4-dioxane, 1,2-dimethoxyethane, tetrahydrofuran or toluene in the presence of catalytic amounts of a 1:2 mixture of palladium(II) acetate and triphenylphosphine or a 1:1 mixture of palladium(II) acetate and a bisphosphine ligand or tetrakis(triphenylphosphine)palladium(0) and in the presence of a base such as an alkali metal salt of phosphate or carbonate, which is used neat or as an aqueous solution, at a reaction temperature between room temperature and reflux. Alternatively 4-heteroaryl-cyclohex-3-enecarboxylic acid ester intermediates of formula V can be prepared under the conditions of the Negishi reaction from a 4-trifluoromethanesulfonyloxy-cyclohex-3-enecarboxylic acid ester of formula IV and a heteroaryl zinc halide in a suitable organic solvent such as tetrahydrofuran and Pd(PPh)$_3$ at a reaction temperature between room temperature and reflux. Alternatively compounds of formula V can be prepared by coupling a potassium trifluoroborate salt of formula VII with a heteroaryl halide $R^3$—X in the presence of a base such as potassium carbonate and a suitable palladium catalyst such as (1,3-diisopropylimidazol-2-ylidene)(3-chloropyridyl)palladium (II) chloride in a suitable solvent such as an alcohol at reflux. A potassium trifluoroborate salt of formula VII can be prepared by treatment of an (RS)-4-(4,4,5,5-tetramethyl-[1,3,2]dioxaborolan-2-yl)-cyclohex-3-enecarboxylic acid ester of formula VI with potassium hydrogen difluoride in a mixture of acetone and water at room temperature. Compounds of formula VI can be obtained by coupling a compound of formula IV with bis(pinacolato)diboron in the presence of a suitable base such as potassium acetate and a suitable palladium catalyst such as a 1:1 mixture of 1,1'-bis(diphenylphosphino)ferrocene and dichloro(1,1'-bis(diphenylphosphino) ferrocene) palladium(II) dichloromethane adduct in a suitable solvent such as 1,4-dioxane at 90° C. Compounds of formula V can alternatively be prepared under the conditions of the Suzuki reaction from a compound of formula VI and a heteroaryl halide $R^3$—X in a suitable organic solvent such as 1,4-dioxane, 1,2-dimethoxyethane, tetrahydrofuran or toluene in the presence of catalytic amounts of a 1:2 mixture of palladium(II) acetate and triphenylphosphine or a 1:1 mixture of palladium(II) acetate and a bisphosphine ligand or tetrakis(triphenylphosphine)palladium(0) and in the presence of a base such as an alkali metal salt of phosphate or carbonate, which is used neat or as an aqueous solution, at a reaction temperature between room temperature and reflux. General scheme D is hereinafter further illustrated with general procedures I to III.

Scheme 5: General Scheme E

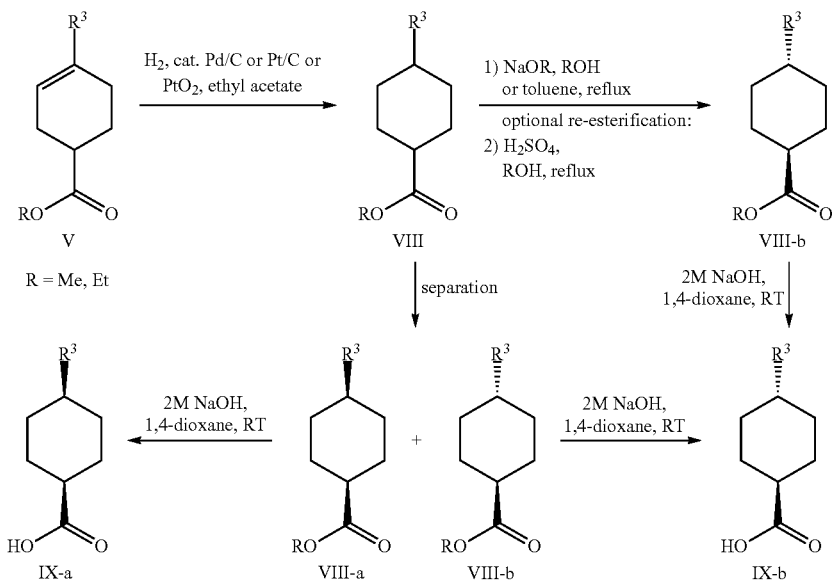

4-Heteroaryl-cyclohexane carboxylic acid ester intermediates of formula VIII are usually obtained as a mixture of the cis and the trans isomer by reduction of 4-heteroaryl-cyclohex-3-enyl carboxylic acid ester intermediates of formula V under an atmosphere of hydrogen gas (1 bar) in a suitable solvent such as ethyl acetate or an alcohol in the presence of a catalytic amount of palladium or platinum on charcoal or platinum(IV) oxide at room temperature. Compounds of formula V and VIII, the residue $R^3$ of which is substituted with one or more halide substituents other than fluorine may undergo partial or complete dehalogenation under these reaction conditions. The acid formed as a consequence of the dehalogenation reaction may be neutralized by addition of a base such as a trialkyl amine to the reaction mixture. Pretreatment of the palladium or platinum catalyst with a zinc halide may in some cases prevent or reduce dehalogenation of compounds of formula V and VIII, the residue $R^3$ of which is substituted with one or more halide substituents other than fluorine. Cis/trans mixtures of 4-heteroaryl-cyclohexane carboxylic acid ester intermediates of formula VIII may in some cases be separable by the usual methods such as silica gel column or high performance chromatography or crystallization into pure cis-4-heteroaryl-cyclohexane carboxylic acid ester intermediates of formula VIII-a and trans-4-heteroaryl-cyclohexane carboxylic acid ester intermediates of formula VIII-b, which can be saponified to pure cis-4-heteroaryl-cyclohexane carboxylic acid intermediates of formula IX-a and trans-4-heteroaryl-cyclohexane carboxylic acid intermediates of formula IX-b under standard conditions such as stirring in a mixture of aqueous sodium hydroxide solution and an etheral solvent such as 1,4-dioxane, tetrahydrofuran or diethyl ether a room temperature. Alternatively, trans-4-heteroaryl-cyclohexane carboxylic acid intermediates of formula IX-b can be obtained by epimerization of the cis isomer of cis/trans-mixtures of 4-heteroaryl-cyclohexane carboxylic acid ester intermediates of formula VIII using a suitable base, e.g. an alkali metal alkoxide such as sodium or potassium methylate or ethylate, in a suitable solvent such as methanol, ethanol or toluene at reflux followed by saponification of the crude reaction mixture, which may consist of a mixture of a trans-4-heteroaryl-cyclohexane carboxylic acid intermediate of formula IX-b and a trans-4-heteroaryl-cyclohexane carboxylic acid ester intermediate of formula VIII-b, under standard conditions such as stirring in a mixture of aqueous sodium hydroxide solution and an etheral solvent such as 1,4-dioxane, tetrahydrofuran or diethyl ether at room temperature. In case the epimerization reaction was carried out in an alcohol as solvent, the crude reaction mixture can alternatively be acidified by the addition of concentrated sulfuric acid and heated to reflux to obtain a trans-4-heteroaryl-cyclohexane carboxylic acid ester intermediate of formula VIII-b. General scheme E is hereinafter further illustrated with general procedures IV to VII.

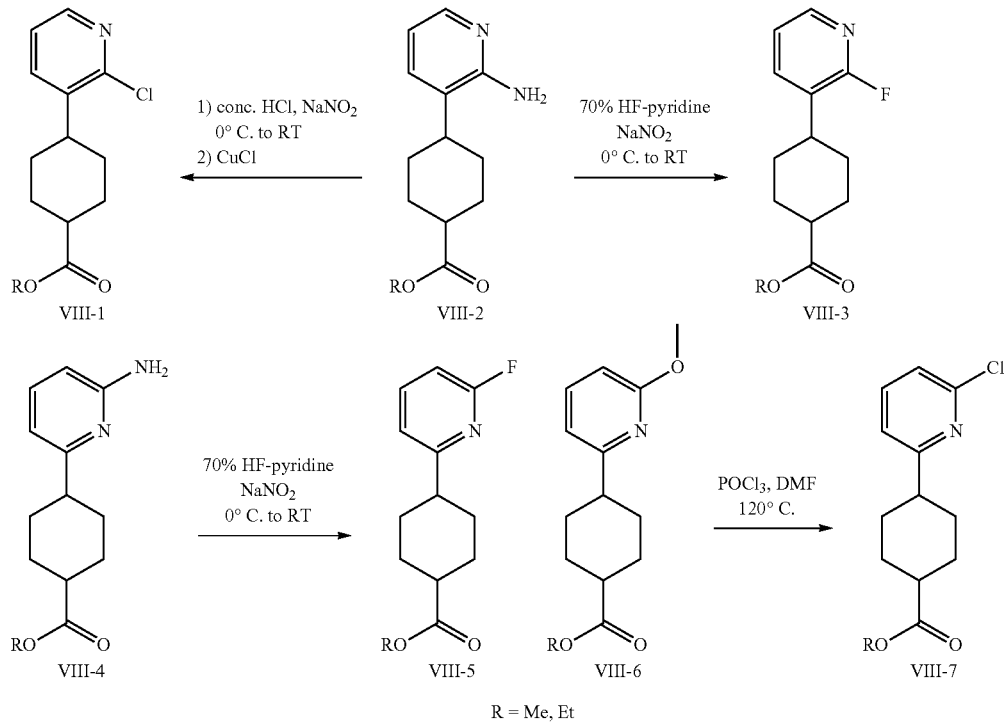

Scheme 6: General Scheme F

R = Me, Et

Compounds of formula VIII-1 (compounds of formula VIII, in which $R^3$ is a 2-chloro-pyridin-3-yl group) can be prepared from compounds of formula VIII-2 (compounds of formula VIII, in which $R^3$ is a 2-amino-pyridin-3-yl group) by consecutive treatment with a mixture of concentrated hydrochloric acid and sodium nitrite and copper(I) chloride. Compounds of formula VIII-2 can be converted to compounds of formula VIII-3 (compounds of formula VIII, in which $R^3$ is a 2-fluoro-pyridin-3-yl group) and compounds of formula VIII-4 (compounds of formula VIII, in which $R^3$ is a 6-amino-pyridin-2-yl group) can be converted to compounds of formula VIII-5 (compounds of formula VIII, in which $R^3$ is a 6-fluoro-pyridin-2-yl group) by treatment with 70% HF-pyridine and sodium nitrite. Compounds of formula VIII-7

(compounds of formula VIII, in which $R^3$ is a 6-chloro-pyridin-2-yl group) can be synthesized from compounds of formula VIII-6 (compounds of formula VIII, in which $R^3$ is a 6-methoxy-pyridin-2-yl group) by treatment with phosphorus oxy chloride in N,N-dimethylformamide at 120° C.

Scheme 6: General Scheme G

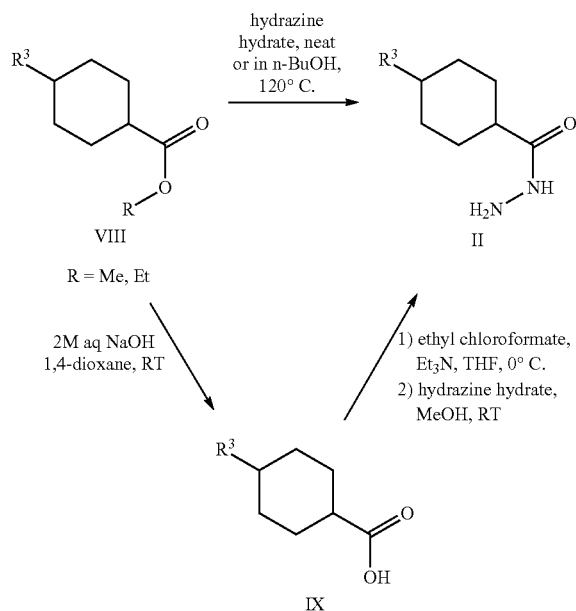

A 4-heteroaryl-cyclohexanecarboxylic acid ester intermediate of formula VIII can be converted to a hydrazide of formula II by heating with hydrazine hydrate. Alternatively, an ester of formula VIII can be hydrolyzed to a carboxylic acid of formula IX using a biphasic mixture of aqueous sodium or potassium hydroxide solution and an etheral solvent such as dioxane, tetrahydrofuran or diethyl ether. A hydrazide of formula II can be obtained by activating an acid intermediate of formula IX, e.g. with ethyl chloroformate, thionyl chloride, oxalylchloride or a peptide coupling reagent, and subsequent coupling with hydrazine. General scheme G is hereinafter further illustrated with general procedures VII to IX.

The corresponding pharmaceutically acceptable salts with acids can be obtained by standard methods known to the person skilled in the art, e.g. by dissolving the compound of formula I in a suitable solvent such as e.g. dioxan or THF and adding an appropriate amount of the corresponding acid. The products can usually be isolated by filtration or by chromatography. The conversion of a compound of formula I into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M is metal or ammonium cation and n is number of hydroxide anions, to a solution of the compound in a suitable solvent (e.g. ethanol, ethanol-water mixture, tetrahydrofuran-water mixture) and to remove the solvent by evaporation or lyophilisation.

Insofar as their preparation is not described in the examples, the compounds of formula I as well as all intermediate products can be prepared according to analogous methods or according to the methods set forth herein. Starting materials are commercially available, known in the art or can be prepared by methods known in the art or in analogy thereto.

It will be appreciated that the compounds of formula I in this invention can be derivatised at functional groups to provide derivatives which are capable of conversion back to the parent compound in vivo.

Pharmacological Tests

The compounds of the present invention exhibit V1a activity. They are selective inhibitors of the V1a receptor and are therefore likely to have a low potential to cause unwanted off-target related side-effects. The V1a activity can be detected as described below.

The human V1a receptor was cloned by RT-PCR from total human liver RNA. The coding sequence was subcloned in an expression vector after sequencing to confirm the identity of the amplified sequence. To demonstrate the affinity of the compounds from the present invention to the human V1a receptor binding studies were performed. Cell membranes were prepared from HEK293 cells transiently transfected with the expression vector and grown in 20 liter fermenters with the following protocol.

50 g of cells are resuspended in 30 ml freshly prepared ice cold Lyses buffer (50 mM HEPES, 1 mM EDTA, 10 mM magnesium dichloride adjusted to pH=7.4+complete cocktail of protease inhibitor (Roche Diagnostics)). Homogenized with Polytron for 1 min and solicited on ice for 2×2 minutes at 80% intensity (Vibrate solicitor). The preparation is centrifuged 20 min at 500 g at 4° C., the pellet is discarded and the supernatant centrifuged 1 hour at 43'000 g at 4° C. (19'000 rpm). The pellet is resuspended in 12.5 ml Lyses buffer+12.5 ml sucrose 20% and homogenized using a Polytron for 1-2 min. The protein concentration is determined by the Bradford method and aliquots are stored at −80° C. until use. For binding studies 60 mg Yttrium silicate SPA beads (Habersham®) are mixed with an aliquot of membrane in binding buffer (50 mM Tris, 120 mM sodium chloride, 5 mM potassium chloride, 2 mM calcium dichloride, 10 mM magnesium dichloride) for 15 minutes with mixing. 50 µl of bead/membrane mixture is then added to each well of a 96 well plate, followed by 50 µl of 4 nM 3H-Vasopressin (American Radiolabeled Chemicals). For total binding measurement 100 µl of binding buffer are added to the respective wells, for non-specific binding 100 µl of 8.4 mM cold vasopressin and for compound testing 100 µl of a serial dilution of each compound in 2% dimethyl sulfoxide. The plate is incubated 1 h at room temperature, centrifuged 1 min at 1000 g and counted on a Packard Top-Count. Non-specific binding counts are subtracted from each well and data is normalized to the maximum specific binding set at 100%. To calculate an $IC_{50}$ the curve is fitted using a non-linear regression model (XLfit) and the Ki is calculated using the Cheng-Prussoff equation.

The following representative data show the antagonistic activity against human V1a receptor of compounds according to present invention.

TABLE 3 human V1a pKi of selected examples

| Ex# | pKi (hV1a) |
|---|---|
| 1 | 8.72 |
| 2 | 8.00 |
| 3 | 9.10 |
| 4 | 9.70 |
| 5 | 7.86 |

TABLE 3-continued human V1a pKi of selected examples

| Ex# | pKi (hV1a) |
|---|---|
| 6 | 9.05 |
| 7 | 9.00 |
| 8 | 7.35 |
| 9 | 8.96 |
| 10 | 8.66 |
| 11 | 7.15 |
| 12 | 8.07 |
| 13 | 9.30 |
| 14 | 7.25 |
| 15 | 8.48 |
| 16 | 9.52 |
| 17 | 8.55 |
| 18 | 9.22 |
| 19 | 9.22 |
| 20 | 7.78 |
| 21 | 8.74 |
| 22 | 9.52 |
| 23 | 8.14 |
| 24 | 9.00 |
| 25 | 9.37 |
| 26 | 9.00 |
| 27 | 9.27 |
| 28 | 9.70 |
| 29 | 8.82 |
| 30 | 9.22 |
| 31 | 9.25 |
| 32 | 9.25 |
| 33 | 9.52 |
| 34 | 9.73 |
| 35 | 9.01 |
| 36 | 7.55 |
| 37 | 8.79 |
| 38 | 8.64 |
| 39 | 8.60 |
| 40 | 9.75 |
| 41 | 9.22 |
| 42 | 9.28 |
| 43 | 7.61 |
| 44 | 8.05 |
| 45 | 8.30 |
| 46 | 6.70 |
| 47 | 7.60 |
| 48 | 9.22 |
| 49 | 7.47 |
| 50 | 8.34 |
| 51 | 8.66 |
| 52 | 7.09 |
| 53 | 7.86 |
| 54 | 9.00 |
| 55 | 7.16 |
| 56 | 8.09 |
| 57 | 8.80 |
| 58 | 7.69 |
| 59 | 8.03 |
| 60 | 8.66 |
| 61 | 6.37 |
| 62 | 7.02 |
| 63 | 9.40 |
| 64 | 7.73 |
| 65 | 8.64 |
| 66 | 8.01 |
| 67 | 5.96 |
| 68 | 6.90 |
| 69 | 9.22 |
| 70 | 7.82 |
| 71 | 8.77 |
| 72 | 8.92 |
| 73 | 7.26 |
| 74 | 7.95 |
| 75 | 8.92 |
| 76 | 7.35 |
| 77 | 8.29 |
| 78 | 9.10 |
| 79 | 8.17 |
| 80 | 8.14 |
| 81 | 8.33 |
| 82 | 9.30 |
| 83 | 8.14 |
| 84 | 9.30 |
| 85 | 8.96 |
| 86 | 8.03 |
| 87 | 8.89 |

Pharmaceutical Compositions

The compounds of formula I as well as their pharmaceutically acceptable salts can be used in the form of pharmaceutical compositions. The pharmaceutical compositions can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injectable solutions.

The compounds of formula I and their pharmaceutically acceptable salts can be processed with pharmaceutically inert, inorganic or organic excipients for the production of tablets, coated tablets, dragées and hard gelatin capsules. Lactose, corn starch or derivatives thereof, talc, stearic acid or its salts etc can be used as such excipients e.g. for tablets, dragées and hard gelatin capsules. Suitable excipients for soft gelatin capsules are e.g. vegetable oils, waxes, fats, semisolid and liquid polyols etc.

Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage at which compounds of the invention can be administered can vary within wide limits and will, of course, be fitted to the individual requirements in each particular case. In general, in the case of oral administration a daily dosage of about 10 to 1000 mg per person of a compound of formula I should be appropriate, although the above upper limit can also be exceeded when necessary.

Examples of compositions according to the invention are, but are not limited to:

Example A

Tablets of the following composition are manufactured in the usual manner:

TABLE 4 possible tablet composition

| ingredient | mg/tablet | | | |
|---|---|---|---|---|
| | 5 | 25 | 100 | 500 |
| 1. compound of formula I | 5 | 25 | 100 | 500 |
| 2. lactose | 45 | 105 | 30 | 150 |

TABLE 4-continued possible tablet composition

| ingredient | mg/tablet | | | |
|---|---|---|---|---|
| | 5 | 25 | 100 | 500 |
| 3. corn starch | 15 | 6 | 6 | 60 |
| 4. microcrystalline cellulose | 34 | 30 | 30 | 450 |
| 5. magnesium stearate | 1 | 1 | 1 | 1 |
| total | 100 | 167 | 167 | 831 |

Manufacturing Procedure
1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Example B-1

Capsules of the following composition are manufactured:

TABLE 5 possible capsule ingredient composition

| ingredient | mg/capsule | | | | |
|---|---|---|---|---|---|
| | 5 | 10 | 25 | 100 | 500 |
| 1. compound of formula I | 5 | 10 | 25 | 100 | 500 |
| 2. lactose | 159 | 155 | 123 | 148 | — |
| 3. corn starch | 25 | 30 | 35 | 40 | 70 |
| 4. talc | 10 | 5 | 15 | 10 | 25 |
| 5. magnesium stearate | 1 | — | 2 | 2 | 5 |
| total | 200 | 200 | 200 | 300 | 600 |

Manufacturing Procedure
1. Mix ingredients 1, 2 and 3 in a suitable mixer for 30 minutes.
2. Add ingredients 4 and 5 and mix for 3 minutes.
3. Fill into a suitable capsule.

The compound of formula I, lactose and corn starch are firstly mixed in a mixer and then in a comminuting machine. The mixture is returned to the mixer, the talc (and magnesium stearate) is added thereto and mixed thoroughly. The mixture is filled by machine into suitable capsules, e.g. hard gelatin capsules.

Example B-2

Soft Gelatin Capsules of the following composition are manufactured:

TABLE 6 possible soft gelatin capsule ingredient composition

| ingredient | mg/capsule |
|---|---|
| compound of formula I | 5 |
| yellow wax | 8 |
| hydrogenated soybean oil | 8 |
| partially hydrogenated plant oils | 34 |
| soybean oil | 110 |
| total | 165 |

TABLE 7 possible soft gelatin capsule composition

| ingredient | mg/capsule |
|---|---|
| gelatin | 75 |
| glycerol 85% | 32 |
| karion 83 | 8 (dry matter) |
| titanium dioxide | 0.4 |
| iron oxide yellow | 1.1 |
| total | 116.5 |

Manufacturing Procedure

The compound of formula I is dissolved in a warm melting of the other ingredients and the mixture is filled into soft gelatin capsules of appropriate size. The filled soft gelatin capsules are treated according to the usual procedures.

Example C

Suppositories of the following composition are manufactured:

TABLE 8 possible suppository composition

| ingredient | mg/supp. |
|---|---|
| compound of formula I | 15 |
| suppository mass | 1285 |
| total | 1300 |

Manufacturing Procedure

The suppository mass is melted in a glass or steel vessel, mixed thoroughly and cooled to 45° C. Thereupon, the finely powdered compound of formula I is added thereto and stirred until it has dispersed completely. The mixture is poured into suppository moulds of suitable size, left to cool; the suppositories are then removed from the moulds and packed individually in wax paper or metal foil.

Example D

Injection solutions of the following composition are manufactured:

TABLE 9 possible injection solution composition

| ingredient | mg/injection solution. |
|---|---|
| compound of formula I | 3 |
| polyethylene Glycol 400 | 150 |
| acetic acid | q.s. ad pH 5.0 |
| water for injection solutions | ad 1.0 ml |

Manufacturing Procedure

The compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example E

Sachets of the following composition are manufactured:

TABLE 10

| possible sachet composition | |
|---|---|
| ingredient | mg/sachet |
| compound of formula I | 50 |
| lactose, fine powder | 1015 |
| microcrystalline cellulose (AVICEL PH 102) | 1400 |
| sodium carboxymethyl cellulose | 14 |
| polyvinylpyrrolidon K 30 | 10 |
| magnesium stearate | 10 |
| flavoring additives | 1 |
| total | 2500 |

Manufacturing Procedure

The compound of formula I is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

EXAMPLES

The following examples are provided for illustration of the invention. They should not be considered as limiting the scope of the invention, but merely as being representative thereof.

Intermediate of Formula IV (RS)-4-Trifluoromethanesulfonyloxy-cyclohex-3-enecarboxylic acid ethyl ester

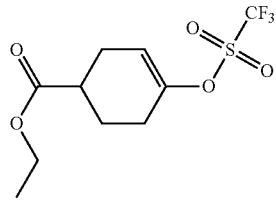 [SMILES: CCOC(=O)C1CC=C(OS(=O)(=O)C(F)(F)F)CC1]

To a solution of ethyl-4-cyclohexanonecarboxylate (25.0 g, 147 mmol) in tetrahydrofuran (580 ml) was added a 1M solution of lithium bis(trimethylsilyl)amid in tetrahydrofuran (154 ml, 154 mmol) at −78° C. Stirring for 1 h was followed by addition of a solution of N-phenyl-bis(trifluoromethanesulfonimide) (55.1 g, 154 mmol) in tetrahydrofuran (80 ml). The cooling bath was removed 30 minutes after completed addition, and the reaction mixture was stirred for 12 h at room temperature. The mixture was quenched with 1 M aqueous sodium hydrogen sulfate solution (154 ml, 154 mmol). The solvent was removed by rotary evaporation (water bath of 40° C.). The residue was partitioned between tert-butyl methyl ether (500 ml) and 0.5 M aqueous sodium hydroxide solution (400 ml). The organic layer was washed with two 400-ml portions of 0.5 M aqueous sodium hydroxide solution, one 200-ml portion of saturated ammonium chloride solution and one 100-ml portion of brine, dried over anhydrous sodium sulfate and concentrated in vacuo to give the title compound (41.8 g, 94.2%) as yellow oil, which was used in the following steps without further purification. MS m/e: 273 ([M-$C_2H_5$]$^-$).

Intermediate of Formula (VI)

(RS)-4-(4,4,5,5-Tetramethyl-[1,3,2]dioxaborolan-2-yl)-cyclohex-3-enecarboxylic acid ethyl ester

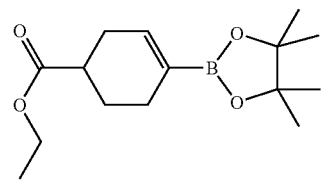 [SMILES: CCOC(=O)C1CC=C(B2OC(C)(C)C(C)(C)O2)CC1]

A mixture of (RS)-4-trifluoromethanesulfonyloxy-cyclohex-3-enecarboxylic acid ethyl ester (3.0 g, 9.92 mmol), potassium acetate (2.92 g, 29.8 mmol) and bis(pinacolato) diboron (3.78 g, 14.9 mmol) in 1,4-dioxane (30 ml) was purged with argon. Addition of 1,1'-bis(diphenylphosphino) ferrocene (0.17 g, 0.30 mmol) and dichloro(1,1'-bis(diphenylphosphino) ferrocene)palladium(II) dichloromethane adduct (0.22 g, 0.30 mmol) was followed by stirring at 90° C. for 18 h. The reaction mixture was partitioned between ethyl acetate (200 ml) and water (150 ml). The layers were separated. The organic layer was washed with one portion of brine, dried over anhydrous sodium sulfate and concentrated to dryness. Flash-chromatography with n-heptane/ethyl acetate as eluent gave the title compound (1.95 g, 70%) as light yellow oil. MS m/e: 281 ([M+H]$^+$)

Intermediate of Formula (VII)

Potassium (RS)-(4-(ethoxycarbonyl)cyclohex-1-enyl)trifluoroborate

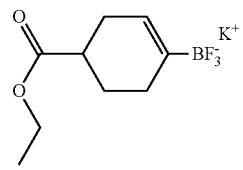

To a solution of (RS)-4-(4,4,5,5-tetramethyl-[1,3,2]dioxaborolan-2-yl)-cyclohex-3-enecarboxylic acid ethyl ester (0.37 g, 1.32 mmol) in acetone (9 ml) and water (3 ml) was added potassium hydrogen difluoride (0.41 g, 5.28 mmol). Stirring for 4 h at room temperature was followed by evaporation of the solvent mixture. The residue was triturated in warm acetonitrile (20 ml). The solids were removed by filtration. The filtrate was concentrated to dryness to give the title compound (0.35 g, quantitative) as white solid which was used without further purification in the next step.

4-Heteroaryl-cyclohex-3-enecarboxylic acid ester intermediates of formula (V)

General Procedure (I)

A mixture of (RS)-4-trifluoromethanesulfonyloxy-cyclohex-3-enecarboxylic acid ethyl ester (1 eq), a heteroaryl zinc halide (1-1.2 eq) and tetrakis(triphenylphosphine)palladium (0.05 eq) in dry tetrahydrofuran (0.3 M) is stirred at reflux for 14-20 h. After cooling to room temperature the reaction mixture is partitioned between an organic solvent such as tert-butyl methyl ether or ethyl acetate and water. The layers are separated. The aqueous layer is extracted with two or three portions of organic solvent. The combined organic layers are dried over anhydrous sodium sulfate and concentrated to dryness. Purification by flash-chromatography gives a 4-heteroaryl-cyclohex-3-enecarboxylic acid ester intermediate of formula (V).

General Procedure (II)

A mixture of (RS)-4-(4,4,5,5-tetramethyl-[1,3,2]dioxaborolan-2-yl)-cyclohex-3-enecarboxylic acid ethyl ester (1 eq) and a heteroaryl halide (1.3 eq) in a 4:1 mixture of 1,2-dimethoxyethane and 2M aqueous sodium carbonate solution (0.3 M) is purged with argon. After consecutive addition of triphenylphosphine (0.1 eq) and palladium(II) acetate (0.05 eq) the mixture is stirred at 80° C. for 20 h. After cooling to room temperature the reaction mixture is partitioned between an organic solvent such as tert-butyl methyl ether or ethyl acetate and water. The layers are separated. The aqueous layer is extracted with two or three portions of organic solvent. The combined organic layers are dried over anhydrous sodium sulfate and concentrated to dryness. Purification by flash-chromatography gives a4-heteroaryl-cyclohex-3-enecarboxylic acid ester intermediate of formula (V).

General Procedure (III)

To a mixture of potassium (RS)-(4-(ethoxycarbonyl)cyclohex-1-enyl)trifluoroborate (1 eq), a heteroaryl halide (1.2 eq) and potassium carbonate (3 eq) in an alcohol such as ethanol or methanol (0.2 M) is added (1,3-diisopropylimidazol-2-ylidene)(3-chloropyridyl)palladium (II) chloride (0.02 eq). The mixture is stirred at reflux for 1-20 h. After cooling to room temperature the solvent is evaporated. The residue is triturated in an organic solvent such as tert-butyl methyl ether or ethyl acetate. The precipitates are removed by filtration. The filtrate is concentrated to dryness. Purification by flash-chromatography gives a 4-heteroaryl-cyclohex-3-enecarboxylic acid ester intermediate of formula (V).

4-Heteroaryl-cyclohex-3-enecarboxylic acid ester 1

(RS)-4-Pyridin-2-yl-cyclohex-3-enecarboxylic acid ethyl ester

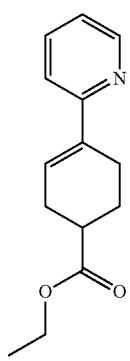 [SMILES: CCOC(=O)C1CC=C(c2ccccn2)CC1]

The title compound was obtained as colorless oil in 63% yield from 2-pyridylzinc bromide according to general procedure (I). MS m/e: 232 ([M+H]$^+$)

4-Heteroaryl-cyclohex-3-enecarboxylic acid ester 2

(RS)-4-(6-Methyl-pyridin-2-yl)-cyclohex-3-enecarboxylic acid ethyl ester

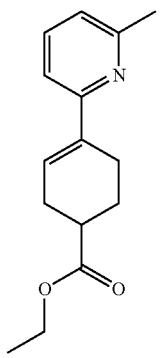 [SMILES: CCOC(=O)C1CC=C(c2cccc(C)n2)CC1]

The title compound was obtained as colorless liquid in 56% yield from 2-methyl-6-pyridylzinc bromide according to general procedure (I). MS m/e: 246 ([M+H]$^+$)

4-Heteroaryl-cyclohex-3-enecarboxylic acid ester 3

(RS)-4-(6-Ethyl-pyridin-2-yl)-cyclohex-3-enecarboxylic acid ethyl ester

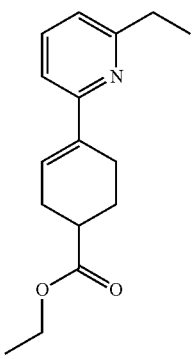 [SMILES: CCOC(=O)C1CC=C(c2cccc(CC)n2)CC1]

The title compound was obtained as yellow oil in 35% yield from 2-ethyl-6-pyridylzinc chloride according to general procedure (I). MS m/e: 260 ([M+H]⁺)

4-Heteroaryl-cyclohex-3-enecarboxylic acid ester 4

(RS)-4-(6-Isopropyl-pyridin-2-yl)-cyclohex-3-enecarboxylic acid ethyl ester

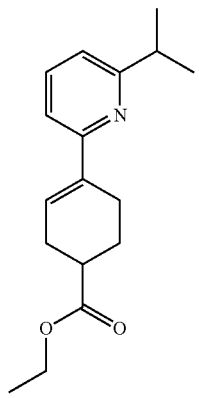 [SMILES: CCOC(=O)C1CC=C(c2cccc(C(C)C)n2)CC1]

The title compound was obtained as yellow liquid in 55% yield from 2-isopropyl-6-pyridylzinc chloride according to general procedure (I). MS m/e: 274 ([M+H]⁺)

4-Heteroaryl-cyclohex-3-enecarboxylic acid ester 5

(RS)-4-(6-Methoxy-pyridin-2-yl)-cyclohex-3-enecarboxylic acid ethyl ester

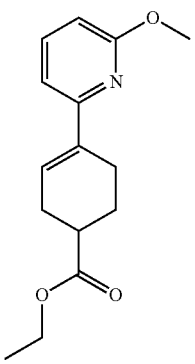 [SMILES: CCOC(=O)C1CC=C(c2cccc(OC)n2)CC1]

The title compound was obtained as light yellow liquid in 86% yield from 2-bromo-6-methoxypyridine according to general procedure (III). MS m/e: 262 ([M+H]⁺)

4-Heteroaryl-cyclohex-3-enecarboxylic acid ester 6

(RS)-4-(6-Amino-pyridin-2-yl)-cyclohex-3-enecarboxylic acid ethyl ester

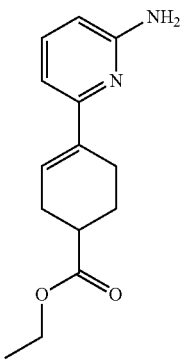 [SMILES: CCOC(=O)C1CC=C(c2cccc(N)n2)CC1]

The title compound was obtained as light yellow liquid in 86% yield from 2-bromo-6-aminopyridine according to general procedure (III). MS m/e: 247 ([M+H]⁺)

4-Heteroaryl-cyclohex-3-enecarboxylic acid ester 7

(RS)-4-(5-Fluoro-pyridin-2-yl)-cyclohex-3-enecarboxylic acid ethyl ester

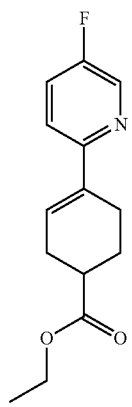

The title compound was obtained as colorless oil in 86% yield from 2-bromo-5-fluoropyridine according to general procedure (III). MS m/e: 250 ([M+H]$^+$)

4-Heteroaryl-cyclohex-3-enecarboxylic acid ester 8

(RS)-4-(4-Amino-pyridin-2-yl)-cyclohex-3-enecarboxylic acid ethyl ester

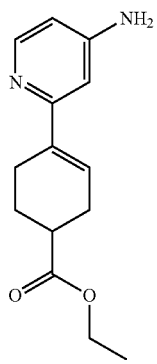 [SMILES: CCOC(=O)C1CC=C(c2cc(N)ccn2)CC1]

The title compound was obtained as light yellow oil in 40% yield from 2-chloro-4-aminopyridine according to general procedure (III). MS m/e: 247 ([M+H]$^+$)

4-Heteroaryl-cyclohex-3-enecarboxylic acid ester 9

(RS)-4-(3-Fluoro-pyridin-2-yl)-cyclohex-3-enecarboxylic acid ethyl ester

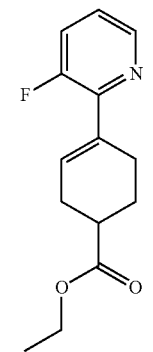

The title compound was obtained as colorless oil in 89% yield from 2-bromo-3-fluoropyridine according to general procedure (III). MS m/e: 250 ([M+H]$^+$)

4-Heteroaryl-cyclohex-3-enecarboxylic acid ester 10

(RS)-4-Pyridin-3-yl-cyclohex-3-enecarboxylic acid ethyl ester

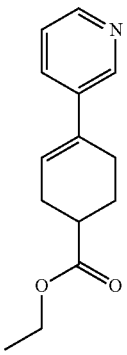

The title compound was obtained as colorless oil in 82% yield from 3-bromopyridine according to general procedure (III). MS m/e: 232 ([M+H]$^+$)

4-Heteroaryl-cyclohex-3-enecarboxylic acid ester 11

(RS)-4-(2-Amino-pyridin-3-yl)-cyclohex-3-enecarboxylic acid ethyl ester

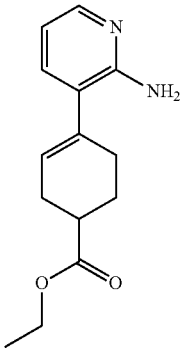 [SMILES: CCOC(=O)C1CC=C(c2cccnc2N)CC1]

The title compound was obtained as colorless oil in 60% yield from 2-amino-3-bromopyridine according to general procedure (III). MS m/e: 247 ([M+H]$^+$)

4-Heteroaryl-cyclohex-3-enecarboxylic acid ester 12

(RS)-4-Pyrimidin-2-yl-cyclohex-3-enecarboxylic acid ethyl ester

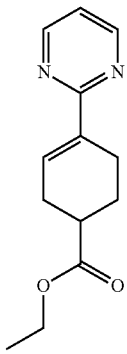 [SMILES: CCOC(=O)C1CC=C(c2ncccn2)CC1]

The title compound was obtained as light yellow oil in 47% yield from 3-bromopyrimidine according to general procedure (II). MS m/e: 233 ([M+H]$^+$)

4-Heteroaryl-cyclohex-3-enecarboxylic acid ester 13

(RS)-4-(4,6-Dimethyl-pyrimidin-2-yl)-cyclohex-3-enecarboxylic acid ethyl ester

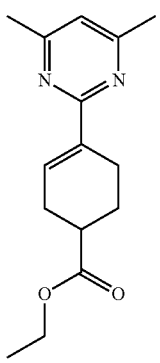

The title compound was obtained as white solid in 65% yield from 2-chloro-4,6-dimethyl-pyrimidine according to general procedure (III). MS m/e: 261 ([M+H]$^+$)

4-Heteroaryl-cyclohex-3-enecarboxylic acid ester 14

(RS)-4-(2-Methyl-pyrimidin-4-yl)-cyclohex-3-enecarboxylic acid ethyl ester

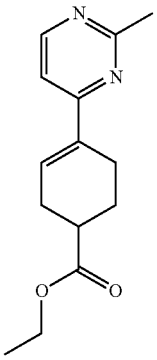 [SMILES: CCOC(=O)C1CC=C(c2ccnc(C)n2)CC1]

The title compound was obtained as colorless oil in 52% yield from 4-chloro-2-methylpyrimidine according to general procedure (III). MS m/e: 247 ([M+H]$^+$)

4-Heteroaryl-cyclohex-3-enecarboxylic acid ester 15

(RS)-4-(3-Chloro-pyrazin-2-yl)-cyclohex-3-enecarboxylic acid ethyl ester

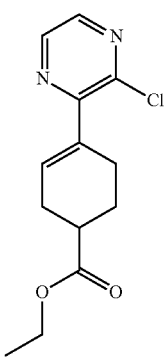 [SMILES: CCOC(=O)C1CC=C(c2nccnc2Cl)CC1]

The title compound was obtained as colorless oil in 52% yield from 2,3-dichloropyrazine according to general procedure (III). MS m/e: 267 ([M+H]$^+$)

4-Heteroaryl-cyclohex-3-enecarboxylic acid ester 16

(RS)-4-(6-Methyl-pyrazin-2-yl)-cyclohex-3-enecarboxylic acid ethyl ester

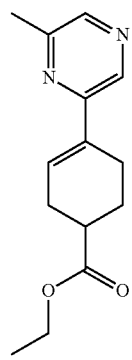 [SMILES: CCOC(=O)C1CC=C(c2cncc(C)n2)CC1]

The title compound was obtained as yellow oil in 73% yield from 2-chloro-6-methylpyrazine according to general procedure (III). MS m/e: 247 ([M+H]$^+$)

4-Heteroaryl-cyclohex-3-enecarboxylic acid ester 17

(RS)-4-(3-Methyl-pyrazin-2-yl)-cyclohex-3-enecarboxylic acid ethyl ester

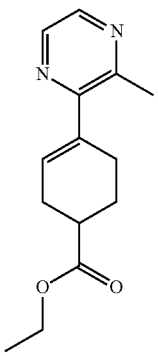 [SMILES: CCOC(=O)C1CC=C(c2nccnc2C)CC1]

The title compound was obtained as light yellow oil in 41% yield from 2-chloro-3-methylpyrazine according to general procedure (III). MS m/e: 247 ([M+H]$^+$)

4-Heteroaryl-cyclohex-3-enecarboxylic acid ester 18

(RS)-4-(3,6-Dimethyl-pyrazin-2-yl)-cyclohex-3-enecarboxylic acid ethyl ester

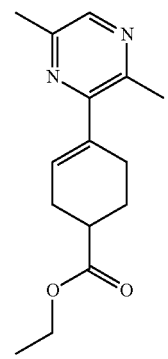 [SMILES: CCOC(=O)C1CC=C(c2nc(C)cnc2C)CC1]

The title compound was obtained as yellow oil in 76% yield from 2-chloro-3,6-dimethylpyrazine according to general procedure (III). MS m/e: 261 ([M+H]$^+$)

4-Heteroaryl-cyclohex-3-enecarboxylic acid ester 19

(RS)-4-(6-Chloro-pyridazin-3-yl)-cyclohex-3-enecarboxylic acid ethyl ester

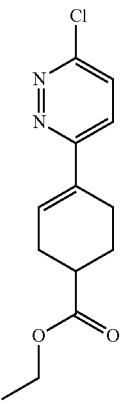 [SMILES: CCOC(=O)C1CC=C(c2ccc(Cl)nn2)CC1]

The title compound was obtained as light brown solid in 64% yield from 3,6-dichloropyridazine according to general procedure (III). MS m/e: 267 ([M+H]+)

4-Heteroaryl-cyclohex-3-enecarboxylic acid ester 20

(RS)-4-(3-Amino-pyridin-2-yl)-cyclohex-3-enecarboxylic acid ethyl ester

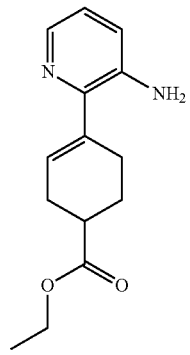 [SMILES: CCOC(=O)C1CC=C(c2ncccc2N)CC1]

The title compound was obtained as light yellow solid in 65% yield from 3-amino-2-chloropyridine according to general procedure (III). MS m/e: 247 ([M+H]+)

4-Heteroaryl-cyclohex-3-enecarboxylic acid ester 21

(RS)-4-(3,5-Difluoro-pyridin-2-yl)-cyclohex-3-enecarboxylic acid ethyl ester

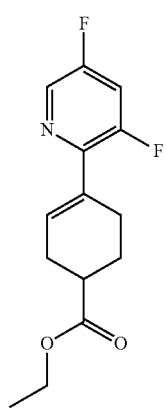 [SMILES: CCOC(=O)C1CC=C(c2ncc(F)cc2F)CC1]

The title compound was obtained as colorless oil in 61% yield from 2-bromo-3,5-difluoropyridine according to general procedure (III). MS m/e: 268 ([M+H]+)

4-Heteroaryl-cyclohexanecarboxylic acid ester intermediates of formula (VIII)

General Procedure (IV)

Platinum(IV) Oxide Catalyzed Hydrogenation

A solution of a 4-heteroaryl-cyclohex-3-enecarboxylic acid ester intermediate of formula V in ethyl acetate (0.1 M) is purged with argon. Addition of platinum(IV) oxide (0.3 eq) is followed by filling the flask with hydrogen. The reaction mixture is stirred at room temperature under an atmosphere of hydrogen (1 bar) for 1-16 h. The catalyst is removed by filtration over Decalite®. The filtrate is concentrated to dryness to give a cis/trans mixture of a crude 4-heteroaryl-cyclohexanecarboxylic acid ester intermediate of formula VIII, which can usually be used in the next step without further purification.

General Procedure (V)

Palladium on Charcoal Catalyzed Hydrogenation

A solution of a 4-heteroaryl-cyclohex-3-enecarboxylic acid ester intermediate of formula V and optionally an base such as triethylamine (1 eq) in an organic solvent such as ethyl acetate or toluene (0.1 M) is purged with argon. Addition of 10% palladium on activated charcoal (0.05 eq) is followed by filling the flask with hydrogen. The reaction mixture is stirred at room temperature under an atmosphere of hydrogen (1 bar) for 20-72 h. The catalyst is removed by filtration over Decalite®. The filtrate is washed with one portion of water. The aqueous layer is extracted with one or two portions of ethyl acetate. The combined organic layers are dried over anhydrous sodium sulfate and concentrated to dryness to give a cis/trans mixture of a crude 4-heteroaryl-cyclohexanecarboxylic acid ester intermediate of formula VIII, which can usually be used in the next step without further purification.

General Procedure (VI)

Epimerization

A mixture of cis/trans-4-heteroaryl-cyclohexanecarboxylic acid ester intermediate of formula VIII and sodium ethylate (3-6 eq) in ethanol is heated at reflux for 20-72 h. Under these reaction conditions partial saponification of the resulting trans-4-heteroaryl-cyclohexanecarboxylic acid ester intermediate of formula VIII-b to a trans-4-heteroaryl-cyclohexanecarboxylic acid intermediate of formula IX-b may occur. Such a trans-4-heteroaryl-cyclohexanecarboxylic acid intermediate of formula IX-b can be reconverted to a trans-4-heteroaryl-cyclohexanecarboxylic acid ester intermediate of formula VIII-b by consecutive cooling of the mixture to 0-5° C., addition of concentrated sulfuric acid (7-9 eq) and heating of the mixture at reflux for 1-2 h. After cooling to room temperature the reaction mixture is partitioned between an organic solvent such as ethyl acetate or tert-butyl methyl ether and 2M aqueous sodium carbonate solution. The layers are separated. The aqueous layer is extracted with two or three portions of organic solvent. The combined organic layers are dried over anhydrous sodium sulfate and concentrated to dryness. Purification by flash-chromatography gives a trans-4-heteroaryl-cyclohexanecarboxylic acid ester intermediate of formula VIII-b.

4-Heteroaryl-cyclohexanecarboxylic acid ester intermediate 1 cis/trans-4-Pyridin-2-yl-cyclohexanecarboxylic acid ethyl ester

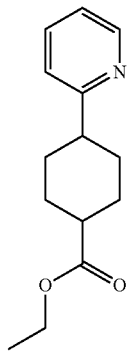 [SMILES: CCOC(=O)C1CCC(c2ccccn2)CC1]

The title compound was obtained as colorless oil in quantitative yield from (RS)-4-pyridin-2-yl-cyclohex-3-enecarboxylic acid ethyl ester according to general procedure (IV). MS m/e: 234 ([M+H]$^+$)

4-Heteroaryl-cyclohexanecarboxylic acid ester intermediate 2 trans-4-Pyridin-2-yl-cyclohexanecarboxylic acid ethyl ester

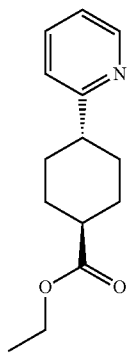 [SMILES: CCOC(=O)[C@H]1CC[C@H](c2ccccn2)CC1]

The title compound was obtained as light brown oil in 86% yield from cis/trans-4-pyridin-2-yl-cyclohexanecarboxylic acid ethyl ester according to general procedure (VI). MS m/e: 234 ([M+H]$^+$)

4-Heteroaryl-cyclohexanecarboxylic acid ester intermediate 3 cis/trans-4-(6-Methyl-pyridin-2-yl)-cyclohexanecarboxylic acid ethyl ester

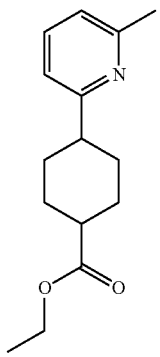 [SMILES: CCOC(=O)C1CCC(c2cccc(C)n2)CC1]

The title compound was obtained as colorless liquid in 98% yield from ((RS)-4-(6-methyl-pyridin-2-yl)-cyclohex-3-enecarboxylic acid ethyl ester according to general procedure (IV). MS m/e: 248 ([M+H]$^+$)

4-Heteroaryl-cyclohexanecarboxylic acid ester intermediate 4 trans-4-(6-Methyl-pyridin-2-yl)-cyclohexanecarboxylic acid ethyl ester

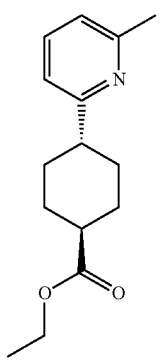 [SMILES: CCOC(=O)[C@H]1CC[C@H](c2cccc(C)n2)CC1]

The title compound was obtained as light yellow liquid in quantitative yield from cis/trans-4-(6-methyl-pyridin-2-yl)- cyclohexanecarboxylic acid ethyl ester according to general procedure (VI). MS m/e: 248 ([M+H]$^+$)

4-Heteroaryl-cyclohexanecarboxylic acid ester intermediate 5 cis/trans-4-(6-Ethyl-pyridin-2-yl)-cyclohexanecarboxylic acid ethyl ester

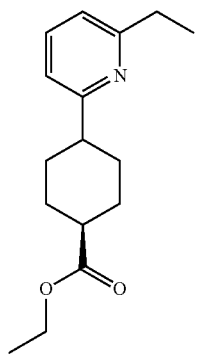

The title compound was obtained as colorless liquid in 97% yield from ((RS)-4-(6-ethyl-pyridin-2-yl)-cyclohex-3-enecarboxylic acid ethyl ester according to general procedure (IV). MS m/e: 262 ([M+H]$^+$)

4-Heteroaryl-cyclohexanecarboxylic acid ester intermediate 6 trans-4-(6-Ethyl-pyridin-2-yl)-cyclohexanecarboxylic acid ethyl ester

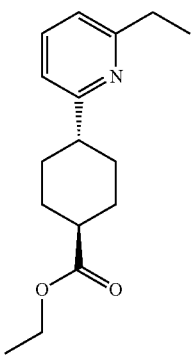 [SMILES: CCOC(=O)[C@H]1CC[C@H](c2cccc(CC)n2)CC1]

The title compound was obtained as colorless oil in 59% yield from cis/trans-4-(6-ethyl-pyridin-2-yl)-cyclohexanecarboxylic acid ethyl ester according to general procedure (VI). MS m/e: 262 ([M+H]$^+$)

4-Heteroaryl-cyclohexanecarboxylic acid ester intermediate 7 cis/trans-4-(6-Isopropyl-pyridin-2-yl)-cyclohexanecarboxylic acid ethyl ester (2:1)

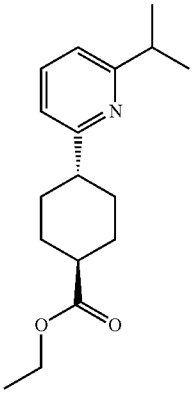 [SMILES: CCOC(=O)[C@H]1CC[C@H](c2cccc(C(C)C)n2)CC1]

The title compound was obtained as colorless liquid in 97% yield from ((RS)-4-(6-isoproyl-pyridin-2-yl)-cyclohex-3-enecarboxylic acid ethyl ester according to general procedure (IV). MS m/e: 276 ([M+H]$^+$)

4-Heteroaryl-cyclohexanecarboxylic acid ester intermediate 8 trans-4-(6-Isopropyl-pyridin-2-yl)-cyclohexanecarboxylic acid ethyl ester

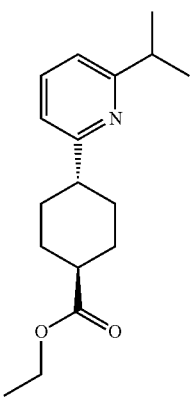 [SMILES: CCOC(=O)[C@H]1CC[C@H](c2cccc(C(C)C)n2)CC1]

The title compound was obtained as yellow oil in 61% yield from cis/trans-4-(6-isopropyl-pyridin-2-yl)-cyclohexanecarboxylic acid ethyl ester according to general procedure (VI). MS m/e: 276 ([M+H]⁺)

4-Heteroaryl-cyclohexanecarboxylic acid ester intermediate 9 cis/trans-4-(6-Methoxy-pyridin-2-yl)-cyclohexanecarboxylic acid ethyl ester

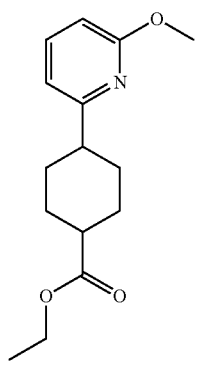 [SMILES: CCOC(=O)C1CCC(c2cccc(OC)n2)CC1]

The title compound was obtained as colorless liquid in 95% yield from (RS)-4-(6-methoxy-pyridin-2-yl)-cyclohex-3-enecarboxylic acid ethyl ester according to general procedure (V). MS m/e: 264 ([M+H]⁺)

4-Heteroaryl-cyclohexanecarboxylic acid ester intermediate 10 trans-4-(6-Methoxy-pyridin-2-yl)-cyclohexanecarboxylic acid ethyl ester

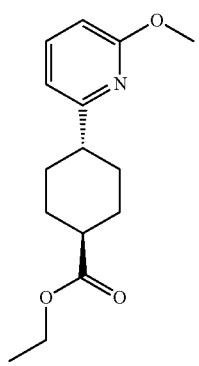 [SMILES: CCOC(=O)[C@H]1CC[C@H](c2cccc(OC)n2)CC1]

The title compound was obtained as light brown oil in quantitative yield from cis/trans-4-(6-methoxy-pyridin-2-yl)-cyclohexanecarboxylic acid ethyl ester according to general procedure (VI). MS m/e: 264 ([M+H]⁺)

4-Heteroaryl-cyclohexanecarboxylic acid ester intermediate 11 trans-4-(6-Chloro-pyridin-2-yl)-cyclohexanecarboxylic acid ethyl ester

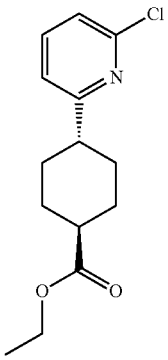 [SMILES: CCOC(=O)[C@H]1CC[C@H](c2cccc(Cl)n2)CC1]

To a solution of trans-4-(6-methoxy-pyridin-2-yl)-cyclohexanecarboxylic acid ethyl ester (0.55 g, 2.1 mmol) in N,N-dimethylformamide (21 ml) was added phosphorus oxychloride (0.96 ml, 10 mmol) at room temperature. Stirring for 2 h at 90° C. was followed by stirring for 24 h at 120° C. After cooling to room temperature the reaction mixture was poured onto crushed ice, stirred for 10 minutes and extracted with three 100-ml portions of ethyl acetate. The combined organic layers were washed with two 50-ml portions of water and one 50-ml portion of brine, dried over anhydrous sodium sulfate and concentrated to dryness. Purification by flash-chromatography gave the title compound (0.20 g, 36%) as light yellow oil. MS m/e: 268 ([M+H]⁺)

4-Heteroaryl-cyclohexanecarboxylic acid ester intermediate 12 cis/trans-4-(6-Amino-pyridin-2-yl)-cyclohexanecarboxylic acid ethyl ester (2:1)

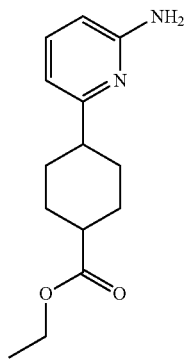 [SMILES: CCOC(=O)C1CCC(c2cccc(N)n2)CC1]

The title compound was obtained as colorless liquid in 95% yield from (RS)-4-(6-amino-pyridin-2-yl)-cyclohex-3-enecarboxylic acid ethyl ester according to general procedure (V). MS m/e: 249 ([M+H]$^+$)

4-Heteroaryl-cyclohexanecarboxylic acid ester intermediate 13 trans-4-(6-Amino-pyridin-2-yl)-cyclohexanecarboxylic acid ethyl ester

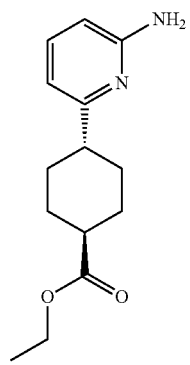 [SMILES: CCOC(=O)[C@H]1CC[C@H](c2cccc(N)n2)CC1]

The title compound was obtained as light yellow solid in 74% yield from cis/trans-4-(6-amino-pyridin-2-yl)-cyclohexanecarboxylic acid ethyl ester according to general procedure (VI). MS m/e: 248 ([M+H]$^+$)

4-Heteroaryl-cyclohexanecarboxylic acid ester intermediate 14 trans-4-(6-Fluoro-pyridin-2-yl)-cyclohexanecarboxylic acid ethyl ester

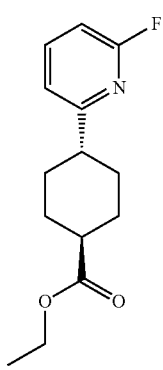 [SMILES: CCOC(=O)[C@H]1CC[C@H](c2cccc(F)n2)CC1]

Batch 1: To a solution of trans-4-(6-amino-pyridin-2-yl)-cyclohexanecarboxylic acid ethyl ester (0.050 g, 0.20 mmol) in 70% hydrogen fluoride in pyridine (0.47 ml, 18 mmol) was added solid sodium nitrite (0.015 g, 0.22 mmol) at 0-5° C. The cooling bath was removed after 20 minutes and the reaction mixture was stirred for 30 minutes at room temperature. The reaction mixture was partitioned between an ice-water mixture (50 ml) and tert-butyl methyl ether (50 ml). The organic layer was collected. The aqueous layer was extracted with two 50-ml portions of tert-butyl methyl ether. The combined organic layers were washed with one 30-ml portion of 2M aqueous sodium hydroxide solution and one 30-ml portion of brine, dried over anhydrous sodium sulfate and concentrated to dryness to give the crude title compound (0.08 g).

Batch 2: To a solution of trans-4-(6-amino-pyridin-2-yl)-cyclohexanecarboxylic acid ethyl ester (0.25 g, 1.0 mmol) in 70% hydrogen fluoride in pyridine (2.4 ml, 92 mmol) was added solid sodium nitrite (0.076 g, 1.1 mmol) at 0-5° C. The cooling bath was removed after 20 minutes and the reaction mixture was stirred for 30 minutes at room temperature. The reaction mixture was partitioned between an ice-water mixture (100 ml) and tert-butyl methyl ether (100 ml). The organic layer was collected. The aqueous layer was extracted with two 100-ml portions of tert-butyl methyl ether. The combined organic layers were washed with one 30-ml portion of 2M aqueous sodium hydroxide solution, one 30-ml portion of brine, dried over anhydrous sodium sulfate and concentrated to dryness to give the crude title compound (0.145 g). The batches were combined and purified by flash-chromatography with n-heptane/ethyl acetate as eluent to give the title compound (0.16 g, 51%) as colorless oil. MS m/e: 252 ([M+H]$^+$)

4-Heteroaryl-cyclohexanecarboxylic acid ester intermediate 15 cis/trans-4-(5-Fluoro-pyridin-2-yl)-cyclohexanecarboxylic acid ethyl ester

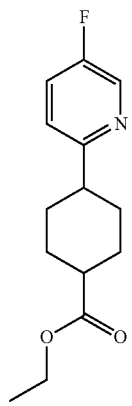

The title compound was obtained as colorless liquid in 97% yield from (RS)-4-(5-fluoro-pyridin-2-yl)-cyclohex-3-enecarboxylic acid ethyl ester according to general procedure (V). MS m/e: 252 ([M+H]$^+$)

4-Heteroaryl-cyclohexanecarboxylic acid ester intermediate 16 trans-4-(5-Fluoro-pyridin-2-yl)-cyclohexanecarboxylic acid ethyl ester

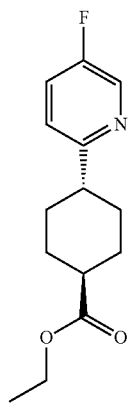 [SMILES: CCOC(=O)[C@H]1CC[C@H](c2ccc(F)cn2)CC1]

The title compound was obtained as yellow liquid in quantitative yield from cis/trans-4-(5-fluoro-pyridin-2-yl)-cyclohexanecarboxylic acid ethyl ester according to general procedure (VI). MS m/e: 252 ([M+H]$^+$)

4-Heteroaryl-cyclohexanecarboxylic acid ester intermediate 17 cis/trans-4-(4-Amino-pyridin-2-yl)-cyclohexanecarboxylic acid ethyl ester (3:1)

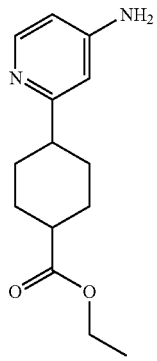 [SMILES: CCOC(=O)C1CCC(c2cc(N)ccn2)CC1]

The title compound was obtained as light yellow oil in 91% yield from (RS)-4-(4-amino-pyridin-2-yl)-cyclohex-3-enecarboxylic acid ethyl ester according to general procedure (V). MS m/e: 249 ([M+H]$^+$)

4-Heteroaryl-cyclohexanecarboxylic acid ester intermediate 18 cis/trans-4-(4-Amino-pyridin-2-yl)-cyclohexanecarboxylic acid ethyl ester (1:9)

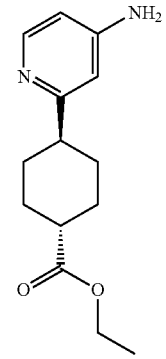 [SMILES: CCOC(=O)[C@H]1CC[C@H](c2cc(N)ccn2)CC1]

The title compound was obtained as yellow oil in 92% yield from cis/trans-4-(4-amino-pyridin-2-yl)-cyclohexanecarboxylic acid ethyl ester (3:1) according to general procedure (VI). MS m/e: 249 ([M+H]$^+$)

4-Heteroaryl-cyclohexanecarboxylic acid ester intermediate 19 cis/trans-4-(4-Chloro-pyridin-2-yl)-cyclohexanecarboxylic acid ethyl ester (1:6)

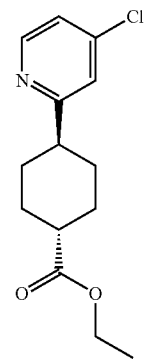 [SMILES: CCOC(=O)[C@H]1CC[C@H](c2cc(Cl)ccn2)CC1]

To a solution of cis/trans-4-(4-amino-pyridin-2-yl)-cyclohexanecarboxylic acid ethyl ester (1:9) (0.638 g, 2.57 mmol) in concentrated hydrochloric acid (11.0 ml, 128 mmol) was added in small portions sodium nitrite (4.43 g, 64.2 mmol) at 0-5° C. The reaction mixture was allowed to warm to room temperature. Copper (I) chloride (10.7 g, 108 mmol) was added in one portion. Stirring for 2 h was followed by quenching with 32% sodium hydroxide solution (9.52 ml, 103 mmol) at 0-5° C. The reaction mixture was partitioned between dichloromethane (50 ml) and water (20 ml). The layers were separated. The aqueous layer was extracted with two 100 ml-portions of dichloromethane. The combined organic layers were washed with one 25 ml-portion of water, dried over anhydrous sodium sulfate and concentrated in vacuo. Flash-chromatography with n-heptane/ethyl acetate as eluent gave the title compound (0.186 g, 27%) as colorless oil.

4-Heteroaryl-cyclohexanecarboxylic acid ester intermediate 20 cis/trans-4-(3-Fluoro-pyridin-2-yl)-cyclohexanecarboxylic acid ethyl ester

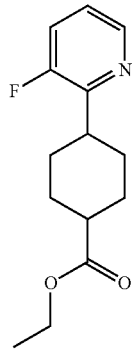

The title compound was obtained as colorless liquid in 97% yield from (RS)-4-(3-fluoro-pyridin-2-yl)-cyclohex-3-enecarboxylic acid ethyl ester according to general procedure (V). MS m/e: 252 ([M+H]$^+$)

4-Heteroaryl-cyclohexanecarboxylic acid ester intermediate 21 trans-4-(3-Fluoro-pyridin-2-yl)-cyclohexanecarboxylic acid ethyl ester

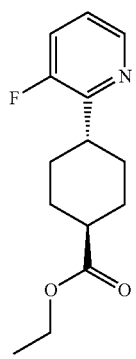

The title compound was obtained as colorless oil in quantitative yield from cis/trans-4-(3-fluoro-pyridin-2-yl)-cyclo-hexanecarboxylic acid ethyl ester according to general procedure (VI). MS m/e: 252 ([M+H]$^+$)

4-Heteroaryl-cyclohexanecarboxylic acid ester intermediate 22 cis/trans-4-Pyridin-3-yl-cyclohexanecarboxylic acid ethyl ester (7:3)

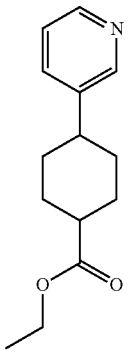

The title compound was obtained as colorless oil in 89% yield from (RS)-4-pyridin-3-yl-cyclohex-3-enecarboxylic acid ethyl ester according to general procedure (V). MS m/e: 234 ([M+H]$^+$)

4-Heteroaryl-cyclohexanecarboxylic acid ester intermediate 23 trans-4-Pyridin-3-yl-cyclohexanecarboxylic acid ethyl ester

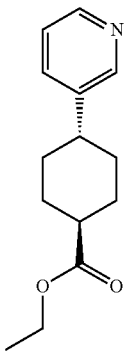

The title compound was obtained as amorphous, light brown solid in quantitative yield from cis/trans-4-pyridin-3- yl-cyclohexanecarboxylic acid ethyl ester according to general procedure (VI). MS m/e: 234 ([M+H]+)

4-Heteroaryl-cyclohexanecarboxylic acid ester intermediate 24 cis/trans-4-(2-Amino-pyridin-3-yl)-cyclohexanecarboxylic acid ethyl ester

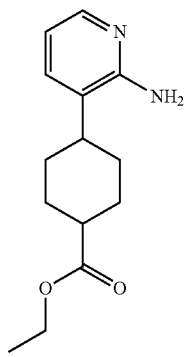

The title compound was obtained as colorless oil in quantitative yield from (RS)-4-(2-amino-pyridin-3-yl)-cyclohex-3-enecarboxylic acid ethyl ester according to general procedure (V). MS m/e: 249 ([M+H]+)

4-Heteroaryl-cyclohexanecarboxylic acid ester intermediate 25 trans-4-(2-Amino-pyridin-3-yl)-cyclohexanecarboxylic acid ethyl ester

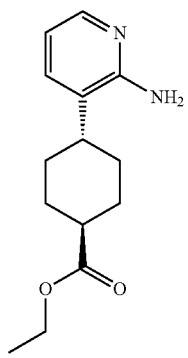

The title compound was obtained as light yellow solid in 82% yield from cis/trans-4-(2-amino-pyridin-3-yl)-cyclohexanecarboxylic acid ethyl ester according to general procedure (VI). MS m/e: 249 ([M+H]+)

4-Heteroaryl-cyclohexanecarboxylic acid ester intermediate 26 trans-4-(2-Chloro-pyridin-3-yl)-cyclohexanecarboxylic acid ethyl ester

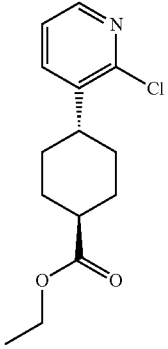 [SMILES: CCOC(=O)[C@H]1CC[C@H](c2cccnc2Cl)CC1]

To a solution of trans-4-(2-amino-pyridin-3-yl)-cyclohexanecarboxylic acid ethyl ester (0.21 g, 0.86 mmol) in concentrated hydrochloric acid (3.7 ml, 43 mmol) was added solid sodium nitrite (1.49 g, 21.5 mmol) at 0-5° C. The cooling bath was removed and copper(I) chloride (3.58 g, 36.2 mmol) was added at room temperature. After stirring for 2 h the mixture was partitioned between water (50 ml) and ethyl acetate (50 ml). The organic layer was collected. The aqueous layer was extracted with two 50-ml portions of ethyl acetate. The combined organic layers were dried over anhydrous sodium sulfate and concentrated to dryness. Flash-chromatography with n-heptane/ethyl acetate as eluent gave the title compound (0.093 g, 44%) as yellow oil. MS m/e: 268 ([M+H]+)

4-Heteroaryl-cyclohexanecarboxylic acid ester intermediate 27 trans-4-(2-Fluoro-pyridin-3-yl)-cyclohexanecarboxylic acid ethyl ester

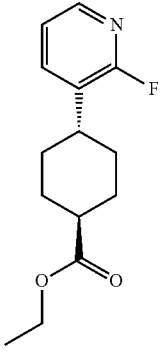 [SMILES: CCOC(=O)[C@H]1CC[C@H](c2cccnc2F)CC1]

To a solution of trans-4-(2-amino-pyridin-3-yl)-cyclohexanecarboxylic acid ethyl ester (0.25 g, 1.0 mmol) in 70% hydrogen fluoride in pyridine (2.4 ml, 92 mmol) was added solid sodium nitrite (0.076 g, 1.1 mmol) at 0-5° C. The cooling bath was removed after 30 minutes and the reaction mixture was stirred for 2 h at room temperature. The reaction mixture was partitioned between an ice-water mixture (50 ml)

and tert-butyl methyl ether (50 ml). The organic layer was collected. The aqueous layer was extracted with one 100-ml portion of tert-butyl methyl ether. The combined organic layers were dried over anhydrous sodium sulfate and concentrated to dryness. Flash-chromatography with n-heptane/ethyl acetate as eluent gives the title compound (0.11 g, 44%) as light yellow oil. MS m/e: 252 ([M+H]$^+$)

4-Heteroaryl-cyclohexanecarboxylic acid ester intermediate 28 cis/trans-4-Pyrimidin-2-yl-cyclohexanecarboxylic acid ethyl ester (7:3)

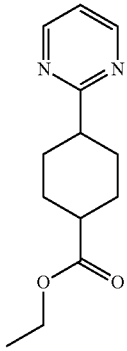

The title compound was obtained as light brown oil in 78% yield from (RS)-4-pyrimidin-2-yl-cyclohex-3-enecarboxylic acid ethyl ester according to general procedure (V). MS m/e: 235 ([M+H]$^+$)

4-Heteroaryl-cyclohexanecarboxylic acid ester intermediate 29 cis/trans-4-(4,6-Dimethyl-pyrimidin-2-yl)-cyclohexanecarboxylic acid ethyl ester (4:1)

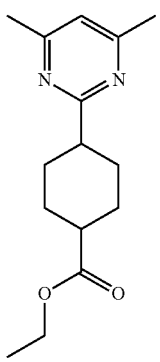 [SMILES: CCOC(=O)C1CCC(c2nc(C)cc(C)n2)CC1]

The title compound was obtained as yellow oil in 97% yield from (RS)-4-(4,6-dimethyl-pyrimidin-2-yl)-cyclohex-3-enecarboxylic acid ethyl ester according to general procedure (V). MS m/e: 263 ([M+H]$^+$)

4-Heteroaryl-cyclohexanecarboxylic acid ester intermediate 30 trans-4-(4,6-Dimethyl-pyrimidin-2-yl)-cyclohexanecarboxylic acid ethyl ester

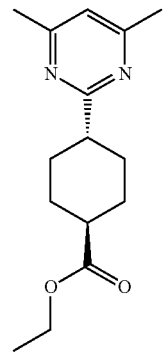 [SMILES: CCOC(=O)[C@H]1CC[C@H](c2nc(C)cc(C)n2)CC1]

The title compound was obtained as yellow oil in 71% yield from cis/trans-4-(4,6-dimethyl-pyrimidin-2-yl)-cyclohexanecarboxylic acid ethyl ester according to general procedure (VI). MS m/e: 263 ([M+H]$^+$)

4-Heteroaryl-cyclohexanecarboxylic acid ester intermediate 31 cis/trans-4-(2-Methyl-pyrimidin-4-yl)-cyclohexanecarboxylic acid ethyl ester (2:1)

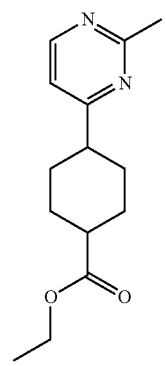 [SMILES: CCOC(=O)C1CCC(c2ccnc(C)n2)CC1]

The title compound was obtained as colorless liquid in 98% yield from (RS)-4-(2-methyl-pyrimidin-4-yl)-cyclohex-3-enecarboxylic acid ethyl ester according to general procedure (V). MS m/e: 249 ([M+H]$^+$)

4-Heteroaryl-cyclohexanecarboxylic acid ester intermediate 32 trans-4-(2-Methyl-pyrimidin-4-yl)-cyclohexanecarboxylic acid ethyl ester

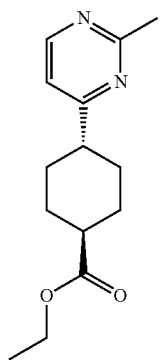 [SMILES: CCOC(=O)[C@H]1CC[C@H](c2ccnc(C)n2)CC1]

The title compound was obtained as brown oil in quantitative yield from cis/trans-4-(2-methyl-pyrimidin-4-yl)-cyclohexanecarboxylic acid ethyl ester according to general procedure (VI). MS m/e: 249 ([M+H]$^+$)

4-Heteroaryl-cyclohexanecarboxylic acid ester intermediate 33 cis/trans-4-Pyrazin-2-yl-cyclohexanecarboxylic acid ethyl ester

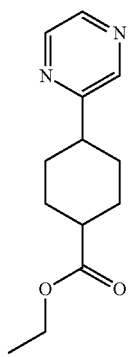

The title compound was obtained as colorless liquid in 72% yield from (RS)-4-(3-chloro-pyrazin-2-yl)-cyclohex-3-en-ecarboxylic acid ethyl ester and triethylamine (1 eq) as additive according to general procedure (V). MS m/e: 235 ([M+H]$^+$)

4-Heteroaryl-cyclohexanecarboxylic acid ester intermediate 34 trans-4-Pyrazin-2-yl-cyclohexanecarboxylic acid ethyl ester

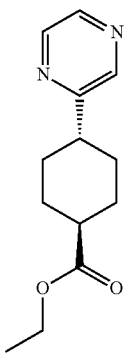

The title compound was obtained as yellow oil in quantitative yield from cis/trans-4-pyrazin-2-yl-cyclohexanecarboxylic acid ethyl ester according to general procedure (VI). MS m/e: 235 ([M+H]$^+$)

4-Heteroaryl-cyclohexanecarboxylic acid ester intermediate 35 cis/trans-4-(6-Methyl-pyrazin-2-yl)-cyclohexanecarboxylic acid ethyl ester

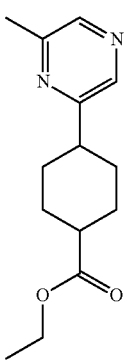

The title compound was obtained as light yellow oil in quantitative yield from (RS)-4-(6-methyl-pyrazin-2-yl)-cyclohex-3-enecarboxylic acid ethyl ester according to general procedure (V). MS m/e: 249 ([M+H]⁺)

4-Heteroaryl-cyclohexanecarboxylic acid ester intermediate 36 trans-4-(6-Methyl-pyrazin-2-yl)-cyclohexanecarboxylic acid ethyl ester

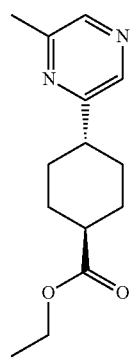 [SMILES: CCOC(=O)[C@H]1CC[C@H](c2cncc(C)n2)CC1]

The title compound was obtained as yellow oil in 66% yield from cis/trans-4-(6-methyl-pyrazin-2-yl)-cyclohexanecarboxylic acid ethyl ester according to general procedure (VI). MS m/e: 249 ([M+H]⁺)

4-Heteroaryl-cyclohexanecarboxylic acid ester intermediate 37 cis/trans-4-(3-Methyl-pyrazin-2-yl)-cyclohexanecarboxylic acid ethyl ester (2:1)

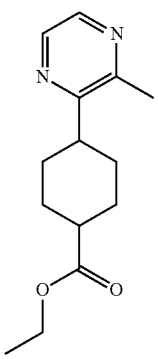

The title compound was obtained as yellow oil in 88% yield from (RS)-4-(3-methyl-pyrazin-2-yl)-cyclohex-3-enecarboxylic acid ethyl ester according to general procedure (V). MS m/e: 249 ([M+H]⁺)

4-Heteroaryl-cyclohexanecarboxylic acid ester intermediate 38 trans-4-(3-Methyl-pyrazin-2-yl)-cyclohexanecarboxylic acid ethyl ester

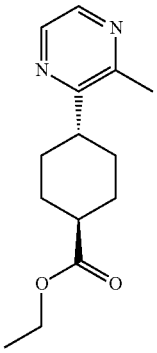 [SMILES: CCOC(=O)[C@H]1CC[C@H](c2nccnc2C)CC1]

The title compound was obtained as yellow oil in 56% yield from cis/trans-4-(3-methyl-pyrazin-2-yl)-cyclohexanecarboxylic acid ethyl ester according to general procedure (VI). MS m/e: 249 ([M+H]⁺)

4-Heteroaryl-cyclohexanecarboxylic acid ester intermediate 39 cis/trans-4-(3,6-Dimethyl-pyrazin-2-yl)-cyclohexanecarboxylic acid ethyl ester (2:1)

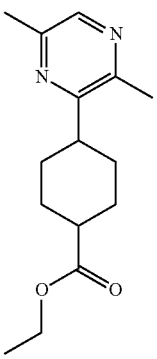

The title compound was obtained as yellow liquid in 90% yield from (RS)-4-(3,6-dimethyl-pyrazin-2-yl)-cyclohex-3-enecarboxylic acid ethyl ester according to general procedure (V). MS m/e: 263 ([M+H]+)

4-Heteroaryl-cyclohexanecarboxylic acid ester intermediate 40 trans-4-(3,6-Dimethyl-pyrazin-2-yl)-cyclohexanecarboxylic acid ethyl ester

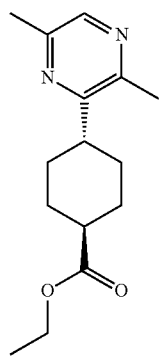

The title compound was obtained as yellow oil in 89% yield from cis/trans-4-(3,6-dimethyl-pyrazin-2-yl)-cyclohexanecarboxylic acid ethyl ester according to general procedure (VI). MS m/e: 263 ([M+H]+)

4-Heteroaryl-cyclohexanecarboxylic acid ester intermediate 41 cis/trans-4-Pyridazin-3-yl-cyclohexanecarboxylic acid ethyl ester

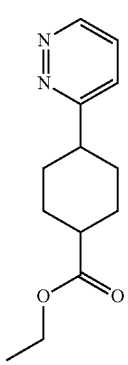

The title compound was obtained as yellow liquid in 90% yield from (RS)-4-(6-chloro-pyridazin-3-yl)-cyclohex-3-en-ecarboxylic acid ethyl ester and triethylamine (1 eq) as additive according to general procedure (V). MS m/e: 235 ([M+H]+)

4-Heteroaryl-cyclohexanecarboxylic acid ester intermediate 42 cis/trans-4-(3-Amino-pyridin-2-yl)-cyclohexanecarboxylic acid ethyl ester (3:1)

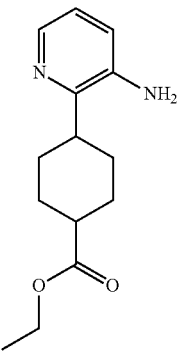 [SMILES: CCOC(=O)C1CCC(c2ncccc2N)CC1]

The title compound was obtained as light yellow viscous oil in quantitative yield from (RS)-4-(3-amino-pyridin-2-yl)-cyclohex-3-enecarboxylic acid ethyl ester according to general procedure (V). MS m/e: 249 ([M+H]+)

4-Heteroaryl-cyclohexanecarboxylic acid ester intermediate 43 cis/trans-4-(3-Amino-pyridin-2-yl)-cyclohexanecarboxylic acid ethyl ester (1:11)

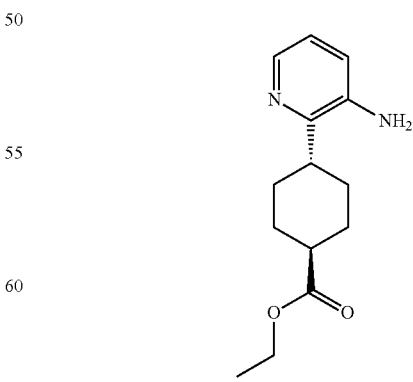

The title compound was obtained as off-white solid in 46% yield from cis/trans-4-(3-amino-pyridin-2-yl)-cyclohexanecarboxylic acid ethyl ester (3:1) according to general procedure (VI). MS m/e: 249 ([M+H]+)

4-Heteroaryl-cyclohexanecarboxylic acid ester intermediate 44 cis/trans-4-(3,5-Difluoro-pyridin-2-yl)-cyclohexanecarboxylic acid ethyl ester (2:1)

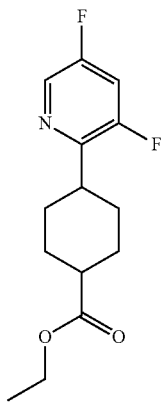 [SMILES: CCOC(=O)C1CCC(c2ncc(F)cc2F)CC1]

The title compound was obtained as light yellow oil in 99% yield from (RS)-4-(3,5-difluoro-pyridin-2-yl)-cyclohex-3-enecarboxylic acid ethyl ester according to general procedure (V). MS m/e: 270 ([M+H]+)

4-Heteroaryl-cyclohexanecarboxylic acid ester intermediate 45 trans-4-(3,5-Difluoro-pyridin-2-yl)-cyclohexanecarboxylic acid ethyl ester (1:9)

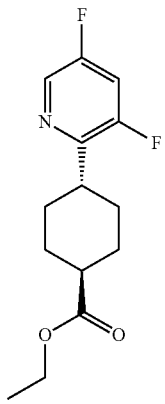 [SMILES: CCOC(=O)[C@H]1CC[C@H](c2ncc(F)cc2F)CC1]

The title compound was obtained as light yellow oil in 25% yield from cis/trans-4-(3,5-difluoro-pyridin-2-yl)-cyclohexanecarboxylic acid ethyl ester (2:1) according to general procedure (VI). MS m/e: 270 ([M+H]+)

4-Heteroaryl-cyclohexanecarboxylic acid intermediates of formula (IX)

General Procedure (VII)

Saponification

A solution of a 4-heteroaryl-cyclohexanecarboxylic acid ester of formula VII in 1,4-dioxane (0.1 M) and 2M aqueous sodium hydroxide solution (10 eq) is stirred at room temperature for 20 h. The reaction mixture is partitioned between an organic solvent such as ethyl acetate or tert-butyl methyl ether and water. The organic layer is extracted with one or two portions of 0.5 M aqueous sodium hydroxide solution. The aqueous layer is acidified by addition of 2M aqueous hydrogen chloride solution and extracted with two or three portions of organic solvent. The combined organic extracts are dried over anhydrous sodium sulfate and concentrated to dryness to give a 4-heteroaryl-cyclohexanecarboxylic acid of formula IX, which can usually be used in the next step without further purification.

4-Heteroaryl-cyclohexanecarboxylic acid 1 trans-4-(6-Chloro-pyridin-2-yl)-cyclohexanecarboxylic acid

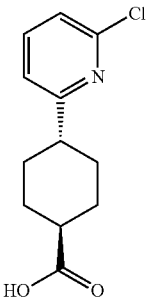 [SMILES: O=C(O)[C@H]1CC[C@H](c2cccc(Cl)n2)CC1]

The title compound was obtained as white solid in 98% yield from trans-4-(6-chloro-pyridin-2-yl)-cyclohexanecarboxylic acid ethyl ester according to general procedure (VII). MS m/e: 238 ([M−H]−)

4-Heteroaryl-cyclohexanecarboxylic acid 2 trans-4-(6-Fluoro-pyridin-2-yl)-cyclohexanecarboxylic acid

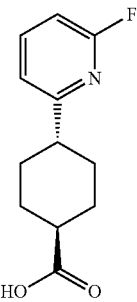

The title compound was obtained as white solid in quantitative yield from trans-4-(6-fluoro-pyridin-2-yl)-cyclohexanecarboxylic acid ethyl ester according to general procedure (VII). MS m/e: 222 ([M–H]⁻)

4-Heteroaryl-cyclohexanecarboxylic acid 3 cis/trans-4-(4-Chloro-pyridin-2-yl)-cyclohexanecarboxylic acid

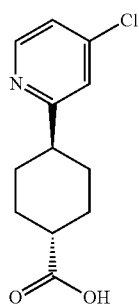 [SMILES: O=C(O)[C@H]1CC[C@H](c2cc(Cl)ccn2)CC1]

The title compound was obtained as white solid in 78% yield from cis/trans-4-(4-chloro-pyridin-2-yl)-cyclohexanecarboxylic acid ethyl ester (1:6) according to general procedure (VII). MS m/e: 238 ([M–H]⁻)

4-Heteroaryl-cyclohexanecarboxylic acid 4 trans-4-(2-Chloro-pyridin-3-yl)-cyclohexanecarboxylic acid

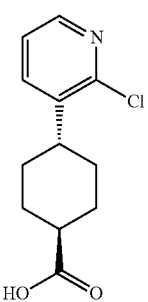 [SMILES: O=C(O)[C@H]1CC[C@H](c2cccnc2Cl)CC1]

The title compound was obtained as white solid in 97% yield from trans-4-(2-chloro-pyridin-3-yl)-cyclohexanecarboxylic acid ethyl ester according to general procedure (VII). MS m/e: 238 ([M–H]⁻)

4-Heteroaryl-cyclohexanecarboxylic acid 5 trans-4-(2-Fluoro-pyridin-3-yl)-cyclohexanecarboxylic acid

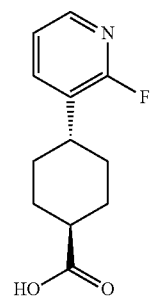 [SMILES: O=C(O)[C@H]1CC[C@H](c2cccnc2F)CC1]

The title compound was obtained as off-white solid in 97% yield from trans-4-(2-fluoro-pyridin-3-yl)-cyclohexanecarboxylic acid ethyl ester according to general procedure (VII). MS m/e: 222 ([M–H]⁻)

4-Heteroaryl-cyclohexanecarboxylic acid 6 cis/trans-4-Pyrimidin-2-yl-cyclohexanecarboxylic acid (2:1)

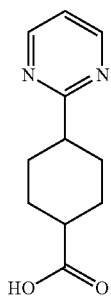

The title compound was obtained as off-white solid in 70% yield from cis/trans-4-pyrimidin-2-yl-cyclohexanecarboxylic acid ethyl ester according to general procedure (VII). MS m/e: 205 ([M−H]$^-$)

4-Heteroaryl-cyclohexanecarboxylic acid 7 cis/trans-4-Pyridazin-3-yl-cyclohexanecarboxylic acid (3:2)

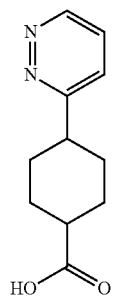

The title compound was obtained as brown solid in quantitative yield from cis/trans-4-pyridazin-3-yl-cyclohexanecarboxylic acid ethyl ester according to general procedure (VII). MS m/e: 205 ([M−H]$^-$)

4-Heteroaryl-cyclohexanecarboxylic acid 8 trans-4-(3-Chloro-pyridin-2-yl)-cyclohexanecarboxylic acid

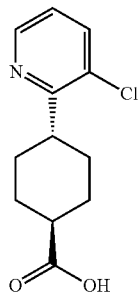 [SMILES: O=C(O)[C@H]1CC[C@H](c2ncccc2Cl)CC1]

To a solution of cis/trans-4-(3-amino-pyridin-2-yl)-cyclohexanecarboxylic acid ethyl ester (1:11) (0.570 g, 2.30 mmol) in concentrated hydrochloric acid (37%; 20 ml) was added sodium nitrite (0.292 g, 4.23 mmol) in small portions at 0-5° C. Stirring for 20 minutes was followed by addition of copper (I) chloride (0.493 g, 4.83 mmol) in one portion. After 10 minutes the reaction mixture was heated to 65° C. (oil bath temperature). The temperature was maintained at 65° C. for 20 h. The reaction mixture was cooled to 0-5° C. and adjusted to pH 4 by addition of aqueous sodium hydroxide solution (32%; 20 ml). The green aqueous layer was extracted with three 75 ml-portions of ethyl acetate. The combined organic layers were dried over anhydrous sodium sulfate and concentrated in vacuo. The residue was purified by flash chromatography over SiO$_2$ with n-heptane/ethyl acetate as eluent to give the title compound (0.424 g, 77%) as off-white solid. MS m/e: 240 ([M+H]$^+$)

4-Heteroaryl-cyclohexanecarboxylic acid 9 trans-4-(3,5-Difluoro-pyridin-2-yl)-cyclohexanecarboxylic acid

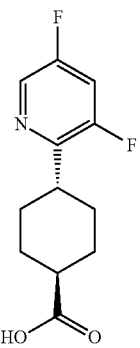 [SMILES: O=C(O)[C@H]1CC[C@H](c2ncc(F)cc2F)CC1]

The title compound was obtained as off-white solid in quantitative yield from cis/trans-4-(3,5-difluoro-pyridin-2-yl)-cyclohexanecarboxylic acid ethyl ester (1:9) according to general procedure (VII). MS m/e: 240 ([M−H]$^-$)

Hydrazide Intermediates of Formula (II)

General Procedure (VIII)

Hydrazide Formation from Acid

To a solution of a 4-heteroaryl-cyclohexanecarboxylic acid intermediate of formula (IX) (1 eq) and triethylamine (1.05 eq) in tetrahydrofuran (0.2 M) is added ethyl chloroformate (1.05 eq) at 0° C. The reaction mixture is stirred at 0° C. for 1 h. The ammonium salts are removed by filtration. The filtrate is added to a cold solution of hydrazine hydrate (2 eq) in methanol (0.2 M). The reaction mixture is stirred at room temperature for 2-16 h. The solvent is evaporated under reduced pressure, and the residue is partitioned between an organic solvent such as ethyl acetate or dichloromethane and water. The organic layer is separated. The aqueous layer is extracted with two or three portions of organic solvent. The combined organic layers are dried over anhydrous sodium sulfate and concentrated in vacuo to give a hydrazide intermediate of formula (II), which is usually used in the next step without further purification.

General Procedure (IX)

Hydrazide Formation from Ester

A mixture of a 4-heteroaryl-cyclohexanecarboxylic acid ester intermediate of formula (VIII) (1 eq) and hydrazine hydrate (2-6 eq) in n-butanol (0.2-1 M) is heated at reflux for 16-72 h. After cooling to room temperature the reaction mixture is partitioned between an organic solvent such as ethyl acetate or dichloromethane and water. The layers are separated and the aqueous layer is extracted with two portions of organic solvent. The combined organic layers are dried over anhydrous sodium sulfate and concentrated in vacuo to give a hydrazide intermediate of formula (II), which is usually used in the next step without further purification.

Hydrazide 1 trans-4-Pyridin-2-yl-cyclohexanecarboxylic acid hydrazide

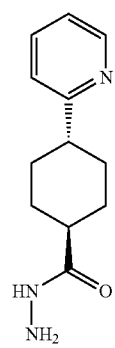

The title compound was obtained as white solid in 84% yield from trans-4-pyridin-2-yl-cyclohexanecarboxylic acid ethyl ester according to general procedure (IX). MS m/e: 220 ([M+H]$^+$)

Hydrazide 2 trans-4-(6-Methyl-pyridin-2-yl)-cyclohexanecarboxylic acid hydrazide

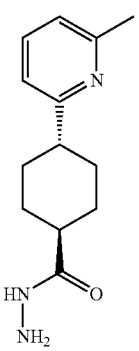

The title compound was obtained as white solid in 44% yield from trans-4-(6-methyl-pyridin-2-yl)-cyclohexanecarboxylic acid ethyl ester according to general procedure (IX). MS m/e: 234 ([M+H]$^+$)

Hydrazide 3 trans-4-(6-Ethyl-pyridin-2-yl)-cyclohexanecarboxylic acid hydrazide

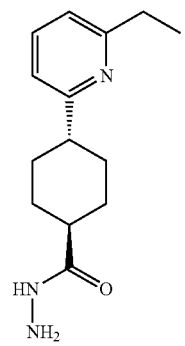

The title compound was obtained as white solid in 66% yield from trans-4-(6-ethyl-pyridin-2-yl)-cyclohexanecarboxylic acid ethyl ester according to general procedure (IX). MS m/e: 248 ([M+H]$^+$)

Hydrazide 4 trans-4-(6-isopropyl-pyridin-2-yl)-cyclohexanecarboxylic acid hydrazide

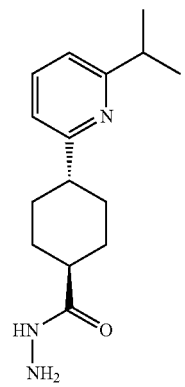 [SMILES: CC(C)c1cccc([C@H]2CC[C@H](C(=O)NN)CC2)n1]

The title compound was obtained as yellow solid in 98% yield from trans-4-(6-isopropyl-pyridin-2-yl)-cyclohexanecarboxylic acid ethyl ester according to general procedure (IX). MS m/e: 262 ([M+H]$^+$)

Hydrazide 5 trans-4-(6-Methoxy-pyridin-2-yl)-cyclohexanecarboxylic acid hydrazide

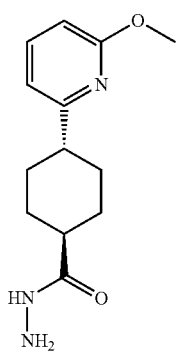

The title compound was obtained as white solid in 81% yield from trans-4-(6-methoxy-pyridin-2-yl)-cyclohexanecarboxylic acid ethyl ester according to general procedure (IX). MS m/e: 250 ([M+H]$^+$)

Hydrazide 6 trans-4-(6-Chloro-pyridin-2-yl)-cyclohexanecarboxylic acid hydrazide

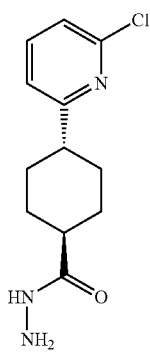 [SMILES: NNC(=O)[C@H]1CC[C@H](c2cccc(Cl)n2)CC1]

The title compound was obtained as white solid in 84% yield from trans-4-(6-chloro-pyridin-2-yl)-cyclohexanecarboxylic acid according to general procedure (VIII). MS m/e: 254 ([M+H]$^+$)

Hydrazide 7 trans-4-(6-Fluoro-pyridin-2-yl)-cyclohexanecarboxylic acid hydrazide

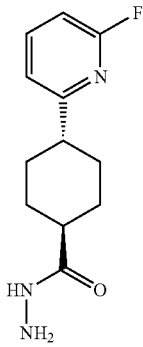 [SMILES: NNC(=O)[C@H]1CC[C@H](c2cccc(F)n2)CC1]

The title compound was obtained as off-white solid in 92% yield from trans-4-(6-fluoro-pyridin-2-yl)-cyclohexanecarboxylic acid according to general procedure (VIII). MS m/e: 238 ([M+H]$^+$)

Hydrazide 8 trans-4-(5-Fluoro-pyridin-2-yl)-cyclohexanecarboxylic acid hydrazide

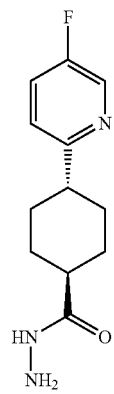

The title compound was obtained as white solid in 69% yield from trans-4-(5-fluoro-pyridin-2-yl)-cyclohexanecarboxylic acid ethyl ester according to general procedure (IX). MS m/e: 238 ([M+H]$^+$)

Hydrazide 9 cis/trans-4-(4-Chloro-pyridin-2-yl)-cyclohexanecarboxylic acid hydrazide

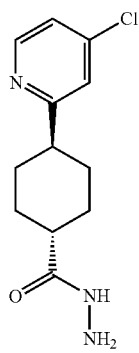 [SMILES: NNC(=O)[C@H]1CC[C@H](c2cc(Cl)ccn2)CC1]

The title compound was obtained as white solid in 74% yield from cis/trans-4-(4-chloro-pyridin-2-yl)-cyclohexanecarboxylic acid according to general procedure (VIII). MS m/e: 254 ([M+H]$^+$)

Hydrazide 10 trans-4-(3-Fluoro-pyridin-2-yl)-cyclohexanecarboxylic acid hydrazide

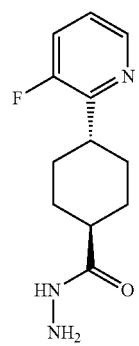

The title compound was obtained as white solid in quantitative yield from trans-4-(3-fluoro-pyridin-2-yl)-cyclohexanecarboxylic acid ethyl ester according to general procedure (IX). MS m/e: 238 ([M+H]$^+$)

Hydrazide 11 cis/trans-4-(3-Fluoro-pyridin-2-yl)-cyclohexanecarboxylic acid hydrazide (7.8:1)

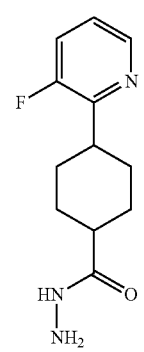

The title compound was obtained as white solid in 91% yield from cis/trans-4-(3-fluoro-pyridin-2-yl)-cyclohexanecarboxylic acid ethyl ester according to general procedure (IX). MS m/e: 238 ([M+H]$^+$)

Hydrazide 12 trans-4-Pyridin-3-yl-cyclohexanecarboxylic acid hydrazide

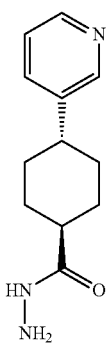

The title compound was obtained as light yellow solid in 53% yield from trans-4-pyridin-3-yl-cyclohexanecarboxylic acid ethyl ester according to general procedure (IX). MS m/e: 220 ([M+H]$^+$)

Hydrazide 13 trans-4-(2-Chloro-pyridin-3-yl)-cyclohexanecarboxylic acid hydrazide

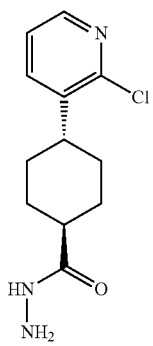 [SMILES: NNC(=O)[C@H]1CC[C@H](c2cccnc2Cl)CC1]

The title compound was obtained as white solid in 97% yield from trans-4-(2-chloro-pyridin-3-yl)-cyclohexanecarboxylic acid according to general procedure (VIII). MS m/e: 254 ([M+H]$^+$)

Hydrazide 14 trans-4-(2-Fluoro-pyridin-3-yl)-cyclohexanecarboxylic acid hydrazide

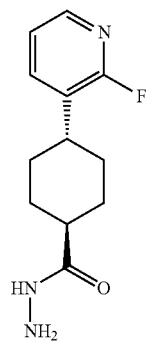

The title compound was obtained as white solid in 82% yield from trans-4-(2-fluoro-pyridin-2-yl)-cyclohexanecarboxylic acid according to general procedure (VIII). MS m/e: 238 ([M+H]$^+$)

Hydrazide 15 cis/trans-4-Pyrimidin-2-yl-cyclohexanecarboxylic acid hydrazide

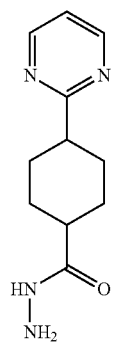

The title compound was obtained as white solid in 81% yield from cis/trans-4-pyrimidin-2-yl-cyclohexanecarboxylic acid according to general procedure (VIII). MS m/e: 221 ([M+H]$^+$)

Hydrazide 16 trans-4-(4,6-Dimethyl-pyrimidin-2-yl)-cyclohexanecarboxylic acid hydrazide

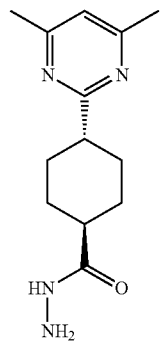

The title compound was obtained as white solid in 87% yield from trans-4-(4,6-dimethyl-pyrimidin-2-yl)-cyclohexanecarboxylic acid ethyl ester according to general procedure (IX). MS m/e: 249 ([M+H]$^+$)

Hydrazide 17 trans-4-(2-Methyl-pyrimidin-4-yl)-cyclohexanecarboxylic acid hydrazide

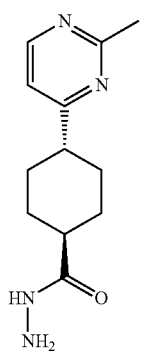

The title compound was obtained as off-white solid in 58% yield from trans-4-(2-methyl-pyrimidin-4-yl)-cyclohexanecarboxylic acid ethyl ester according to general procedure (IX). MS m/e: 235 ([M+H]$^+$)

Hydrazide 18 trans-4-(Pyrazin-2-yl)-cyclohexanecarboxylic acid hydrazide

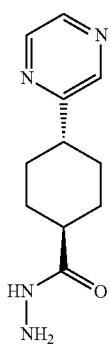

The title compound was obtained as yellow solid in quantitative yield from trans-4-(pyrazin-2-yl)-cyclohexanecarboxylic acid ethyl ester according to general procedure (IX).

Hydrazide 19 trans-4-(6-Methyl-pyrazin-2-yl)-cyclohexanecarboxylic acid hydrazide

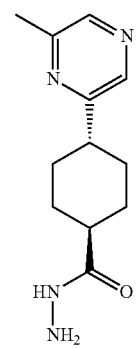

The title compound was obtained as white solid in 82% yield from trans-4-(6-methyl-pyrazin-2-yl)-cyclohexanecarboxylic acid ethyl ester according to general procedure (IX). MS m/e: 235 ([M+H]$^+$)

Hydrazide 20 trans-4-(3-Methyl-pyrazin-2-yl)-cyclohexanecarboxylic acid hydrazide

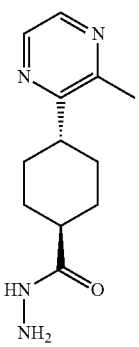 [SMILES: Cc1nccnc1[C@H]1CC[C@H](C(=O)NN)CC1]

The title compound was obtained as white solid in 73% yield from trans-4-(3-methyl-pyrazin-2-yl)-cyclohexanecarboxylic acid ethyl ester according to general procedure (IX). MS m/e: 235 ([M+H]$^+$)

Hydrazide 21 trans-4-(3,6-Dimethyl-pyrazin-2-yl)-cyclohexanecarboxylic acid hydrazide

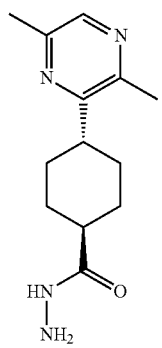

The title compound was obtained as white solid in 90% yield from trans-4-(3,6-dimethyl-pyrazin-2-yl)-cyclohexanecarboxylic acid ethyl ester according to general procedure (IX). MS m/e: 249 ([M+H]$^+$)

Hydrazide 22 cis/trans-4-Pyridazin-3-yl-cyclohexanecarboxylic acid hydrazide

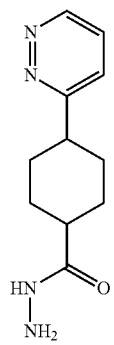

The title compound was obtained as white solid in quantitative yield from cis/trans-4-pyridazin-3-yl-cyclohexanecarboxylic acid according to general procedure (VIII). MS m/e: 221 ([M+H]$^+$)

Hydrazide 23 trans-4-(3-Chloro-pyridin-2-yl)-cyclohexanecarboxylic acid hydrazide

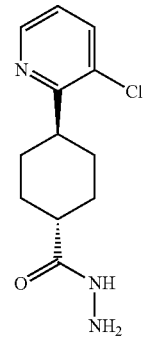 [SMILES: NNC(=O)[C@H]1CC[C@H](c2ncccc2Cl)CC1]

The title compound was obtained as white solid in 97% yield from trans-4-(3-chloro-pyridin-2-yl)-cyclohexanecarboxylic acid according to general procedure (VIII). MS m/e: 254 ([M+H]$^+$)

Hydrazide 24 trans-4-(3,5-Difluoro-pyridin-2-yl)-cyclohexanecarboxylic acid hydrazide

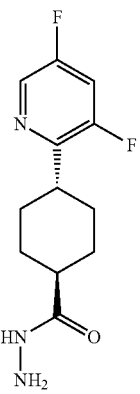

The title compound was obtained as white solid in 67% yield from trans-4-(3,5-difluoro-pyridin-2-yl)-cyclohexanecarboxylic acid according to general procedure (VIII). MS m/e: 256 ([M+H]$^+$)

Thiolactam intermediates of formula III

7-Chloro-2-thioxo-1,2,3,5-tetrahydro-benzo[e][1,4]diazepine-4-carboxylic acid tert-butyl ester a) 4-Chloro-2-chloromethyl-1-nitro-benzene To a solution of 5-chloro-2-nitrobenzyl alcohol (80 g, 0.42 mol) and triethylamine (64 ml, 0.46 mol) in dichloromethane (840 ml) was added drop wise thionyl chloride (34 ml, 0.46 mol) during a period of 30 minutes while the internal temperature was kept below 32° C. by cooling with a water bath. The reaction mixture was stirred for 3 h. The solvent was evaporated and the residue was triturated in warm tert-butyl methyl ether (970 ml). The ammonium salts were removed by filtration and the filtrate was concentrated in vacuo to give the title compound (85 g, 99%) as brown oil which was used in the next step without purification. MS m/e: 205 (M+).

b) (5-Chloro-2-nitro-benzylamino)-acetic acid ethyl ester

A mixture of 4-chloro-2-chloromethyl-1-nitro-benzene (85 g, 0.41 mol), glycine ethyl ester hydrochloride (70 g, 0.50 mol) and triethylamine (121.4 ml, 0.8665 mol) in ethanol (1000 ml) was heated at reflux for 8 h. The solvent was evaporated and the residue was triturated in warm tert-butyl methyl ether. The ammonium salts were removed by filtration and the filtrate was concentrated in vacuo to give the title compound (111 g, 99%) as an amorphous brown solid which was used in the next step without purification. MS m/e: 273 (M+H+).

c) [tert-Butoxycarbonyl-(5-chloro-2-nitro-benzyl)-amino]-acetic acid ethyl ester A solution of (5-chloro-2-nitro-benzylamino)-acetic acid ethyl ester (110 g, 0.403 mol), di-tert-butyl dicarbonate (180 g, 0.807 mol) and 4-N,N-dimethylaminopyridine (2.51 g, 0.0202 mol) in dichloromethane (1200 ml) was stirred for 2 h at 0° C. and further 16 h at room temperature. The solvent was evaporated and the crude product was purified by flash chromatography with a cyclohexane/ethyl acetate mixture as eluent to give the title compound (76.4 g, 51%) as light yellow viscous oil. MS m/e: 373 (M+H+).

d) [(2-Amino-5-chloro-benzyl)-tert-butoxycarbonyl-amino]-acetic acid ethyl ester To a solution of [tert-butoxycarbonyl-(5-chloro-2-nitro-benzyl)-amino]-acetic acid ethyl ester (69.0 g, 0.186 mol) in ethyl acetate (1200 ml) was added zinc bromide (8.5 g, 0.037 mol). The reaction mixture was purged with argon after 15 minutes. After addition of the palladium catalyst (10% on activated charcoal, 7.9 g, 0.0074 mol) the mixture was hydrogenated at ambient pressure during a period of ca. 48 h until ca. 13 l of hydrogen gas had been consumed. The catalyst was removed by filtration and the filtrate was washed with two portions of saturated aqueous sodium bicarbonate solution and brine, each. The organic layer was dried over anhydrous sodium sulfate and concentrated in vacuo to give the title compound (60.6 g, 95.5%) as yellow waxy solid. MS m/e: 343 (M+H+).

e) 7-Chloro-2-oxo-1,2,3,5-tetrahydro-benzo[1,4]diazepine-4-carboxylic acid tert-butyl ester To a solution of [(2-amino-5-chloro-benzyl)-tert-butoxycarbonyl-amino]-acetic acid ethyl ester (60 g, 0.18 mol) in tetrahydrofuran (600 ml) was added potassium tert-butoxide (22 g, 0.19 mol) in small portions at 5° C. under cooling on an ice-water batch. After completed addition the cooling bath was removed and reaction mixture was stirred for 3 h at room temperature followed by addition of water (400 ml), saturated aqueous ammonium chloride solution (280 ml) and ethyl acetate (800 ml). After 10 minutes the precipitate was collected by filtration. The layers were separated from the filtrate, dried over anhydrous sodium sulfate and concentrated in vacuo. The residue was combined with the precipitate, which had previously been collected by filtration, and crystallized from hot ethyl acetate to give the title compound (46 g, 88%) as white solid. MS m/e: 295 (M−H+).

f) 7-Chloro-2-thioxo-1,2,3,5-tetrahydro-benzo[e][1,4]diazepine-4-carboxylic acid tert-butyl ester A mixture of 7-chloro-2-oxo-1,2,3,5-tetrahydro-benzo[1,4]diazepine-4-carboxylic acid tert-butyl ester (41.1 g, 0.139 mol) and 2,4-bis-(4-methoxyphenyl)-1,3,2,4-dithiadiphosphetane-2,4-disulfide (31.5 g, 0.0763 mol) in tetrahydrofuran (1100 ml) was heated at reflux for 3 h. The solvent was evaporated and the residue was triturated in tert-butyl methyl ether. The precipitate was removed by filtration and the filtrate was concentrated to dryness. The residue was crystallized from hot ethanol to give the title compound (37.5 g, 86.4%) as light yellow solid. MS m/e: 311 (M−H+).

7-Fluoro-2-thioxo-1,2,3,5-tetrahydro-benzo[e][1,4]diazepine-4-carboxylic acid tert-butyl ester The title compound was obtained as light yellow solid in comparable yields according to the procedures described above for the synthesis of 7-chloro-2-thioxo-1,2,3,5-tetrahydro-benzo[e][1,4]diazepine-4-carboxylic acid tert-butyl ester using 5-fluoro-2-nitrobenzyl alcohol instead of 5-chloro-2-nitrobenzyl alcohol in step a). MS m/e: 297 (M−H+).

General Procedure (X)

Condensation of Hydrazide and Thiolactam to Triazole

A mixture of a hydrazide of formula II (1-1.5 eq) and a thiolactam of formula III (1 eq) in n-butanol (0.1-0.2 M) is heated at reflux for 16-72 h. After cooling to room temperature the solvent is evaporated and the residue is purified by flash-chromatography to give a compound of formula I. When a thiolactam of formula III-1 (compounds of formula III in which $R^1$ is tert-butoxycarbonyl) is used the N-tert-butoxycarbonyl group of the resulting triazole product of formula I-1 can be partially or completely cleaved thermally, and a secondary amine of formula I-2 is obtained in addition or as the sole product.

General procedure (XI-a)

Cleavage of N-tert-butoxycarbonyl (N—BOC) group

A solution of an N—BOC derivative of formula I-1 (1 eq) in 1.25 M methanolic or 1.5 M ethanolic hydrogen chloride solution (10-20 eq HCl) is heated at 50° C. for 15-60 minutes. After cooling to room temperature the reaction mixture is concentrated in vacuo to give a secondary amine of formula I-2 as hydrochloride salt. Optionally the free base can be obtained by partitioning the hydrochloride salt between 1 M aqueous sodium hydroxide solution and an organic solvent, e.g. ethyl acetate or dichloromethane. The layers are separated and the aqueous layer is extracted with two portions of the organic solvent. The combined organic layers are dried over anhydrous sodium sulfate, filtered and concentrated in vacuo to give the free base of a compound of formula I-2.

General Procedure (XI-b)

Cleavage of N-tert-butoxycarbonyl (N—BOC) Group

A solution of an N—BOC derivative of general formula I-1 (1 eq) and trifluoroacetic acid (10-20 eq) in dichloromethane is stirred at room temperature for 6-24 h. The reaction mixture is partitioned between 1 M aqueous sodium hydroxide solution and an organic solvent such as ethyl acetate or dichloromethane. The layers are separated and the aqueous layer is extracted with two portions of the organic solvent. The combined organic layers are dried over anhydrous sodium sulfate, filtered and concentrated in vacuo to give the free base of a compound of formula I-2.

General Procedure (XII)

Reductive N-alkylation

A mixture of a compound of formula I-2 as free base or as hydrochloride salt (1 eq, 0.1-0.2 M), triethylamine (1 eq when the hydrochloride salt of a compound of formula I-2 is used) and an aldehyde or ketone (8 eq) in methanol is heated at reflux for 2-6 h. After cooling to 0° C. sodium cyanoborohydride (2-3 eq) is added. The reaction mixture is stirred for 3-16 h at room temperature and quenched with 1 M aqueous sodium hydroxide solution. The aqueous layer is extracted with ethyl acetate. The combined organic layers are dried over anhydrous sodium sulfate and concentrated in vacuo. Flash chromatography gives an N-alkyl compound of formula I.

General Procedure (XIII)

Reductive N-methylation

A mixture of a compound of formula I-2 as free base (1 eq, 0.1-0.2 eq), sodium acetate (1.1 eq), acetic acid (1.1 eq) and an aqueous formaldehyde solution (36%, 1.4 eq) in dichloromethane is stirred for 0.5-2 h. After cooling to 0° C. sodium triacetoxyborohydride (1.6 eq) is added. The reaction mixture is stirred for 2-16 h at room temperature and quenched with 1 M aqueous sodium hydroxide solution. The aqueous layer is extracted with ethyl acetate. The combined organic layers are dried over anhydrous sodium sulfate and concentrated in vacuo. Flash chromatography gives an N-methyl compound of formula I-3.

Example 1 trans-8-Chloro-1-(4-pyridin-2-yl-cyclohexyl)-4H,6H-2,3,5,10b-tetraaza-benzo[e]azulene-5-carboxylic acid tert-butyl ester The title compound was obtained as white solid in 72% yield according to general procedure (X). Hydrazide: trans-4-Pyridin-2-yl-cyclohexanecarboxylic acid hydrazide Thiolactam: 7-Chloro-2-thioxo-1,2,3,5-tetrahydro-benzo[e][1,4]diazepine-4-carboxylic acid tert-butyl ester. MS m/e: 480 ([M+H]$^+$)

Example 2 trans-8-Chloro-1-(4-pyridin-2-yl-cyclohexyl)-5,6-dihydro-4H-2,3,5,10b-tetraaza-benzo[e]azulene dihydrochloride The title compound was obtained as white solid in quantitative yield from trans-8-chloro-1-(4-pyridin-2-yl-cyclohexyl)-4H,6H-2,3,5,10b-tetraaza-benzo[e]azulene-5-carboxylic acid tert-butyl ester according to general procedure (XI-a). MS m/e: 380 ([M+H]$^+$)

Example 3 trans-8-Chloro-5-methyl-1-(4-pyridin-2-yl-cyclohexyl)-5,6-dihydro-4H-2,3,5,10b-tetraaza-benzo[e]azulene The title compound was obtained as white solid in 46% yield from trans-8-chloro-1-(4-pyridin-2-yl-cyclohexyl)-5,6-dihydro-4H-2,3,5,10b-tetraaza-benzo[e]azulene dihydrochloride and paraformaldehyde according to general procedure (XII). MS m/e: 394 ([M+H]$^+$)

Example 4 trans-8-Chloro-1-[4-(6-methyl-pyridin-2-yl)-cyclohexyl]-4H,6H-2,3,5,10b-tetraaza-benzo[e]azulene-5-carboxylic acid tert-butyl ester The title compound was obtained as off-white solid in 77% yield according to general procedure (X). Hydrazide: trans-4-(6-Methyl-pyridin-2-yl)-cyclohexanecarboxylic acid hydrazide. Thiolactam: 7-Chloro-2-thioxo-1,2,3,5-tetrahydro-benzo[e][1,4]diazepine-4-carboxylic acid tert-butyl ester. MS m/e: 494 ([M+H]$^+$)

Example 5 trans-8-Chloro-1-[4-(6-methyl-pyridin-2-yl)-cyclohexyl]-5,6-dihydro-4H-2,3,5,10b-tetraaza-benzo[e]azulene The title compound was obtained as white solid in quantitative yield from trans-8-chloro-1-[4-(6-methyl-pyridin-2-yl)-cyclohexyl]-4H,6H-2,3,5,10b-tetraaza-benzo[e]azulene-5-carboxylic acid tert-butyl ester according to general procedure (XI-a). MS m/e: 394 ([M+H]$^+$)

Example 6 trans-8-Chloro-1-[4-(6-methyl-pyridin-2-yl)-cyclohexyl]-5-methyl-5,6-dihydro-4H-2,3,5,10b-tetraaza-benzo[e]azulene The title compound was obtained as white solid in 59% yield from trans-8-chloro-1-[4-(6-methyl-pyridin-2-yl)-cyclohexyl]-5,6-dihydro-4H-2,3,5,10b-tetraaza-benzo[e]azulene and paraformaldehyde according to general procedure (XII). MS m/e: 408 ([M+H]$^+$)

Example 7 trans-8-Chloro-1-[4-(6-ethyl-pyridin-2-yl)-cyclohexyl]-4H,6H-2,3,5,10b-tetraaza-benzo[e]azulene-5-carboxylic acid tert-butyl ester The title compound was obtained as white solid in 48% yield according to general procedure (X). Hydrazide: trans-4-(6-Ethyl-pyridin-2-yl)-cyclohexanecarboxylic acid hydrazide Thiolactam: 7-Chloro-2-thioxo-1,2,3,5-tetrahydro-benzo[e][1,4]diazepine-4-carboxylic acid tert-butyl ester. MS m/e: 508 ([M+H]$^+$)

Example 8 trans-8-Chloro-1-[4-(6-ethyl-pyridin-2-yl)-cyclohexyl]-5,6-dihydro-4H-2,3,5,10b-tetraaza-benzo[e]azulene The title compound was obtained as off-white solid in 83% yield from trans-8-chloro-1-[4-(6-ethyl-pyridin-2-yl)-cyclohexyl]-4H,6H-2,3,5,10b-tetraaza-benzo[e]azulene-5-carboxylic acid tert-butyl ester according to general procedure (XI-a). MS m/e: 408 ([M+H]$^+$)

Example 9 trans-8-Chloro-1-[4-(6-ethyl-pyridin-2-yl)-cyclohexyl]-5-methyl-5,6-dihydro-4H-2,3,5,10b-tetraaza-benzo[e]azulene The title compound was obtained as white solid in 67% yield from trans-8-chloro-1-[4-(6-ethyl-pyridin-2-yl)-cyclohexyl]-5,6-dihydro-4H-2,3,5,10b-tetraaza-benzo[e]azulene and paraformaldehyde according to general procedure (XII). MS m/e: 422 ([M+H]$^+$)

Example 10 trans-8-Chloro-1-[4-(6-isopropyl-pyridin-2-yl)-cyclohexyl]-4H,6H-2,3,5,10b-tetraaza-benzo[e]azulene-5-carboxylic acid tert-butyl ester The title compound was obtained as light yellow solid in 55% yield according to general procedure (X). Hydrazide: trans-4-(6-Isopropyl-pyridin-2-yl)-cyclohexanecarboxylic acid hydrazide. Thiolactam: 7-Chloro-2-thioxo-1,2,3,5-tetrahydro-benzo[e][1,4]diazepine-4-carboxylic acid tert-butyl ester. MS m/e: 522 ([M+H]$^+$)

Example 11 trans-8-Chloro-1-[4-(6-isopropyl-pyridin-2-yl)-cyclohexyl]-5,6-dihydro-4H-2,3,5,10b-tetraaza-benzo[e]azulene hydrochloride The title compound was obtained as light yellow solid in quantitative yield from trans-8-chloro-1-[4-(6-isopropyl-pyridin-2-yl)-cyclohexyl]-4H,6H-2,3,5,10b-tetraaza-benzo[e]azulene-5-carboxylic acid tert-butyl ester according to general procedure (XI-a). MS m/e: 422 ([M+H]$^+$)

Example 12 trans-8-Chloro-1-[4-(6-isopropyl-pyridin-2-yl)-cyclohexyl]-5-methyl-5,6-dihydro-4H-2,3,5,10b-tetraaza-benzo[e]azulene The title compound was obtained as white solid in 50% yield from trans-8-chloro-1-[4-(6-isopropyl-pyridin-2-yl)-cyclohexyl]-5,6-dihydro-4H-2,3,5,10b-tetraaza-benzo[e]azulene hydrochloride and paraformaldehyde according to general procedure (XII). MS m/e: 436 ([M+H]$^+$)

Example 13 trans-8-Chloro-1-[4-(6-methoxy-pyridin-2-yl)-cyclohexyl]-4H,6H-2,3,5,10b-tetraaza-benzoazulene-5-carboxylic acid tert-butyl ester The title compound was obtained as white solid in 40% yield according to general procedure (X). Hydrazide: trans-4-(6-Methoxy-pyridin-2-yl)-cyclohexanecarboxylic acid hydrazide. Thiolactam: 7-Chloro-2-thioxo-1,2,3,5-tetrahydro-benzo[e][1,4]diazepine-4-carboxylic acid tert-butyl ester. MS m/e: 510 ([M+H]$^+$)

Example 14 trans-8-Chloro-1-[4-(6-methoxy-pyridin-2-yl)-cyclohexyl]-5,6-dihydro-4H-2,3,5,10b-tetraaza-benzo[e]azulene The title compound was obtained as white solid in 53% yield from trans-8-chloro-1-[4-(6-methoxy-pyridin-2-yl)-cyclohexyl]-4H,6H-2,3,5,10b-tetraaza-benzoazulene-5-carboxylic acid tert-butyl ester according to general procedure (XI-a). MS m/e: 410 ([M+H]$^+$)

Example 15 trans-8-Chloro-1-[4-(6-methoxy-pyridin-2-yl)-cyclohexyl]-5-methyl-5,6-dihydro-4H-2,3,5,10b-tetraaza-benzo[e]azulene The title compound was obtained as white solid in 48% yield from trans-8-chloro-1-[4-(6-methoxy-pyridin-2-yl)-cyclohexyl]-5,6-dihydro-4H-2,3,5,10b-tetraaza-benzo[e]azulene and paraformaldehyde according to general procedure (XII). MS m/e: 424 ([M+H]$^+$)

Example 16 trans-8-Chloro-1-[4-(6-chloro-pyridin-2-yl)-cyclohexyl]-4H,6H-2,3,5,10b-tetraaza-benzoazulene-5-carboxylic acid tert-butyl ester The title compound was obtained as white solid in 66% yield according to general procedure (X). Hydrazide: trans-4-(6-Chloro-pyridin-2-yl)-cyclohexanecarboxylic acid hydrazide. Thiolactam: 7-Chloro-2-thioxo-1,2,3,5-tetrahydro-benzo[e][1,4]diazepine-4-carboxylic acid tert-butyl ester. MS m/e: 514.5 ([M+H]$^+$)

Example 17 trans-8-Chloro-1-[4-(6-chloro-pyridin-2-yl)-cyclohexyl]-5,6-dihydro-4H-2,3,5,10b-tetraaza-benzo[e]azulene The title compound was obtained as off-white solid in quantitative yield from trans-8-chloro-1-[4-(6-chloro-pyridin-2-yl)-cyclohexyl]-4H,6H-2,3,5,10b-tetraaza-benzoazulene-5-carboxylic acid tert-butyl ester according to general procedure (XI-b). MS m/e: 414 ([M+H]$^+$)

Example 18 trans-8-Chloro-1-[4-(6-chloro-pyridin-2-yl)-cyclohexyl]-5-methyl-5,6-dihydro-4H-2,3,5,10b-tetraaza-benzo[e]azulene The title compound was obtained as white solid in 41% yield from trans-8-chloro-1-[4-(6-chloro-pyridin-2-yl)-cyclohexyl]-5,6-dihydro-4H-2,3,5,10b-tetraaza-benzo[e]azulene and paraformaldehyde according to general procedure (XII). MS m/e: 428 ([M+H]$^+$)

Example 19 trans-8-Chloro-1-[4-(6-fluoro-pyridin-2-yl)-cyclohexyl]-4H,6H-2,3,5,10b-tetraaza-benzoazulene-5-carboxylic acid tert-butyl ester The title compound was obtained as off-white solid in 69% yield according to general procedure (X). Hydrazide: trans-4-(6-Fluoro-pyridin-2-yl)-cyclohexanecarboxylic acid hydrazide. Thiolactam: 7-Chloro-2-thioxo-1,2,3,5-tetrahydro-benzo[e][1,4]diazepine-4-carboxylic acid tert-butyl ester. MS m/e: 498 ([M+H]$^+$)

Example 20 trans-8-Chloro-1-[4-(6-fluoro-pyridin-2-yl)-cyclohexyl]-5,6-dihydro-4H-2,3,5,10b-tetraaza-benzo[e]azulene The title compound was obtained as off-white solid in quantitative yield from trans-8-chloro-1-[4-(6-fluoro-pyridin-2-yl)-cyclohexyl]-4H,6H-2,3,5,10b-tetraaza-benzoazulene-5-carboxylic acid tert-butyl ester according to general procedure (XI-b). MS m/e: 398 ([M+H]$^+$)

Example 21 trans-8-Chloro-1-[4-(6-fluoro-pyridin-2-yl)-cyclohexyl]-5-methyl-5,6-dihydro-4H-2,3,5,10b-tetraaza-benzo[e]azulene The title compound was obtained as white solid in 63% yield from trans-8-chloro-1-[4-(6-fluoro-pyridin-2-yl)-cyclohexyl]-5,6-dihydro-4H-2,3,5,10b-tetraaza-benzo[e]azulene and paraformaldehyde according to general procedure (XII). MS m/e: 412 ([M+H]$^+$)

Example 22 trans-8-Chloro-1-[4-(5-fluoro-pyridin-2-yl)-cyclohexyl]-4H,6H-2,3,5,10b-tetraaza-benzo[e]azulene-5-carboxylic acid tert-butyl ester The title compound was obtained as light yellow solid in 57% yield according to general procedure (X). Hydrazide: trans-4-(5-Fluoro-pyridin-2-yl)-cyclohexanecarboxylic acid hydrazide Thiolactam: 7-Chloro-2-thioxo-1,2,3,5-tetrahydro-benzo[e][1,4]diazepine-4-carboxylic acid tert-butyl ester. MS m/e: 498 ([M+H]$^+$)

Example 23 trans-8-Chloro-1-[4-(5-fluoro-pyridin-2-yl)-cyclohexyl]-5,6-dihydro-4H-2,3,5,10b-tetraaza-benzo[e]azulene dihydrochloride The title compound was obtained as off-white solid in quantitative yield from trans-8-chloro-1-[4-(5-fluoro-pyridin-2-yl)-cyclohexyl]-4H,6H-2,3,5,10b-tetraaza-benzo[e]azulene-5-carboxylic acid tert-butyl ester according to general procedure (XI-a). MS m/e: 398 ([M+H]$^+$)

Example 24 trans-8-Chloro-1-[4-(5-fluoro-pyridin-2-yl)-cyclohexyl]-5-methyl-5,6-dihydro-4H-2,3,5,10b-tetraaza-benzo[e]azulene The title compound was obtained as white solid in 91% yield from trans-8-chloro-1-[4-(5-fluoro-pyridin-2-yl)-cyclohexyl]-5,6-dihydro-4H-2,3,5,10b-tetraaza-benzo[e]azulene dihydrochloride and paraformaldehyde according to general procedure (XII). MS m/e: 412 ([M+H]$^+$)

Example 25 trans-8-Chloro-1-[4-(4-chloro-pyridin-2-yl)-cyclohexyl]-4H,6H-2,3,5,10b-tetraaza-benzo[e]azulene-5-carboxylic acid tert-butyl ester The title compound was obtained as white solid in 5% yield according to general procedure (X). Hydrazide: cis/trans-4-(4-Chloro-pyridin-2-yl)-cyclohexanecarboxylic acid hydrazide. Thiolactam: 7-Chloro-2-thioxo-1,2,3,5-tetrahydro-benzo[e][1,4]diazepine-4-carboxylic acid tert-butyl ester. MS m/e: 514 ([M+H]$^+$)

Example 26 trans-8-Chloro-1-[4-(4-chloro-pyridin-2-yl)-cyclohexyl]-5,6-dihydro-4H-2,3,5,10b-tetraaza-benzo[e]azulene The title compound was obtained as off-white solid in 87% yield from trans-8-chloro-1-[4-(4-chloro-pyridin-2-yl)-cyclohexyl]-4H,6H-2,3,5,10b-tetraaza-benzo[e]azulene-5-carboxylic acid tert-butyl ester according to general procedure (XI-b). MS m/e: 414 ([M+H]$^+$)

Example 27 trans-8-Chloro-1-[4-(4-chloro-pyridin-2-yl)-cyclohexyl]-5-methyl-5,6-dihydro-4H-2,3,5,10b-tetraaza-benzo[e]azulene The title compound was obtained as white solid in 35% yield from trans-8-chloro-1-[4-(4-chloro-pyridin-2-yl)-cyclohexyl]-5,6-dihydro-4H-2,3,5,10b-tetraaza-benzo[e]azulene and paraformaldehyde according to general procedure (XII). MS m/e: 428 ([M+H]$^+$)

Example 28 trans-8-Chloro-1-[4-(3-fluoro-pyridin-2-yl)-cyclohexyl]-4H,6H-2,3,5,10b-tetraaza-benzo[e]azulene-5-carboxylic acid tert-butyl ester The title compound was obtained as light brown solid in 64% yield according to general procedure (X). Hydrazide: trans-4-(3-Fluoro-pyridin-2-yl)-cyclohexanecarboxylic acid hydrazideThiolactam: 7-Chloro-2-thioxo-1,2,3,5-tetrahydro-benzo[e][1,4]diazepine-4-carboxylic acid tert-butyl ester. MS m/e: 498 ([M+H]$^+$)

Example 29 trans-8-Chloro-1-[4-(3-fluoro-pyridin-2-yl)-cyclohexyl]-5,6-dihydro-4H-2,3,5,10b-tetraaza-benzo[e]azulene The title compound was obtained as off-white solid in 99% yield from trans-8-chloro-1-[4-(3-fluoro-pyridin-2-yl)-cyclohexyl]-4H,6H-2,3,5,10b-tetraaza-benzo[e]azulene-5-carboxylic acid tert-butyl ester according to general procedure (XI-b). MS m/e: 398 ([M+H]$^+$)

Example 30 trans-8-Chloro-1-[4-(3-fluoro-pyridin-2-yl)-cyclohexyl]-5-methyl-5,6-dihydro-4H-2,3,5,10b-tetraaza-benzo[e]azulene The title compound was obtained as white solid in 46% yield from trans-8-chloro-1-[4-(3-fluoro-pyridin-2-yl)-cyclohexyl]-5,6-dihydro-4H-2,3,5,10b-tetraaza-benzo[e]azulene and paraformaldehyde according to general procedure (XII). MS m/e: 412 ([M+H]$^+$)

Example 31 trans-8-Chloro-5-ethyl-[4-(3-fluoro-pyridin-2-yl)-cyclohexyl]-5,6-dihydro-4H-2,3,5,10b-tetraaza-benzo[e]azulene The title compound was obtained as off-white solid in 18% yield from trans-8-chloro-1-[4-(3-fluoro-pyridin-2-yl)-cyclohexyl]-5,6-dihydro-4H-2,3,5,10b-tetraaza-benzo[e]azulene and acetaldehyde according to general procedure (XII). MS m/e: 426 ([M+H]$^+$)

Example 32 trans-8-Chloro-5-isopropyl-[4-(3-fluoro-pyridin-2-yl)-cyclohexyl]-5,6-dihydro-4H-2,3,5,10b-tetraaza-benzo[e]azulene After stirring a solution of trans-8-chloro-1-[4-(3-fluoro-pyridin-2-yl)-cyclohexyl]-5,6-dihydro-4H-2,3,5,10b-tetraaza-benzo[e]azulene (50.0 mg, 0.126 mmol), acetone (0.019 ml, 0.251 mmol) and acetic acid (0.014 ml, 0.25 mmol) in 1,2-dichloroethane (1.3 ml) at room temperature for 5 h, sodium triacetoxyborohydride (58.6 mg, 0.276 mmol) was added. Stirring for further 20 h was followed by quenching with methanol (1 ml) and N-ethyldiisopropylamine (0.044 ml, 0.25 mmol). The reaction mixture was stirred for 30 minutes and concentrated in vacuo. Preparative RP-HPLC with water (0.05% formic acid)/methanol as eluent gave the title compound (40 mg, 72%) as white solid. MS m/e: 440 ([M+H]$^+$)

Example 33 trans-8-Chloro-5-cyclobutyl-[4-(3-fluoro-pyridin-2-yl)-cyclohexyl]-5,6-dihydro-4H-2,3,5,10b-tetraaza-benzo[e]azulene The title compound was obtained as light yellow solid in 36% yield from trans-8-chloro-1-[4-(3-fluoro-pyridin-2-yl)-cyclohexyl]-5,6-dihydro-4H-2,3,5,10b-tetraaza-benzo[e]azulene and cyclobutanone according to general procedure (XII). MS m/e: 452 ([M+H]$^+$)

Example 34 trans-8-Chloro-5-(2,2-difluoro-ethyl)-[4-(3-fluoro-pyridin-2-yl)-cyclohexyl]-5,6-dihydro-4H-2,3,5,10b-tetraaza-benzo[e]azulene A mixture of trans-8-chloro-1-[4-(3-fluoro-pyridin-2-yl)-cyclohexyl]-5,6-dihydro-4H-2,3,5,10b-tetraaza-benzo[e]azulene (50.0 mg, 0.126 mmol), cesium carbonate (81.9 mg, 0.251 mmol) and 2,2-difluoroethyl trifluoromethanesulfonate (53.8 mg, 0.251 mmol) in acetonitrile (0.6 ml) was stirred at room temperature for 20 h. The reaction mixture was partitioned between a water-brine mixture (1:1) (2 ml) and ethyl acetate (5 ml). The layers were separated. The aqueous layer was extracted with two 5-ml portions of ethyl acetate. The combined organic layers were concentrated in vacuo. Preparative RP-HPLC with water (0.05% formic acid)/methanol as eluent gave the title compound (24 mg, 37%) as off-white solid. MS m/e: 462 ([M+H]$^+$)

Example 35 trans-8-Chloro-1-[4-(3-fluoro-pyridin-2-yl)-cyclohexyl]-5-(2-methoxy-ethyl)-5,6-dihydro-4H-2,3,5,10b-tetraaza-benzo[e]azulene A mixture of trans-8-chloro-1-[4-(3-fluoro-pyridin-2-yl)-cyclohexyl]-5,6-dihydro-4H-2,3,5,10b-tetraaza-benzo[e]azulene (50.0 mg, 0.126 mmol), cesium carbonate (81.9 mg, 0.251 mmol) and 2-bromoethyl methyl ether (0.024 ml, 0.25 mmol) in acetonitrile (0.6 ml) was heated at 70° C. for 20 h. The reaction mixture was partitioned between a water-brine mixture (1:1) (2 ml) and ethyl acetate (5 ml). The layers were separated. The aqueous layer was extracted with two 5-ml portions of ethyl acetate. The combined organic layers were concentrated in vacuo. Preparative RP-HPLC with water (0.05% formic acid)/methanol as eluent gave the title compound (13 mg, 23%) as light yellow solid. MS m/e: 456 ([M+H]$^+$)

Example 36 trans-(2-{8-Chloro-1-[4-(3-fluoro-pyridin-2-yl)-cyclohexyl]-4H,6H-2,3,5,10b-tetraaza-benzo[e]azulen-5-yl}-ethyl)-methyl-amine A mixture of trans-8-chloro-1-[4-(3-fluoro-pyridin-2-yl)-cyclohexyl]-5,6-dihydro-4H-2,3,5,10b-tetraaza-benzo[e]azulene (50.0 mg, 0.126 mmol), cesium carbonate (246 mg, 0.754 mmol) and 2-methylaminoethyl chloride hydrochloride (65.4 mg, 0.503 mmol) in acetonitrile (1.3 ml) was heated at 70° C. for 20 h. After addition of further portions of cesium carbonate (246 mg, 0.754 mmol) and 2-methylaminoethyl chloride hydrochloride (65.4 mg, 0.503 mmol) the mixture was heated at 70° C. for another 20 h. The reaction mixture was partitioned between 1 M aqueous sodium hydroxide solution (2 ml) and ethyl acetate (5 ml). The layers were separated. The aqueous layer was extracted with two 5-ml portions of ethyl acetate. The combined organic layers were concentrated in vacuo. Preparative RP-HPLC with water (0.05% formic acid)/methanol as eluent gave the title compound as formate salt. The salt was partitioned between ethyl acetate (15 ml) and 1 M aqueous sodium hydroxide solution (10 ml). The layers were separated. The aqueous layer was extracted with two 15 ml-portions of ethyl acetate. The combined organic layers were dried over anhydrous sodium sulfate and concentrated in vacuo to give the title compound (14 mg, 25%) as off-white solid. MS m/e: 455 ([M+H]$^+$)

Example 37 trans-1-{8-Chloro-1-[4-(3-fluoro-pyridin-2-yl)-cyclohexyl]-4H,6H-2,3,5,10b-tetraaza-benzo[e]azulen-5-yl}-ethanone To a solution of trans-8-chloro-1-[4-(3-fluoro-pyridin-2-yl)-cyclohexyl]-5,6-dihydro-4H-2,3,5,10b-tetraaza-benzo[e]azulene (50.0 mg, 0.126 mmol) and triethylamine (0.035 ml, 0.25 mmol) in dichloromethane (0.6 ml) was added acetyl chloride (0.18 ml, 0.251 mmol) at room temperature. Stirring for 20 h was followed by partitioning between a water-brine mixture (1:1) (2 ml) and ethyl acetate (5 ml). The layers were separated. The aqueous layer was extracted with two 5 ml-portions of ethyl acetate. The combined organic layers were concentrated in vacuo. Preparative RP-HPLC with water (0.05% formic acid)/methanol as eluent gave the title compound (7 mg, 12%) as off-white solid. MS m/e: 440 ([M+H]$^+$)

Example 38 trans-1-{8-Chloro-1-[4-(3-fluoro-pyridin-2-yl)-cyclohexyl]-4H,6H-2,3,5,10b-tetraaza-benzo[e]azulen-5-yl}-2-hydroxy-ethanone A solution of glycolic acid (11.5 mg, 0.151 mmol) and HATU (57.3 mg, 0.151 mmol) in N,N-dimethylformamide (1.0 ml) was stirred at room temperature for 5 minutes. trans-8-Chloro-1-[4-(3-fluoro-pyridin-2-yl)-cyclohexyl]-5,6-dihydro-4H-2,3,5,10b-tetraaza-benzo[e]azulene (50.0 mg, 0.126 mmol) and N-ethyldiisopropylamine (0.053 ml, 0.30 mmol) were added consecutively. The reaction mixture was stirred for 1 h. Preparative RP-HPLC with water (0.05% formic acid)/methanol as eluent gave the title compound (41 mg, 71%) as white solid. MS m/e: 456 ([M+H]$^+$)

Example 39 trans-1-{8-Chloro-1-[4-(3-fluoro-pyridin-2-yl)-cyclohexyl]-4H,6H-2,3,5,10b-tetraaza-benzo[e]azulen-5-yl}-2-dimethylamino-ethanone formate A solution of N,N-dimethylglycine (11.5 mg, 0.151 mmol) and HATU (57.3 mg, 0.151 mmol) in N,N-dimethylformamide (1.0 ml) was stirred for 5 minutes at room temperature. trans-8-Chloro-1-[4-(3-fluoro-pyridin-2-yl)-cyclohexyl]-5,6-dihydro-4H-2,3,5,10b-tetraaza-benzo[e]azulene (50.0 mg, 0.126 mmol) and N-ethyldiisopropylamine (0.053 ml, 0.30 mmol) were added consecutively. The reaction mixture was stirred for 1 h. Preparative RP-HPLC with water (0.05% formic acid)/methanol as eluent gave the title compound (51 mg, 77%) as white solid. MS m/e: 483 ([M+H]$^+$)

Example 40 trans-8-Chloro-1-[4-(3-fluoro-pyridin-2-yl)-cyclohexyl]-5-methanesulfonyl-5,6-dihydro-4H-2,3,5,10b-tetraaza-benzo[e]azulene To a solution of trans-8-chloro-1-[4-(3-fluoro-pyridin-2-yl)-cyclohexyl]-5,6-dihydro-4H-2,3,5,10b-tetraaza-benzo[e]azulene (50.0 mg, 0.126 mmol) and triethylamine (0.035 ml, 0.25 mmol) in dichloromethane (0.6 ml) was added methanesulfonyl chloride (0.20 ml, 0.25 mmol) at room temperature. Stirring for 20 h was followed by partitioning between a water-brine mixture (1:1) (2 ml) and ethyl acetate (5 ml). The layers were separated. The aqueous layer was extracted with two 5 ml-portions of ethyl acetate. The combined organic layers were concentrated in vacuo. Preparative RP-HPLC with water (0.05% formic acid)/methanol as eluent gave the title compound (46 mg, 77%) as white solid. MS m/e: 476 ([M+H]$^+$)

Example 41 trans-8-Chloro-1-[4-(3-fluoro-pyridin-2-yl)-cyclohexyl]-4H,6H-2,3,5,10b-tetraaza-benzo[e]azulene-5-sulfonic acid dimethylamide To a solution of trans-8-chloro-1-[4-(3-fluoro-pyridin-2-yl)-cyclohexyl]-5,6-dihydro-4H-2,3,5,10b-tetraaza-benzo[e]azulene (50.0 mg, 0.126 mmol) and triethylamine (0.035 ml, 0.251 mmol) in dichloromethane (0.6 ml) was added dimethyl sulfamoyl chloride (0.27 ml, 0.251 mmol) at room temperature. Stirring for 20 h was followed by quenching with methanol (0.5 ml). The mixture was concentrated in vacuo. Preparative RP-HPLC with water (0.05% formic acid)/methanol as eluent gave the title compound (39 mg, 61%) as white solid. MS m/e: 505 ([M+H]$^+$)

Example 42 trans-8-Fluoro-[4-(3-fluoro-pyridin-2-yl)-cyclohexyl]-4H,6H-2,3,5,10b-tetraaza-benzo[e]azulene-5-carboxylic acid tert-butyl ester The title compound was obtained as white solid in 60% yield according to general procedure (X). Hydrazide: trans-4-(3-Fluoro-pyridin-2-yl)-cyclohexanecarboxylic acid hydrazide. Thiolactam: 7-Fluoro-2-thioxo-1,2,3,5-tetrahydro-benzo[e][1,4]diazepine-4-carboxylic acid tert-butyl ester. MS m/e: 482 ([M+H]$^+$)

Example 43 trans-8-Fluoro-[4-(3-fluoro-pyridin-2-yl)-cyclohexyl]-5,6-dihydro-4H-2,3,5,10b-tetraaza-benzo[e]azulene The title compound was obtained as white solid in 76% yield from trans-8-fluoro-[4-(3-fluoro-pyridin-2-yl)-cyclohexyl]-4H,6H-2,3,5,10b-tetraaza-benzo[e]azulene-5-carboxylic acid tert-butyl ester according to general procedure (XI-b). MS m/e: 398 ([M+H]$^+$)

Example 44 trans-8-Fluoro-[4-(3-fluoro-pyridin-2-yl)-cyclohexyl]-5-methyl-5,6-dihydro-4H-2,3,5,10b-tetraaza-benzo[e]azulene The title compound was obtained as white solid in 46% yield from trans-8-fluoro-[4-(3-fluoro-pyridin-2-yl)-cyclohexyl]-5,6-dihydro-4H-2,3,5,10b-tetraaza-benzo[e]azulene and paraformaldehyde according to general procedure (XII). MS m/e: 396 ([M+H]$^+$)

Example 45 cis-8-Chloro-1-[4-(3-fluoro-pyridin-2-yl)-cyclohexyl]-4H,6H-2,3,5,10b-tetraaza-benzo[e]azulene-5-carboxylic acid tert-butyl ester The title compound was obtained as off-white solid in 51% yield according to general procedure (X). Hydrazide: cis/trans-4-(3-Fluoro-pyridin-2-yl)-cyclohexanecarboxylic acid hydrazide (7.8:1). Thiolactam: 7-Chloro-2-thioxo-1,2,3,5-tetrahydro-benzo[e][1,4]diazepine-4-carboxylic acid tert-butyl ester. MS m/e: 498 ([M+H]$^+$)

Example 46 cis-8-Chloro-1-[4-(3-fluoro-pyridin-2-yl)-cyclohexyl]-5,6-dihydro-4H-2,3,5,10b-tetraaza-benzo[e]azulene The title compound was obtained as off-white solid in 78% yield from cis-8-chloro-1-[4-(3-fluoro-pyridin-2-yl)-cyclohexyl]-4H,6H-2,3,5,10b-tetraaza-benzo[e]azulene-5-carboxylic acid tert-butyl ester according to general procedure (XI-b). MS m/e: 398 ([M+H]$^+$)

Example 47 cis-8-Chloro-1-[4-(3-fluoro-pyridin-2-yl)-cyclohexyl]-5-methyl-5,6-dihydro-4H-2,3,5,10b-tetraaza-benzo[e]azulene The title compound was obtained as white solid in 88% yield from cis-8-chloro-1-[4-(3-fluoro-pyridin-2-yl)-cyclohexyl]-5,6-dihydro-4H-2,3,5,10b-tetraaza-benzo[e]azulene and paraformaldehyde according to general procedure (XII). MS m/e: 412 ([M+H]$^+$)

Example 48 trans-8-Chloro-1-(4-pyridin-3-yl-cyclohexyl)-4H,6H-2,3,5,10b-tetraaza-benzo[e]azulene-5-carboxylic acid tert-butyl ester The title compound was obtained as light yellow solid in 81% yield according to general procedure (X). Hydrazide: trans-4-Pyridin-3-yl-cyclohexanecarboxylic acid hydrazide Thiolactam: 7-Chloro-2-thioxo-1,2,3,5-tetrahydro-benzo[e][1,4]diazepine-4-carboxylic acid tert-butyl ester. MS m/e: 480 ([M+H]$^+$)

Example 49 trans-8-Chloro-1-(4-pyridin-3-yl-cyclohexyl)-5,6-dihydro-4H-2,3,5,10b-tetraaza-benzo[e]azulene The title compound was obtained as light yellow solid in 94% yield from trans-8-chloro-1-(4-pyridin-3-yl-cyclohexyl)-4H,6H-2,3,5,10b-tetraaza-benzo[e]azulene-5-carboxylic acid tert-butyl ester according to general procedure (XI-a). MS m/e: 380 ([M+H]$^+$)

Example 50 trans-8-Chloro-5-methyl-1-(4-pyridin-3-yl-cyclohexyl)-5,6-dihydro-4H-2,3,5,10b-tetraaza-benzo[e]azulene The title compound was obtained as white solid in 88% yield from trans-8-chloro-1-(4-pyridin-3-yl-cyclohexyl)-5,6-dihydro-4H-2,3,5,10b-tetraaza-benzo[e]azulene and paraformaldehyde according to general procedure (XII). MS m/e: 394 ([M+H]$^+$)

Example 51 trans-8-Chloro-1-[4-(2-chloro-pyridin-3-yl)-cyclohexyl]-4H,6H-2,3,5,10b-tetraaza-benzo[e]azulene-5-carboxylic acid tert-butyl ester The title compound was obtained as light yellow solid in 84% yield according to general procedure (X). Hydrazide: trans-4-(2-Chloro-pyridin-3-yl)-cyclohexanecarboxylic acid hydrazide. Thiolactam: 7-Chloro-2-thioxo-1,2,3,5-tetrahydro-benzo[e][1,4]diazepine-4-carboxylic acid tert-butyl ester. MS m/e: 514 ([M+H]$^+$)

Example 52 trans-8-Chloro-1-[4-(2-chloro-pyridin-3-yl)-cyclohexyl]-5,6-dihydro-4H-2,3,5,10b-tetraaza-benzo[e]azulene The title compound was obtained as off-white solid in 98% yield from trans-8-chloro-1-[4-(2-chloro-pyridin-3-yl)-cyclohexyl]-4H,6H-2,3,5,10b-tetraaza-benzo[e]azulene-5-carboxylic acid tert-butyl ester according to general procedure (XI-b). MS m/e: 414 ([M+H]$^+$)

Example 53 trans-8-Chloro-1-[4-(2-chloro-pyridin-3-yl)-cyclohexyl]-5-methyl-5,6-dihydro-4H-2,3,5,10b-tetraaza-benzo[e]azulene The title compound was obtained as white solid in 50% yield from trans-8-chloro-1-[4-(2-chloro-pyridin-3-yl)-cyclohexyl]-5,6-dihydro-4H-2,3,5,10b-tetraaza-benzo[e]azulene and paraformaldehyde according to general procedure (XII). MS m/e: 428 ([M+H]$^+$)

Example 54 trans-8-Chloro-1-[4-(2-fluoro-pyridin-3-yl)-cyclohexyl]-4H,6H-2,3,5,10b-tetraaza-benzo[e]azulene-5-carboxylic acid tert-butyl ester The title compound was obtained as yellow solid in 65% yield according to general procedure (X). Hydrazide:trans-4-(2-Fluoro-pyridin-3-yl)-cyclohexanecarboxylic acid hydrazide Thiolactam: 7-Chloro-2-thioxo-1,2,3,5-tetrahydro-benzo[e][1,4]diazepine-4-carboxylic acid tert-butyl ester. MS m/e: 498 ([M+H]$^+$)

Example 55 trans-8-Chloro-1-[4-(2-fluoro-pyridin-3-yl)-cyclohexyl]-5,6-dihydro-4H-2,3,5,10b-tetraaza-benzo[e]azulene The title compound was obtained as yellow solid in quantitative yield from trans-8-chloro-1-[4-(2-fluoro-pyridin-3-yl)-cyclohexyl]-4H,6H-2,3,5,10b-tetraaza-benzo[e]azulene-5-carboxylic acid tert-butyl ester according to general procedure (XI-b). MS m/e: 398 ([M+H]$^+$)

Example 56 trans-8-Chloro-1-[4-(2-fluoro-pyridin-3-yl)-cyclohexyl]-5-methyl-5,6-dihydro-4H-2,3,5,10b-tetraaza-benzo[e]azulene The title compound was obtained as white solid in 53% yield from trans-8-chloro-1-[4-(2-fluoro-pyridin-3-yl)-cyclohexyl]-5,6-dihydro-4H-2,3,5,10b-tetraaza-benzo[e]azulene and paraformaldehyde according to general procedure (XII). MS m/e: 412 ([M+H]$^+$)

Example 57 trans-8-Chloro-1-(4-pyrimidin-2-yl-cyclohexyl)-4H, 6H-2,3,5,10b-tetraaza-benzo[e]azulene-5-carboxylic acid tert-butyl ester and

Example 58 cis-8-Chloro-1-(4-pyrimidin-2-yl-cyclohexyl)-4H, 6H-2,3,5,10b-tetraaza-benzo[e]azulene-5-carboxylic acid tert-butyl ester trans-8-Chloro-1-(4-pyrimidin-2-yl-cyclohexyl)-4H,6H-2,3,5,10b-tetraaza-benzo[e]azulene-5-carboxylic acid tert-butyl ester and cis-8-chloro-1-(4-pyrimidin-2-yl-cyclohexyl)-4H,6H-2,3,5,10b-tetraaza-benzo[e]azulene-5-carboxylic acid tert-butyl ester were obtained according to general procedure (X) after chromatographic separation. Hydrazide: cis/trans-4-Pyrimidin-2-yl-cyclohexanecarboxylic acid hydrazide Thiolactam: 7-Chloro-2-thioxo-1,2,3,5-tetrahydro-benzo[e][1,4]diazepine-4-carboxylic acid tert-butyl ester.

trans-8-Chloro-1-(4-pyrimidin-2-yl-cyclohexyl)-4H,6H-2,3,5,10b-tetraaza-benzo[e]azulene-5-carboxylic acid tert-butyl ester was obtained as white solid in 19% yield. MS m/e: 481 ([M+H]$^+$)

cis-8-Chloro-1-(4-pyrimidin-2-yl-cyclohexyl)-4H,6H-2,3,5,10b-tetraaza-benzo[e]azulene-5-carboxylic acid tert-butyl ester was obtained as white solid in 36% yield. MS m/e: 481 ([M+H]$^+$)

Example 59 trans-8-Chloro-1-(4-pyrimidin-2-yl-cyclohexyl)-5,6-dihydro-4H-2,3,5,10b-tetraaza-benzo[e]azulene The title compound was obtained as white solid in quantitative yield from trans-8-chloro-1-(4-pyrimidin-2-yl-cyclohexyl)-4H,6H-2,3,5,10b-tetraaza-benzo[e]azulene-5-carboxylic acid tert-butyl ester according to general procedure (XI-a). MS m/e: 381 ([M+H]$^+$)

Example 60 trans-8-Chloro-5-methyl-1-(4-pyrimidin-2-yl-cyclohexyl)-5,6-dihydro-4H-2,3,5,10b-tetraaza-benzo[e]azulene The title compound was obtained as white solid in 77% yield from trans-8-chloro-1-(4-pyrimidin-2-yl-cyclohexyl)-5,6-dihydro-4H-2,3,5,10b-tetraaza-benzo[e]azulene and paraformaldehyde according to general procedure (XII). MS m/e: 395 ([M+H]$^+$)

Example 61 cis-8-Chloro-1-(4-pyrimidin-2-yl-cyclohexyl)-5,6-dihydro-4H-2,3,5,10b-tetraaza-benzo[e]azulene The title compound was obtained as white solid in 95% yield from cis-8-chloro-1-(4-pyrimidin-2-yl-cyclohexyl)-4H,6H-2,3,5,10b-tetraaza-benzo[e]azulene-5-carboxylic acid tert-butyl ester according to general procedure (XI-a). MS m/e: 381 ([M+H]$^+$)

Example 62 cis-8-Chloro-5-methyl-1-(4-pyrimidin-2-yl-cyclohexyl)-5,6-dihydro-4H-2,3,5,10b-tetraaza-benzo[e]azulene The title compound was obtained as white solid in 21% yield from cis-8-chloro-1-(4-pyrimidin-2-yl-cyclohexyl)-5,6-dihydro-4H-2,3,5,10b-tetraaza-benzo[e]azulene and paraformaldehyde according to general procedure (XII). MS m/e: 395 ([M+H]$^+$)

Example 63 trans-8-Chloro-1-[4-(4,6-dimethyl-pyrimidin-2-yl)-cyclohexyl]-4H,6H-2,3,5,10b-tetraaza-benzo[e]azulene-5-carboxylic acid tert-butyl ester The title compound was obtained as white solid in 70% yield according to general procedure (X). Hydrazide: trans-4-(4,6-Dimethyl-pyrimidin-2-yl)-cyclohexanecarboxylic acid hydrazide. Thiolactam: 7-Chloro-2-thioxo-1,2,3,5-tetrahydro-benzo[e][1,4]diazepine-4-carboxylic acid tert-butyl ester. MS m/e: 509 ([M+H]$^+$)

Example 64 trans-8-Chloro-1-[4-(4,6-dimethyl-pyrimidin-2-yl)-cyclohexyl]-5,6-dihydro-4H-2,3,5,10b-tetraaza-benzo[e]azulene hydrochloride The title compound was obtained as off-white solid in quantitative yield from trans-8-chloro-1-[4-(4,6-dimethyl-pyrimidin-2-yl)-cyclohexyl]-4H,6H-2,3,5,10b-tetraaza-benzo[e]azulene-5-carboxylic acid tert-butyl ester according to general procedure (XI-a). MS m/e: 409 ([M+H]$^+$)

Example 65 trans-8-Chloro-1-[4-(4,6-dimethyl-pyrimidin-2-yl)-cyclohexyl]-5-methyl-5,6-dihydro-4H-2,3,5,10b-tetraaza-benzo[e]azulene The title compound was obtained as white solid in 62% yield from trans-8-chloro-1-[4-(4,6-dimethyl-pyrimidin-2-yl)-cyclohexyl]-5,6-dihydro-4H-2,3,5,10b-tetraaza-benzo[e]azulene hydrochloride and paraformaldehyde according to general procedure (XII). MS m/e: 423 ([M+H]$^+$)

Example 66 trans-8-Chloro-1-[4-(2-methyl-pyrimidin-4-yl)-cyclohexyl]-4H,6H-2,3,5,10b-tetraaza-benzo[e]azulene-5-carboxylic acid tert-butyl ester The title compound was obtained as white solid in 61% yield according to general procedure (X). Hydrazide: trans-4-(2-Methyl-pyrimidin-4-yl)-cyclohexanecarboxylic acid hydrazide. Thiolactam: 7-Chloro-2-thioxo-1,2,3,5-tetrahydro-benzo[e][1,4]diazepine-4-carboxylic acid tert-butyl ester. MS m/e: 495 ([M+H]$^+$)

Example 67 trans-8-Chloro-1-[4-(2-methyl-pyrimidin-4-yl)-cyclohexyl]-5,6-dihydro-4H-2,3,5,10b-tetraaza-benzo[e]azulene The title compound was obtained as off-white solid in quantitative yield from trans-8-chloro-1-[4-(4,6-dimethyl-pyrimidin-2-yl)-cyclohexyl]-4H,6H-2,3,5,10b-tetraaza-benzo[e]azulene-5-carboxylic acid tert-butyl ester according to general procedure (XI-a). MS m/e: 395 ([M+H]$^+$)

Example 68 trans-8-Chloro-5-methyl-1-[4-(2-methyl-pyrimidin-4-yl)-cyclohexyl]-5,6-dihydro-4H-2,3,5,10b-tetraaza-benzo[e]azulene The title compound was obtained as white solid in 83% yield from trans-8-chloro-1-[4-(2-methyl-pyrimidin-4-yl)-cyclohexyl]-5,6-dihydro-4H-2,3,5,10b-tetraaza-benzo[e]azulene and paraformaldehyde according to general procedure (XII). MS m/e: 409 ([M+H]$^+$)

Example 69 trans-8-Chloro-1-(4-pyrazin-2-yl-cyclohexyl)-4H,6H-2,3,5,10b-tetraaza-benzo[e]azulene-5-carboxylic acid tert-butyl ester The title compound was obtained as light brown solid in 41% yield according to general procedure (X). Hydrazide: trans-4-(Pyrazin-2-yl)-cyclohexanecarboxylic acid hydrazide Thiolactam: 7-Chloro-2-thioxo-1,2,3,5-tetrahydro-benzo[e][1,4]diazepine-4-carboxylic acid tert-butyl ester. MS m/e: 481 ([M+H]$^+$)

Example 70 trans-8-Chloro-1-(4-pyrazin-2-yl-cyclohexyl)-5,6-dihydro-4H-2,3,5,10b-tetraaza-benzo[e]azulene The title compound was obtained as yellow solid in 83% yield from trans-8-chloro-1-(4-pyrazin-2-yl-cyclohexyl)-4H,6H-2,3,5,10b-tetraaza-benzo[e]azulene-5-carboxylic acid tert-butyl ester according to general procedure (XI-a). MS m/e: 381 ([M+H]$^+$)

Example 71 trans-8-Chloro-5-methyl-1-(4-pyrazin-2-yl-cyclohexyl)-5,6-dihydro-4H-2,3,5,10b-tetraaza-benzo[e]azulene The title compound was obtained as white solid in 59% yield from trans-8-chloro-1-(4-pyrazin-2-yl-cyclohexyl)-5,6-dihydro-4H-2,3,5,10b-tetraaza-benzo[e]azulene and paraformaldehyde according to general procedure (XII). MS m/e: 395 ([M+H]$^+$)

Example 72 trans-8-Chloro-1-[4-(6-methyl-pyrazin-2-yl)-cyclohexyl]-4H,6H-2,3,5,10b-tetraaza-benzo[e]azulene-5-carboxylic acid tert-butyl ester The title compound was obtained as white solid in 73% yield according to general procedure (X). Hydrazide: trans-4-(6-Methyl-pyrazin-2-yl)-cyclohexanecarboxylic acid hydrazide. Thiolactam: 7-Chloro-2-thioxo-1,2,3,5-tetrahydro-benzo[e][1,4]diazepine-4-carboxylic acid tert-butyl ester. MS m/e: 495 ([M+H]$^+$)

Example 73 trans-8-Chloro-1-[4-(6-methyl-pyrazin-2-yl)-cyclohexyl]-5,6-dihydro-4H-2,3,5,10b-tetraaza-benzo[e]azulene The title compound was obtained as white solid in quantitative yield from trans-8-chloro-1-[4-(6-methyl-pyrazin-2-yl)-cyclohexyl]-4H,6H-2,3,5,10b-tetraaza-benzo[e]azulene-5-carboxylic acid tert-butyl ester according to general procedure (XI-a). MS m/e: 395 ([M+H]$^+$)

Example 74 trans-8-Chloro-5-methyl-1-[4-(6-methyl-pyrazin-2-yl)-cyclohexyl]-5,6-dihydro-4H-2,3,5,10b-tetraaza-benzo[e]azulene The title compound was obtained as white solid in 76% yield from trans-8-chloro-1-[4-(6-methyl-pyrazin-2-yl)-cyclohexyl]-5,6-dihydro-4H-2,3,5,10b-tetraaza-benzo[e]azulene and paraformaldehyde according to general procedure (XII). MS m/e: 409 ([M+H]$^+$)

Example 75 trans-8-Chloro-1-[4-(3-methyl-pyrazin-2-yl)-cyclohexyl]-4H,6H-2,3,5,10b-tetraaza-benzo[e]azulene-5-carboxylic acid tert-butyl ester The title compound was obtained as light yellow solid in 50% yield according to general procedure (X). Hydrazide: trans-4-(3-Methyl-pyrazin-2-yl)-cyclohexanecarboxylic acid hydrazide. Thiolactam: 7-Chloro-2-thioxo-1,2,3,5-tetrahydro-benzo[e][1,4]diazepine-4-carboxylic acid tert-butyl ester. MS m/e: 495 ([M+H]$^+$)

Example 76 trans-8-Chloro-1-[4-(3-methyl-pyrazin-2-yl)-cyclohexyl]-5,6-dihydro-4H-2,3,5,10b-tetraaza-benzo[e]azulene The title compound was obtained as yellow solid in quantitative yield from trans-8-chloro-1-[4-(3-methyl-pyrazin-2-yl)-cyclohexyl]-4H,6H-2,3,5,10b-tetraaza-benzo[e]azulene-5-carboxylic acid tert-butyl ester according to general procedure (XI-a). MS m/e: 395 ([M+H]$^+$)

Example 77 trans-8-Chloro-5-methyl-1-[4-(3-methyl-pyrazin-2-yl)-cyclohexyl]-5,6-dihydro-4H-2,3,5,10b-tetraaza-benzo[e]azulene The title compound was obtained as white solid in 59% yield from trans-8-chloro-1-[4-(3-methyl-pyrazin-2-yl)-cyclohexyl]-5,6-dihydro-4H-2,3,5,10b-tetraaza-benzo[e]azulene and paraformaldehyde according to general procedure (XII). MS m/e: 409 ([M+H]$^+$)

Example 78 trans-8-Chloro-1-[4-(3,6-dimethyl-pyrazin-2-yl)-cyclohexyl]-4H,6H-2,3,5,10b-tetraaza-benzo[e]azulene-5-carboxylic acid tert-butyl ester The title compound was obtained as light yellow solid in 72% yield according to general procedure (X). Hydrazide: trans-4-(3,6-Dimethyl-pyrazin-2-yl)-cyclohexanecarboxylic acid hydrazide. Thiolactam: 7-Chloro-2-thioxo-1,2,3,5-tetrahydro-benzo[e][1,4]diazepine-4-carboxylic acid tert-butyl ester. MS m/e: 509 ([M+H]$^+$)

Example 79 trans-8-Chloro-1-[4-(3,6-dimethyl-pyrazin-2-yl)-cyclohexyl]-5,6-dihydro-4H-2,3,5,10b-tetraaza-benzo[e]azulene hydrochloride The title compound was obtained as light yellow solid in quantitative yield from trans-8-chloro-1-[4-(3,6-dimethyl-pyrazin-2-yl)-cyclohexyl]-4H,6H-2,3,5,10b-tetraaza-benzo[e]azulene-5-carboxylic acid tert-butyl ester according to general procedure (XI-a). MS m/e: 409 ([M+H]$^+$)

Example 80 trans-8-Chloro-1-[4-(3,6-dimethyl-pyrazin-2-yl)-cyclohexyl]-5-methyl-5,6-dihydro-4H-2,3,5,10b-tetraaza-benzo[e]azulene The title compound was obtained as white solid in 24% yield from trans-8-chloro-1-[4-(3,6-dimethyl-pyrazin-2-yl)-cyclohexyl]-5,6-dihydro-4H-2,3,5,10b-tetraaza-benzo[e]azulene hydrochloride and paraformaldehyde according to general procedure (XII). MS m/e: 423 ([M+H]$^+$)

Example 81 trans-8-Chloro-5-methyl-1-(4-pyridazin-3-yl-cyclohexyl)-5,6-dihydro-4H-2,3,5,10b-tetraaza-benzo[e]azulene a) cis/trans-8-Chloro-1-(4-pyridazin-3-yl-cyclohexyl)-4H,6H-2,3,5,10b-tetraaza-benzo[e]azulene-5-carboxylic acid tert-butyl ester The title compound was obtained as off-white solid in 59% yield according to general procedure (X). Hydrazide: cis/trans-4-Pyridazin-3-yl-cyclohexanecarboxylic acid hydrazide Thiolactam: 7-Chloro-2-thioxo-1,2,3,5-tetrahydro-benzo[e][1,4]diazepine-4-carboxylic acid tert-butyl ester. MS m/e: 481 ([M+H]$^+$)

b) cis/trans-8-Chloro-1-(4-pyridazin-3-yl-cyclohexyl)-5,6-dihydro-4H-2,3,5,10b-tetraaza-benzo[e]azulene hydrochloride The title compound was obtained as light yellow solid in quantitative yield from cis/trans-8-chloro-1-(4-pyridazin-3-yl-cyclohexyl)-4H,6H-2,3,5,10b-tetraaza-benzo[e]azulene-5-carboxylic acid tert-butyl ester according to general procedure (XI-a). MS m/e: 381 ([M+H]$^+$)

c) trans-8-Chloro-5-methyl-1-(4-pyridazin-3-yl-cyclohexyl)-5,6-dihydro-4H-2,3,5,10b-tetraaza-benzo[e]azulene The title compound was obtained as light yellow solid in 15% yield from cis/trans-8-chloro-1-(4-pyridazin-3-yl-cyclohexyl)-5,6-dihydro-4H-2,3,5,10b-tetraaza-benzo[e]azulene hydrochloride and paraformaldehyde according to general procedure (XII). MS m/e: 395 ([M+H]$^+$)

Example 82 trans-8-Chloro-1-[4-(3-chloro-pyridin-2-yl)-cyclohexyl]-4H,6H-2,3,5,10b-tetraaza-benzo[e]azulene-5-carboxylic acid tert-butyl ester The title compound was obtained as white solid in 70% yield according to general procedure (X). Hydrazide: trans-4-(3-Chloro-pyridin-2-yl)-cyclohexanecarboxylic acid hydrazide. Thiolactam: 7-Chloro-2-thioxo-1,2,3,5-tetrahydro-benzo[e][1,4]diazepine-4-carboxylic acid tert-butyl ester. MS m/e: 514 ([M+H]$^+$)

Example 83 trans-8-Chloro-1-[4-(3-chloro-pyridin-2-yl)-cyclohexyl]-5,6-dihydro-4H-2,3,5,10b-tetraaza-benzo[e]azulene The title compound was obtained as white solid in 99% yield from trans-8-chloro-1-[4-(3-chloro-pyridin-2-yl)-cyclohexyl]-4H,6H-2,3,5,10b-tetraaza-benzo[e]azulene-5-carboxylic acid tert-butyl ester according to general procedure (XI-b). MS m/e: 414 ([M+H]$^+$)

Example 84 trans-8-Chloro-1-[4-(3-chloro-pyridin-2-yl)-cyclohexyl]-5-methyl-5,6-dihydro-4H-2,3,5,10b-tetraaza-benzo[e]azulene The title compound was obtained as white solid in 83% yield from trans-8-chloro-1-[4-(3-chloro-pyridin-2-yl)-cyclohexyl]-5,6-dihydro-4H-2,3,5,10b-tetraaza-benzo[e]azulene according to general procedure (XIII). MS m/e: 428 ([M+H]$^+$)

Example 85 trans-8-Chloro-1-[4-(3,5-difluoro-pyridin-2-yl)-cyclohexyl]-4H,6H-2,3,5,10b-tetraaza-benzo[e]azulene-5-carboxylic acid tert-butyl ester The title compound was obtained as white solid in 76% yield according to general procedure (X). Hydrazide: trans-4-(3,5-Difluoro-pyridin-2-yl)-cyclohexanecarboxylic acid hydrazide. Thiolactam: 7-Chloro-2-thioxo-1,2,3,5-tetrahydro-benzo[e][1,4]diazepine-4-carboxylic acid tert-butyl ester. MS m/e: 516 ([M+H]$^+$)

Example 86 trans-8-Chloro-1-[4-(3,5-difluoro-pyridin-2-yl)-cyclohexyl]-5,6-dihydro-4H-2,3,5,10b-tetraaza-benzo[e]azulene The title compound was obtained as white solid in quantitative yield from trans-8-chloro-1-[4-(3,5-difluoro-pyridin-2-yl)-cyclohexyl]-4H,6H-2,3,5,10b-tetraaza-benzo[e]azulene-5-carboxylic acid tert-butyl ester according to general procedure (XI-b). MS m/e: 416 ([M+H]$^+$)

Example 87 trans-8-Chloro-1-[4-(3,5-difluoro-pyridin-2-yl)-cyclohexyl]-5-methyl-5,6-dihydro-4H-2,3,5,10b-tetraaza-benzo[e]azulene The title compound was obtained as white solid in 72% yield from trans-8-chloro-1-[4-(3,5-difluoro-pyridin-2-yl)-cyclohexyl]-5,6-dihydro-4H-2,3,5,10b-tetraaza-benzo[e]azulene according to general procedure (XIII). MS m/e: 430 ([M+H]$^+$)

The invention claimed is:
1. A compound of formula I

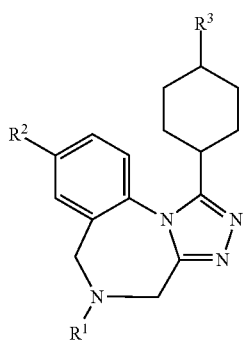

wherein
$R^1$ is selected from the group consisting of
i) H,
ii) —$C_{1-6}$-alkyl, unsubstituted or substituted by 1 to 5 substituents individually selected from the group consisting of OH, halogen, cyano and $C_{1-6}$-alkoxy,
iii) —S(O)$_2$—$C_{1-6}$-alkyl, wherein the $C_{1-6}$-alkyl is unsubstituted or substituted by 1 to 5 substituents individually selected from the group consisting of OH, halogen, cyano and $C_{1-6}$-alkoxy,
iv) -C(O)—$C_{1-6}$-alkyl, wherein the $C_{1-6}$-alkyl is unsubstituted or substituted by 1 to 5 substituents individually selected from the group consisting of OH, halogen, cyano and $C_{1-6}$-alkoxy,
v) —C(O)O—$C_{1-6}$-alkyl, wherein the $C_{1-6}$-alkyl is unsubstituted or substituted by 1 to 5 substituents individually selected from the group consisting of OH, halogen, cyano and $C_{1-6}$-alkoxy;
vi) cycloalkyl, unsubstituted or substituted by 1 to 5 substituents individually selected from the group consisting of OH, halogen, cyano, $C_{1-6}$-alkyl and $C_{1-6}$-alkoxy;
vii) S(O)$_2$—(CH$_2$)$_q$—NR$^i$R$^{ii}$, wherein
q is 0 or 1,
R$^i$ and is each individually selected from the group consisting of H and $C_{1-6}$-alkyl, or
R$^i$ and R$^{ii}$ form together with the nitrogen to which they are attached a 3- to 7-membered heterocyclyl containing one or two heteroatoms individually selected from N, O and S, and which heterocyclyl is unsubstituted or substituted by 1 to 5 substituents individually selected from the group consisting of oxo, halogen, $C_{1-6}$-alkyl and $C_{1-6}$-alkoxy,
viii) —(CH$_2$)$_r$—NR$^{iii}$R$^{iv}$, wherein
r is 1, 2 or 3,
R$^{iii}$ and R$^{iv}$ is each individually selected from the group consisting of H and $C_{1-6}$-alkyl, or R$^{iii}$ and R$^{iv}$ form together with the nitrogen to which they are attached a 3- to 7-membered heterocyclyl containing one or two heteroatoms individually selected from N, O and S, and which heterocyclyl is unsubstituted or substituted by 1 to 5 substituents individually selected from the group consisting of oxo, halogen, $C_{1-6}$-alkyl and $C_{1-6}$-alkoxy, and
ix) —C(O)(CH$_2$)$_s$—NR$^v$R$^{vi}$, wherein
s is 1, 2 or 3,
R$^v$ and R$^{vi}$ is each individually selected from the group consisting of H and $C_{1-6}$-alkyl, or R$^v$ and R$^{vi}$ form together with the nitrogen to which they are attached a 3- to 7-membered heterocyclyl containing one or two heteroatoms individually selected from N, O and S, and which heterocyclyl is unsubstituted or substituted by 1 to 5 substituents individually selected from the group consisting of oxo, halogen, $C_{1-6}$-alkyl and $C_{1-6}$-alkoxy;
$R^2$ is halogen; and
$R^3$ is a 6-membered heteroaryl ring, unsubstituted or substituted by 1 to 5 substituents individually selected from the group consisting of OH, halogen, cyano, $C_{1-6}$-alkoxy, halogen-$C_{1-6}$-alkyl, halogen-$C_{1-6}$-alkoxy and 4-hydroxy-$C_{1-6}$-alkyl;
or a pharmaceutically acceptable salt thereof.

2. The compound of claim 1, wherein $R^1$ is selected from the group consisting of
i) H,
ii) —$C_{1-6}$-alkyl, unsubstituted or substituted by 1 to 2 substituents individually selected from the group consisting of halogen and $C_{1-6}$-alkoxy,
iii) —S(O)$_2$—$C_{1-6}$-alkyl, wherein the $C_{1-6}$-alkyl is unsubstituted,
iv) —C(O)—$C_{1-6}$-alkyl, wherein the $C_{1-6}$-alkyl is unsubstituted or substituted by 1 to 2 OH,
v) —C(O)O—$C_{1-6}$-alkyl, wherein the $C_{1-6}$-alkyl is unsubstituted;
vi) unsubstituted cycloalkyl,
vii) S(O)$_2$—(CH$_2$)$_q$—NR$^i$R$^{ii}$, wherein q is 0,
R$^{iii}$ and R$^{iv}$ is each individually selected from the group consisting of H and $C_{1-6}$-alkyl, and
viii) —(CH$_2$)$_r$—NR$^{iii}$R$^{iv}$, wherein r is 2,
R$^{iii}$ and R$^{iv}$ is each individually selected from the group consisting of H and $C_{1-6}$-alkyl, and
ix) —C(O)(CH$_2$)$_s$—NR$^v$R$^{vi}$, wherein s is 1,
R$^v$ and R$^{vi}$ is each individually selected from the group consisting of H and $C_{1-6}$-alkyl.

3. The compound of claim 2, wherein $R^1$ is selected from the group consisting of
i) H,
ii) —$C_{1-6}$-alkyl, unsubstituted or substituted by 1 to 2 substituents individually selected from the group consisting of halogen and $C_{1-6}$-alkoxy, and
iii) unsubstituted cycloalkyl.

4. The compound of claim 3, wherein $R^1$ is selected from the group consisting of H, methyl, ethyl, isopropyl, 2,2-difluoroethyl, 2-methoxy-ethyl and cyclobutyl.

5. The compound of claim 1, wherein $R^2$ is chloro.

6. The compound of claim 1, wherein $R^3$ is selected from the group consisting of
i) pyridinyl, unsubstituted or substituted by 1 to 2 substituents individually selected from the group consisting of halogen, $C_{1-6}$-alkyl and $C_{1-6}$-alkoxy,
ii) pyrazinyl, unsubstituted or substituted by 1 to 2 $C_{1-6}$-alkyl,
iii) unsubstituted pyridazinyl, and
iv) pyrimidinyl, unsubstituted or substituted by 1 to 2 $C_{1-6}$-alkyl.

7. The compound of claim 6, wherein R³ is
i) pyridinyl, unsubstituted or substituted by 1 to 2 substituents individually selected from the group consisting of halogen and C₁₋₆-alkyl, or
ii) unsubstituted pyrazinyl.

8. The compound of claim 7, wherein R³ is selected from the group consisting of pyridin-2-yl, 6-methyl-pyridin-2-yl, 3-chloro-pyridin-2-yl, 3,5-difluoro-pyridin-2-yl, 6-chloro-pyridin-2-yl, 5-fluoro-pyridin-2-yl, 3-fluoro-pyridin-2-yl and pyrazin-2-yl.

9. The compound of claim 8, wherein R³ is selected from the group consisting of pyridin-2-yl, 6-methyl-pyridin-2-yl, 6-chloro-pyridin-2-yl, 5-fluoro-pyridin-2-yl, 3-fluoro-pyridin-2-yl and pyrazin-2-yl.

10. The compound of claim 1 selected from the group consisting of trans-8-Chloro-5-methyl-1-(4-pyrimidin-2-yl-cyclohexyl)-5,6-dihydro-4H-2,3,5,10b-tetraaza-benzo[e]azulene,
  1-(trans-8-chloro-1-((1R,4S)-4-(3-fluoropyridin-2-yl)cyclohexyl)-4H-benzo[e][1,2,4]triazolo[4,3-a][1,4]diazepin-5(6H)-yl)ethanone,
  1-(trans-8-chloro-1-((1R,4S)-4-(3-fluoropyridin-2-yl)cyclohexyl)-4H-benzo[e][1,2,4]triazolo[4,3-a][1,4]diazepin-5(6H)-yl)-2-hydroxyethanone,
  1-(trans-8-chloro-1-((1R,4S)-4-(3-fluoropyridin-2-yl)cyclohexyl)-4H-benzo[e][1,2,4]triazolo[4,3-a][1,4]diazepin-5(6H)-yl)-2-(dimethylamino)ethanone formate,
  2-(trans-8-chloro-1-((1R,4S)-4-(3-fluoropyridin-2-yl)cyclohexyl)-4H-benzo[e][1,2,4]triazolo[4,3-a][1,4]diazepin-5(6H)-yl)-N-methylethanamine,
  trans-8-Chloro-1-[4-(3,5-difluoro-pyridin-2-yl)-cyclohexyl]-4H,6H-2,3,5,10b-tetraaza-benzo[e]azulene-5-carboxylic acid tert-butyl ester,
  trans-8-Chloro-1-[4-(3,5-difluoro-pyridin-2-yl)-cyclohexyl]-5,6-dihydro-4H-2,3,5,10b-tetraaza-benzo[e]azulene,
  trans-8-Chloro-1-[4-(3,5-difluoro-pyridin-2-yl)-cyclohexyl]-5-methyl-5,6-dihydro-4H-2,3,5,10b-tetraaza-benzo[e]azulene,
  trans-8-Chloro-1-[4-(3-chloro-pyridin-2-yl)-cyclohexyl]-4H,6H-2,3,5,10b-tetraaza-benzo[e]azulene-5-carboxylic acid tert-butyl ester,
  trans-8-Chloro-1-[4-(3-chloro-pyridin-2-yl)-cyclohexyl]-5,6-dihydro-4H-2,3,5,10b-tetraaza-benzo[e]azulene, and
  cis-8-chloro-1-((1S,4R)-4-(3-fluoropyridin-2-yl)cyclohexyl)-5,6-dihydro-4H-benzo[e][1,2,4]triazolo[4,3-a][1,4]diazepine.

11. The compound of claim 1 selected from the group consisting of
  cis-8-chloro-1-((1S,4R)-4-(3-fluoropyridin-2-yl)cyclohexyl)-5-methyl-5,6-dihydro-4H-benzo[e][1,2,4]triazolo[4,3-a][1,4]diazepine,
  cis-tert-butyl 8-chloro-1-((1R,4R)-4-(3-fluoropyridin-2-yl)cyclohexyl)-4H-benzo[e][1,2,4]triazolo[4,3-a][1,4]diazepine-5(6H)-carboxylate,
  trans-8-chloro-1-((1R,4R)-4-(2-fluoropyridin-3-yl)cyclohexyl)-5,6-dihydro-4H-benzo[e][1,2,4]triazolo[4,3-a][1,4]diazepine,
  trans-8-chloro-1-((1R,4R)-4-(2-fluoropyridin-3-yl)cyclohexyl)-5-methyl-5,6-dihydro-4H-benzo[e][1,2,4]triazolo[4,3-a][1,4]diazepine,
  trans-8-chloro-1-((1R,4S)-4-(2-chloropyridin-3-yl)cyclohexyl)-5-methyl-5,6-dihydro-4H-benzo[e][1,2,4]triazolo[4,3-a][1,4]diazepine,
  trans-8-chloro-1-((1R,4S)-4-(2-chloropyridin-3-yl)cyclohexyl)-5,6-dihydro-4H-benzo[e][1,2,4]triazolo[4,3-a][1,4]diazepine,
  trans-8-chloro-1-((1R,4S)-4-(2-methylpyrimidin-4-yl)cyclohexyl)-5,6-dihydro-4H-benzo[e][1,2,4]triazolo[4,3-a][1,4]diazepine,
  trans-8-chloro-1-((1R,4S)-4-(3-fluoropyridin-2-yl)cyclohexyl)-5-(2-methoxyethyl)-5,6-dihydro-4H-benzo[e][1,2,4]triazolo[4,3-a][1,4]diazepine,
  trans-8-chloro-1-((1R,4S)-4-(3-fluoropyridin-2-yl)cyclohexyl)-5-(methylsulfonyl)-5,6-dihydro-4H-benzo[e][1,2,4]triazolo[4,3-a][1,4]diazepine,
  trans-8-chloro-1-((1R,4S)-4-(3-fluoropyridin-2-yl)cyclohexyl)-5-isopropyl-5,6-dihydro-4H-benzo[e][1,2,4]triazolo[4,3-a][1,4]diazepine, and
  trans-8-chloro-1-((1R,4S)-4-(3-fluoropyridin-2-yl)cyclohexyl)-N,N-dimethyl-4H-benzo[e][1,2,4]triazolo[4,3-a][1,4]diazepine-5(6H)-sulfonamide.

12. The compound of claim 1 selected from the group consisting of
  trans-8-chloro-1-((1R,4S)-4-(3-methylpyrazin-2-yl)cyclohexyl)-5,6-dihydro-4H-benzo[e][1,2,4]triazolo[4,3-a][1,4]diazepine,
  trans-8-chloro-1-((1R,4S)-4-(4-chloropyridin-2-yl)cyclohexyl)-5,6-dihydro-4H-benzo[e][1,2,4]triazolo[4,3-a][1,4]diazepine,
  trans-8-chloro-1-((1R,4S)-4-(4-chloropyridin-2-yl)cyclohexyl)-5-methyl-5,6-dihydro-4H-benzo[e][1,2,4]triazolo[4,3-a][1,4]diazepine,
  trans-8-chloro-1-((1R,4S)-4-(6-fluoropyridin-2-yl)cyclohexyl)-5,6-dihydro-4H-benzo[e][1,2,4]triazolo[4,3-a][1,4]diazepine,
  trans-8-chloro-1-((1R,4S)-4-(6-fluoropyridin-2-yl)cyclohexyl)-5-methyl-5,6-dihydro-4H-benzo[e][1,2,4]triazolo[4,3-a][1,4]diazepine,
  trans-8-Chloro-1-(4-pyridin-2-yl-cyclohexyl)-5,6-dihydro-4H-2,3,5,10b-tetraaza-benzo[e]azulene dihydrochloride,
  trans-8-Chloro-1-[4-(3,6-dimethyl-pyrazin-2-yl)-cyclohexyl]-5,6-dihydro-4H-2,3,5,10b-tetraaza-benzo[e]azulene hydrochloride,
  trans-8-Chloro-1-[4-(4,6-dimethyl-pyrimidin-2-yl)-cyclohexyl]-5,6-dihydro-4H-2,3,5,10b-tetraaza-benzo[e]azulene hydrochloride,
  trans-8-Chloro-1-[4-(5-fluoro-pyridin-2-yl)-cyclohexyl]-4H,6H-2,3,5,10b-tetraaza-benzoazulene-5-carboxylic acid tert-butyl ester,
  trans-8-Chloro-1-[4-(6-isopropyl-pyridin-2-yl)-cyclohexyl]-5,6-dihydro-4H-2,3,5,10b-tetraaza-benzo[e]azulene hydrochloride, and
  trans-8-Chloro-1-[4-(6-methyl-pyrazin-2-yl)-cyclohexyl]-5,6-dihydro-4H-2,3,5,10b-tetraaza-benzo[e]azulene.

13. The compound of claim 1 selected from the group consisting of
  trans-8-chloro-5-(2,2-difluoroethyl)-1-((1R,4S)-4-(3-fluoropyridin-2-yl)cyclohexyl)-5,6-dihydro-4H-benzo[e][1,2,4]triazolo[4,3-a][1,4]diazepine,
  trans-8-chloro-5-cyclobutyl-1-((1R,4S)-4-(3-fluoropyridin-2-yl)cyclohexyl)-5,6-dihydro-4H-benzo[e][1,2,4]triazolo[4,3-a][1,4]diazepine,
  trans-8-chloro-5-ethyl-1-((1R,4S)-4-(3-fluoropyridin-2-yl)cyclohexyl)-5,6-dihydro-4H-benzo[e][1,2,4]triazolo[4,3-a][1,4]diazepine,
  trans-8-chloro-5-methyl-1-((1R,4S)-4-(2-methylpyrimidin-4-yl)cyclohexyl)-5,6-dihydro-4H-benzo[e][1,2,4]triazolo[4,3-a][1,4]diazepine, trans-8-chloro-5-methyl-1-((1R,4S)-4-(3-methylpyrazin-2-yl)cyclohexyl)-5,6-dihydro-4H-benzo[e][1,2,4]triazolo[4,3-a][1,4]diazepine, trans-8-fluoro-1-((1R,4S)-4-(3-fluoropyridin-2-yl)cyclohexyl)-5,6-dihydro-4H-benzo[e][1,2,4]triazolo[4,3-a][1,4]diazepine, trans-8-fluoro-1-((1R,4S)-4-(3-fluoropyridin-2-yl)cyclohexyl)-5-methyl-5,6-dihydro-4H-benzo[e][1,2,4]triazolo[4,3-a][1,4]diazepine, trans-tert-butyl 8-chloro-1-((1R,4R)-4-(2-fluoropyridin-3-yl)cyclohexyl)-4H-benzo[e][1,2,4]triazolo[4,3-a][1,4]diazepine-5(6H)-carboxylate, trans-tert-butyl 8-chloro-1-((1R,4S)-4-(2-chloropyridin-3-yl)cyclohexyl)-4H-benzo[e][1,2,4]triazolo[4,3-a][1,4]diazepine-5(6H)-carboxylate, trans-tert-butyl-8-chloro-1-((1R,4S)-4-(2-methylpyrimidin-4-yl)cyclohexyl)-4H-benzo[e][1,2,4]triazolo[4,3-a][1,4]diazepine-5(6H)-carboxylate, and trans-tert-butyl 8-chloro-1-((1R,4S)-4-(3-methylpyrazin-2-yl)cyclohexyl)-4H-benzo[e][1,2,4]triazolo[4,3-a][1,4]diazepine-5(6H)-carboxylate.

14. The compound of claim 1 selected from the group consisting of trans-tert-butyl 8-chloro-1-((1R,4S)-4-(4-chloropyridin-2-yl)cyclohexyl)-4H-benzo[e][1,2,4]triazolo[4,3-a][1,4]diazepine-5(6H)-carboxylate, trans-tert-butyl 8-chloro-1-((1R,4S)-4-(6-fluoropyridin-2-yl)cyclohexyl)-4H-benzo[e][1,2,4]triazolo[4,3-a][1,4]diazepine-5(6H)-carboxylate, trans-tert-butyl 8-fluoro-1-((1R,4S)-4-(3-fluoropyridin-2-yl)cyclohexyl)-4H-benzo[e][1,2,4]triazolo[4,3-a][1,4]diazepine-5(6H)-carboxylate, trans-8-Chloro-1-(4-pyridin-2-yl-cyclohexyl)-4H,6H-2,3,5,10b-tetraaza-benzo[e]azulene-5-carboxylic acid tert-butyl ester, trans-8-Chloro-1-(4-pyridin-2-yl-cyclohexyl)-5,6-dihydro-4H-2,3,5,10b-tetraaza-benzo[e]azulene, trans-8-Chloro-1-[4-(6-methyl-pyridin-2-yl)-cyclohexyl]-4H,6H-2,3,5,10b-tetraaza-benzo[e]azulene-5-carboxylic acid tert-butyl ester, trans-8-Chloro-1-[4-(6-methyl-pyridin-2-yl)-cyclohexyl]-5,6-dihydro-4H-2,3,5,10b-tetraaza-benzo[e]azulene, trans-8-Chloro-1-[4-(6-ethyl-pyridin-2-yl)-cyclohexyl]-4H,6H-2,3,5,10b-tetraaza-benzo[e]azulene-5-carboxylic acid tert-butyl ester, trans-8-Chloro-1-[4-(6-ethyl-pyridin-2-yl)-cyclohexyl]-5,6-dihydro-4H-2,3,5,10b-tetraaza-benzo[e]azulene, and trans-8-Chloro-1-[4-(6-ethyl-pyridin-2-yl)-cyclohexyl]-5-methyl-5,6-dihydro-4H-2,3,5,10b-tetraaza-benzo[e]azulene.

15. The compound of claim 1 selected from the group consisting of trans-8-Chloro-1-[4-(6-isopropyl-pyridin-2-yl)-cyclohexyl]-4H,6H-2,3,5,10b-tetraaza-benzo[e]azulene-5-carboxylic acid tert-butyl ester, trans-8-Chloro-1-[4-(6-isopropyl-pyridin-2-yl)-cyclohexyl]-5-methyl-5,6-dihydro-4H-2,3,5,10b-tetraaza-benzo[e]azulene, trans-8-Chloro-1-[4-(6-methoxy-pyridin-2-yl)-cyclohexyl]-4H,6H-2,3,5,10b-tetraaza-benzoazulene-5-carboxylic acid tert-butyl ester, trans-8-Chloro-1-[4-(6-methoxy-pyridin-2-yl)-cyclohexyl]-5,6-dihydro-4H-2,3,5,10b-tetraaza-benzoazulene, trans-8-Chloro-1-[4-(6-methoxy-pyridin-2-yl)-cyclohexyl]-5-methyl-5,6-dihydro-4H-2,3,5,10b-tetraaza-benzoazulene, trans-8-Chloro-1-[4-(6-chloro-pyridin-2-yl)-cyclohexyl]-4H,6H-2,3,5,10b-tetraaza-benzo[e]azulene-5-carboxylic acid tert-butyl ester, trans-tert-Butyl 8-chloro-1-(4-(6-fluoropyridin-2-yl)cyclohexyl)-4H-benzo[e][1,2,4]triazolo[4,3-a][1,4]diazepine-5(6H)-carboxylate, trans-8-Chloro-1-(4-(6-fluoropyridin-2-yl)cyclohexyl)-5,6-dihydro-4H-benzo[e][1,2,4]triazolo[4,3-a][1,4]diazepine, trans-8-Chloro-1-(4-(6-fluoropyridin-2-yl)cyclohexyl)-5-methyl-5,6-dihydro-4H-benzo[e][1,2,4]triazolo[4,3-a][1,4]diazepine, and trans-8-Chloro-1-[4-(5-fluoro-pyridin-2-yl)-cyclohexyl]-5,6-dihydro-4H-2,3,5,10b-tetraaza-benzoazulene.

16. The compound of claim 1 selected from the group consisting of trans-tert-Butyl 8-chloro-1-(4-(4-chloropyridin-2-yl)cyclohexyl)-4H-benzo[e][1,2,4]triazolo[4,3-a][1,4]diazepine-5(6H)-carboxylate, trans-8-chloro-1-(4-(4-chloropyridin-2-yl)cyclohexyl)-5,6-dihydro-4H-benzo[e][1,2,4]triazolo[4,3-a][1,4]diazepine, trans-8-Chloro-1-(4-(4-chloropyridin-2-yl)cyclohexyl)-5-methyl-5,6-dihydro-4H-benzo[e][1,2,4]triazolo[4,3-a][1,4]diazepine, trans-8-Chloro-1-[4-(3-fluoro-pyridin-2-yl)-cyclohexyl]-4H,6H-2,3,5,10b-tetraaza-benzo[e]azulene-5-carboxylic acid tert-butyl ester, trans-8-Chloro-1-[4-(3-fluoro-pyridin-2-yl)-cyclohexyl]-5,6-dihydro-4H-2,3,5,10b-tetraaza-benzo[e]azulene, trans-8-Chloro-5-ethyl-1-(4-(3-fluoropyridin-2-yl)cyclohexyl)-5,6-dihydro-4H-benzo[e][1,2,4]triazolo[4,3-a][1,4]diazepine, trans-8-Chloro-1-(4-(3-fluoropyridin-2-yl)cyclohexyl)-5-isopropyl-5,6-dihydro-4H-benzo[e][1,2,4]triazolo[4,3-a][1,4]diazepine, trans-8-Chloro-5-cyclobutyl-1-(4-(3-fluoropyridin-2-yl)cyclohexyl)-5,6-dihydro-4H-benzo[e][1,2,4]triazolo[4,3-a][1,4]diazepine, trans-8-Chloro-5-(2,2-difluoroethyl)-1-(4-(3-fluoropyridin-2-yl)cyclohexyl)-5,6-dihydro-4H-benzo[e][1,2,4]triazolo[4,3-a][1,4]diazepine, and trans-8-Chloro-1-(4-(3-fluoropyridin-2-yl)cyclohexyl)-5-(2-methoxyethyl)-5,6-dihydro-4H-benzo[e][1,2,4]triazolo[4,3-a][1,4]diazepine.

17. The compound of claim 1 selected from the group consisting of 2-(trans-8-Chloro-1-(4-(3-fluoropyridin-2-yl)cyclohexyl)-4H-benzo[e][1,2,4]triazolo[4,3-a][1,4]diazepin-5(6H)-yl)-N-methylethanamine, 1-(trans-8-chloro-1-(4-(3-fluoropyridin-2-yl)cyclohexyl)-4H-benzo[e][1,2,4]triazolo[4,3-a][1,4]diazepin-5(6H)-yl)ethanone, 1-(trans-8-chloro-1-(4-(3-fluoropyridin-2-yl)cyclohexyl)-4H-benzo[e][1,2,4]triazolo[4,3-a][1,4]diazepin-5(6H)-yl)-2-hydroxyethanone, 1-(trans-8-Chloro-1-(4-(3-fluoropyridin-2-yl)cyclohexyl)-4H-benzo[e][1,2,4]triazolo[4,3-a][1,4]diazepin-5(6H)-yl)-2-(dimethylamino)ethanone, trans-8-Chloro-1-(4-(3-fluoropyridin-2-yl)cyclohexyl)-5-(methylsulfonyl)-5,6-dihydro-4H-benzo[e][1,2,4]triazolo[4,3-a][1,4]diazepine, trans-8-Chloro-1-(4-(3-fluoropyridin-2-yl)cyclohexyl)-N,N-dimethyl-4H-benzo[e][1,2,4]triazolo[4,3-a][1,4]diazepine-5(6H)-sulfonamide, trans-tert-Butyl 8-fluoro-1-(4-(3-fluoropyridin-2-yl)cyclohexyl)-4H-benzo[e][1,2,4]triazolo[4,3-a][1,4]diazepine-5(6H)-carboxylate, trans-8-Fluoro-1-(4-(3-fluoropyridin-2-yl)cyclohexyl)-5,6-dihydro-4H-benzo[e][1,2,4]triazolo[4,3-a][1,4]diazepine, trans-8-Fluoro-1-(4-(3-fluoropyridin-2-yl)cyclohexyl)-5-methyl-5,6-dihydro-4H-benzo[e][1,2,4]triazolo[4,3-a][1,4]diazepine, and cis-tert-Butyl 8-chloro-1-(4-(3-fluoropyridin-2-yl)cyclohexyl)-4H-benzo[e][1,2,4]triazolo[4,3-a][1,4]diazepine-5(6H)-carboxylate.

18. The compound of claim 1 selected from the group consisting of cis-8-Chloro-1-(4-(3-fluoropyridin-2-yl)cyclohexyl)-5,6-dihydro-4H-benzo[e][1,2,4]triazolo[4,3-a][1,4]diazepine, cis-8-Chloro-1-(4-(3-fluoropyridin-2-yl)cyclohexyl)-5-methyl-5,6-dihydro-4H-benzo[e][1,2,4]triazolo[4,3-a][1,4]diazepine, trans-8-Chloro-1-(4-pyridin-3-yl-cyclohexyl)-4H,6H-2,3,5,10b-tetraaza-benzo[e]azulene-5-carboxylic acid tert-butyl ester, trans-8-Chloro-1-(4-pyridin-3-yl-cyclohexyl)-5,6-dihydro-4H-2,3,5,10b-tetraaza-benzo[e]azulene, trans-8-Chloro-5-methyl-1-(4-pyridin-3-yl-cyclohexyl)-5,6-dihydro-4H-2,3,5,10b-tetraaza-benzo[e]azulene, trans-tert-Butyl 8-chloro-1-(4-(2-chloropyridin-3-yl)cyclohexyl)-4H-benzo[e][1,2,4]triazolo[4,3-a][1,4]diazepine-5(6H)-carboxylate trans-8-Chloro-1-(4-(2-chloropyridin-3-yl)cyclohexyl)-5,6-dihydro-4H-benzo[e][1,2,4]triazolo[4,3-a][1,4]diazepine, trans-8-Chloro-1-(4-(2-chloropyridin-3-yl)cyclohexyl)-5-methyl-5,6-dihydro-4H-benzo[e][1,2,4]triazolo[4,3-a][1,4]diazepine, trans-tert-Butyl 8-chloro-1-(4-(2-fluoropyridin-3-yl)cyclohexyl)-4H-benzo[e][1,2,4]triazolo[4,3-a][1,4]diazepine-5(6H)-carboxylate, and trans-8-Chloro-1-(4-(2-fluoropyridin-3-yl)cyclohexyl)-5,6-dihydro-4H-benzo[e][1,2,4]triazolo[4,3-a][1,4]diazepine.

19. The compound of claim 1 selected from the group consisting of trans-8-Chloro-1-(4-(2-fluoropyridin-3-yl)cyclohexyl)-5-methyl-5,6-dihydro-4H-benzo[e][1,2,4]triazolo[4,3-a][1,4]diazepine, trans-8-Chloro-1-(4-pyrimidin-2-yl-cyclohexyl)-4H,6H-2,3,5,10b-tetraaza-benzo[e]azulene-5-carboxylic acid tert-butyl ester, cis-8-Chloro-1-(4-pyrimidin-2-yl-cyclohexyl)-4H,6H-2,3,5,10b-tetraaza-benzo[e]azulene-5-carboxylic acid tert-butyl ester, trans-8-Chloro-1-(4-pyrimidin-2-yl-cyclohexyl)-5,6-dihydro-4H-2,3,5,10b-tetraaza-benzo[e]azulene, cis-8-Chloro-1-(4-pyrimidin-2-yl-cyclohexyl)-5,6-dihydro-4H-2,3,5,10b-tetraaza-benzo[e]azulene, cis-8-Chloro-5-methyl-1-(4-pyrimidin-2-yl-cyclohexyl)-5,6-dihydro-4H-2,3,5,10b-tetraaza-benzo[e]azulene, trans-8-Chloro-1-[4-(4,6-dimethyl-pyrimidin-2-yl)-cyclohexyl]-4H,6H-2,3,5,10b-tetraaza-benzo[e]azulene-5-carboxylic acid tert-butyl ester, trans-8-Chloro-1-[4-(4,6-dimethyl-pyrimidin-2-yl)-cyclohexyl]-5,6-dihydro-4H-2,3,5,10b-tetraaza-benzo[e]azulene, trans-8-Chloro-1-[4-(4,6-dimethyl-pyrimidin-2-yl)-cyclohexyl]-5-methyl-5,6-dihydro-4H-2,3,5,10b-tetraaza-benzo[e]azulene, and trans-tert-Butyl 8-chloro-1-(4-(2-methylpyrimidin-4-yl)cyclohexyl)-4H-benzo[e][1,2,4]triazolo[4,3-a][1,4]diazepine-5(6H)-carboxylate.

20. The compound of claim 1 selected from the group consisting of trans-8-Chloro-1-(4-(2-methylpyrimidin-4-yl)cyclohexyl)-5,6-dihydro-4H-benzo[e][1,2,4]triazolo[4,3-a][1,4]diazepine, trans-8-Chloro-5-methyl-1-(4-(2-methylpyrimidin-4-yl)cyclohexyl)-5,6-dihydro-4H-benzo[e][1,2,4]triazolo[4,3-a][1,4]diazepine, trans-8-Chloro-1-(4-pyrazin-2-yl-cyclohexyl)-4H,6H-2,3,5,10b-tetraaza-benzo[e]azulene-5-carboxylic acid tert-butyl ester, trans-8-Chloro-1-(4-pyrazin-2-yl-cyclohexyl)-5,6-dihydro-4H-2,3,5,10b-tetraaza-benzo[e]azulene, trans-8-Chloro-5-methyl-1-(4-pyrazin-2-yl-cyclohexyl)-5,6-dihydro-4H-2,3,5,10b-tetraaza-benzo[e]azulene, trans-8-Chloro-1-[4-(6-methyl-pyrazin-2-yl)-cyclohexyl]-4H,6H-2,3,5,10b-tetraaza-benzo[e]azulene-5-carboxylic acid tert-butyl Ester, trans-8-Chloro-1-[4-(6-methyl-pyrazin-2-yl)-cyclohexyl]-5,6-dihydro-4H-2,3,5,10b-tetraaza-benzo[e]azulene, trans-8-Chloro-5-methyl-1-[4-(6-methyl-pyrazin-2-yl)-cyclohexyl]-5,6-dihydro-4H-2,3,5,10b-tetraaza-benzo[e]azulene, trans-tert-Butyl 8-chloro-1-(4-(3-methylpyrazin-2-yl)cyclohexyl)-4H-benzo[e][1,2,4]triazolo[4,3-a][1,4]diazepine-5(6H)-carboxylate, and trans-8-Chloro-1-(4-(3-methylpyrazin-2-yl)cyclohexyl)-5,6-dihydro-4H-benzo[e][1,2,4]triazolo[4,3-a][1,4]diazepine.

21. The compound of claim 1 selected from the group consisting of trans-8-Chloro-5-methyl-1-(4-(3-methylpyrazin-2-yl)cyclohexyl)-5,6-dihydro-4H-benzo[e][1,2,4]triazolo[4,3-a][1,4]diazepine, trans-8-Chloro-1-[4-(3,6-dimethyl-pyrazin-2-yl)-cyclohexyl]-4H,6H-2,3,5,10b-tetraaza-benzo[e]azulene-5-carboxylic acid tert-butyl ester, trans-8-Chloro-1-[4-(3,6-dimethyl-pyrazin-2-yl)-cyclohexyl]-5,6-dihydro-4H-2,3,5,10b-tetraaza-benzo[e]azulene, trans-8-Chloro-1-[4-(3,6-dimethyl-pyrazin-2-yl)-cyclohexyl]-5-methyl-5,6-dihydro-4H-2,3,5,10b-tetraaza-benzo[e]azulene, trans-8-Chloro-5-methyl-1-(4-pyridazin-3-yl-cyclohexyl)-5,6-dihydro-4H-2,3,5,10b-tetraaza-benzo[e]azulene, trans-8-Chloro-5-methyl-1-(4-pyrazin-2-yl-cyclohexyl)-5,6-dihydro-4H-2,3,5,10b-tetraaza-benzo[e]azulene, trans-8-Chloro-1-[4-(3-chloro-pyridin-2-yl)-cyclohexyl]-5-methyl-5,6-dihydro-4H-2,3,5,10b-tetraaza-benzo[e]azulene, trans-8-Chloro-1-[4-(3,5-difluoro-pyridin-2-yl)-cyclohexyl]-5-methyl-5,6-dihydro-4H-2,3,5,10b-tetraaza-benzo[e]azulene, trans-8-Chloro-1-(4-pyridin-2-yl-cyclohexyl)-5,6-dihydro-4H-2,3,5,10b-tetraaza-benzo[e]azulene.2HCl, trans-8-Chloro-5-methyl-1-(4-pyridin-2-yl-cyclohexyl)-5,6-dihydro-4H-2,3,5,10b-tetraaza-benzo[e]azulene, and trans-8-Chloro-5-methyl-1-[4-(6-methyl-pyridin-2-yl)-cyclohexyl]-5,6-dihydro-4H-2,3,5,10b-tetraaza-benzo[e]azulene.

22. The compound of claim 1 selected from the group consisting of trans-8-Chloro-1-[4-(6-chloro-pyridin-2-yl)-cyclohexyl]-5,6-dihydro-4H-2,3,5,10b-tetraaza-benzo[e]azulene, trans-8-Chloro-1-[4-(6-chloro-pyridin-2-yl)-cyclohexyl]-5-methyl-5,6-dihydro-4H-2,3,5,10b-tetraaza-benzo[e]azulene, trans-8-Chloro-1-[4-(5-fluoro-pyridin-2-yl)-cyclohexyl]-5,6-dihydro-4H-2,3,5,10b-tetraaza-benzoazulene dihydrochloride, trans-8-Chloro-1-[4-(5-fluoro-pyridin-2-yl)-cyclohexyl]-5-methyl-5,6-dihydro-4H-2,3,5,10b-tetraaza-benzoazulene, trans-8-Chloro-1-[4-(3-fluoro-pyridin-2-yl)-cyclohexyl]-5-methyl-5,6-dihydro-4H-2,3,5,10b-tetraaza-benzo[e]azulene, trans-8-Chloro-5-ethyl-1-(4-(3-fluoropyridin-2-yl)cyclohexyl)-5,6-dihydro-4H-benzo[e][1,2,4]triazolo[4,3-a][1,4]diazepine, trans-8-Chloro-1-(4-(3-fluoropyridin-2-yl)cyclohexyl)-5-isopropyl-5,6-dihydro-4H-benzo[e][1,2,4]triazolo[4,3-a][1,4]diazepine, trans-8-Chloro-5-cyclobutyl-1-(4-(3-fluoropyridin-2-yl)cyclohexyl)-5,6-dihydro-4H-benzo[e][1,2,4]triazolo[4,3-a][1,4]diazepine, trans-8-Chloro-5-(2,2-difluoroethyl)-1-(4-(3-fluoropyridin-2-yl)cyclohexyl)-5,6-dihydro-4H-benzo[e][1,2,4]triazolo[4,3-a][1,4]diazepine, trans-8-Chloro-1-(4-(3-fluoropyridin-2-yl)cyclohexyl)-5-(2-methoxyethyl)-5,6-dihydro-4H-benzo[e][1,2,4]triazolo[4,3-a][1,4]diazepine, and trans-8-Chloro-5-methyl-1-(4-pyrazin-2-yl-cyclohexyl)-5,6-dihydro-4H-2,3,5,10b-tetraaza-benzo[e]azulene.

23. A pharmaceutical composition comprising a therapeutically effective amount of a compound of formula I

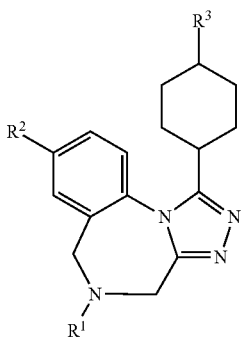

I wherein
$R^1$ is selected from the group consisting of
i) H,
ii) unsubstituted or substituted by 1 to 5 substituents individually selected from the group consisting of OH, halogen, cyano and $C_{1-6}$-alkoxy,
iii) —$S(O)_2$—$C_{1-6}$-alkyl, wherein the $C_{1-6}$-alkyl is unsubstituted or substituted by 1 to 5 substituents individually selected from the group consisting of OH, halogen, cyano and $C_{1-6}$-alkoxy,
iv) —C(O)—$C_{1-6}$-alkyl, wherein the $C_{1-6}$-alkyl is unsubstituted or substituted by 1 to 5 substituents individually selected from the group consisting of OH, halogen, cyano and $C_{1-6}$-alkoxy,
v) —C(O)O—$C_{1-6}$-alkyl, wherein the $C_{1-6}$-alkyl is unsubstituted or substituted by 1 to 5 substituents individually selected from the group consisting of OH, halogen, cyano and $C_{1-6}$-alkoxy;
vi) cycloalkyl, unsubstituted or substituted by 1 to 5 substituents individually selected from the group consisting of OH, halogen, cyano, $C_{1-6}$-alkyl and $C_{1-6}$-alkoxy;
vii) $S(O)_2$—$(CH_2)_q$—$NR^iR^{ii}$, wherein
q is 0 or 1,
$R^i$ and $R^{ii}$ is each individually selected from the group consisting of H and $C_{1-6}$-alkyl, or $R^i$ and $R^{ii}$ form together with the nitrogen to which they are attached a 3- to 7-membered heterocyclyl containing one or two heteroatoms individually selected from N, O and S, and which heterocyclyl is unsubstituted or substituted by 1 to 5 substituents individually selected from the group consisting of oxo, halogen, $C_{1-6}$-alkyl and $C_{1-6}$-alkoxy,
viii) —$(CH_2)_r$—$NR^{iii}R^{iv}$, wherein
r is 1, 2 or 3,
$R^{iii}$ and $R^{iv}$ is each individually selected from the group consisting of H and $C_{1-6}$-alkyl, or $R^{iii}$ and $R^{iv}$ form together with the nitrogen to which they are attached a 3- to 7-membered heterocyclyl containing one or two heteroatoms individually selected from N, O and S, and which heterocyclyl is unsubstituted or substituted by 1 to 5 substituents individually selected from the group consisting of oxo, halogen, $C_{1-6}$-alkyl and $C_{1-6}$-alkoxy, and
ix) —$C(O)(CH_2)_s$—$NR^vR^{vi}$, wherein
s is 1, 2 or 3,
$R^v$ and $R^{vi}$ is each individually selected from the group consisting of H and $C_{1-6}$-alkyl, or $R^v$ and $R^{vi}$ form together with the nitrogen to which they are attached a 3- to 7-membered heterocyclyl containing one or two heteroatoms individually selected from N, O and S, and which heterocyclyl is unsubstituted or substituted by 1 to 5 substituents individually selected from the group consisting of oxo, halogen, $C_{1-6}$-alkyl and $C_{1-6}$-alkoxy;
$R^2$ is halogen; and
$R^3$ is a 6-membered heteroaryl ring, unsubstituted or substituted by 1 to 5 substituents individually selected from the group consisting of OH, halogen, cyano, $C_{1-6}$-alkyl, $C_{1-6}$-alkoxy,
halogen-$C_{1-6}$-alkyl, halogen-$C_{1-6}$-alkoxy and 22-hydroxy-$C_{1-6}$-alkyl;
or a pharmaceutically acceptable salt thereof and a pharmaceutically acceptable carrier.

* * * * *